United States Patent
Sun et al.

(10) Patent No.: US 11,393,982 B2
(45) Date of Patent: Jul. 19, 2022

(54) 9,10-DIHYDRO-ACRIDINE DERIVATIVE, AND PREPARATION METHOD AND USE THEREOF

(71) Applicant: Ningbo Lumilan Advanced Materials., Ltd., Ningbo (CN)

(72) Inventors: Hua Sun, Ningbo (CN); Wenming Zhu, Ningbo (CN); Zhi Kuan Chen, Ningbo (CN)

(73) Assignee: NINGBO LUMILAN ADVANCED MATERIALS CO., LTD., Ningbo (CN)

( * ) Notice: Subject to any disclaimer, the term of this patent is extended or adjusted under 35 U.S.C. 154(b) by 516 days.

(21) Appl. No.: 16/261,750

(22) Filed: Jan. 30, 2019

(65) Prior Publication Data

US 2020/0091436 A1 Mar. 19, 2020

(30) Foreign Application Priority Data

Sep. 17, 2018 (CN) .......................... 201811084389.7

(51) Int. Cl.
*H01L 51/00* (2006.01)
*C07D 405/14* (2006.01)
(Continued)

(52) U.S. Cl.
CPC ........ *H01L 51/0067* (2013.01); *C07D 401/10* (2013.01); *C07D 401/14* (2013.01);
(Continued)

(58) Field of Classification Search
None
See application file for complete search history.

(56) References Cited

U.S. PATENT DOCUMENTS

2018/0138429 A1 5/2018 Fuchiwaki
2018/0155617 A1 6/2018 Nakano et al.
(Continued)

FOREIGN PATENT DOCUMENTS

CN 108516959 A 9/2018
CN 108586430 A 9/2018
(Continued)

OTHER PUBLICATIONS

Machine English translation of Ahn et al. (KR 10-2012-0021215). Jun. 22, 2021.*
(Continued)

*Primary Examiner* — Jay Yang
(74) *Attorney, Agent, or Firm* — Miles & Stockbridge P.C.; Ajay A. Jagtiani

(57) ABSTRACT

The invention relates to a 9,10-dihydro-acridine derivative having a structure of Formula (I). The HOMO and LUMO levels of the 9,10-dihydro-acridine derivative are distributed on different electron donating and electron withdrawing groups, such that the HOMO and LUMO levels are separated, achieving a small $\Delta E_{ST}$. The 9,10-dihydro-acridine derivative can be used as a TADF material in an organic light-emitting device. The dihydro-acridinyl group in the electron donating group is linked to a dibenzoheterocyclic ring. Introducing modifying groups allows adjustment of triplet and singlet energy levels of the compound, enabling the TADF material to have a high luminescence efficiency in blue and deep blue regions. The invention also relates to an organic light-emitting device having at least one functional layer containing the 9,10-dihydro-acridine derivative. When the compound is used as a guest luminescent material in a light emitting layer, an OLED device of high blue light emitting efficiency is obtained.

8 Claims, 2 Drawing Sheets

(51) Int. Cl.
- *C07D 409/14* (2006.01)
- *C07D 401/14* (2006.01)
- *C07D 401/10* (2006.01)
- *C09K 11/06* (2006.01)
- *C09K 11/02* (2006.01)
- *H01L 51/50* (2006.01)

(52) U.S. Cl.
CPC ......... *C07D 405/14* (2013.01); *C07D 409/14* (2013.01); *C09K 11/025* (2013.01); *C09K 11/06* (2013.01); *H01L 51/0072* (2013.01); *H01L 51/0073* (2013.01); *H01L 51/0074* (2013.01); *C09K 2211/1018* (2013.01); *H01L 51/5016* (2013.01)

(56) References Cited

U.S. PATENT DOCUMENTS

| | | | |
|---|---|---|---|
| 2018/0201632 | A1 | 7/2018 | Fuchiwaki |
| 2018/0237460 | A1 | 8/2018 | Ahn et al. |

FOREIGN PATENT DOCUMENTS

| | | | |
|---|---|---|---|
| CN | 108658941 | A | 10/2018 |
| CN | 109232419 | A | 1/2019 |
| KR | 1020120021215 | A | 3/2012 |
| KR | 1020130142967 | A | 12/2013 |

OTHER PUBLICATIONS

Second Office Action CN Application No. 201811084389.7, issued in corresponding application dated Jun. 5, 2020.
International Search Report and Written Opinion based on PCT/CN2018/113120 dated May 28, 2019.
First Office Action CN Application No. 201811084389.7, issued in corresponding application dated Nov. 28, 2019.
Pope et al., Electroluminescence in Organic Crystals, The Journal of Chemical Physics 38, pp. 2042 (1963).
Tang et al., Organic Electroluminescent Diodes, Appl. Phys. Lett. 51, pp. 913-915 (Sep. 21, 1987).
Lee et al., Effect of hole transporting materials in phosphorescent white polymer light-emitting diodes, Organic Electronics 11, pp. 427-433 (2010).
Fang, et al., Improved efficiency by a fluorescent dye in red organic light-emitting devices based on a europium complex, Chemical Physics Letters 392, pp. 11-16 (2004).
Shirota, et al., Charge Carrier Transporting Molecular Materials and Their Applications in Devices, Chem. Rev. 2007, vol. 107, pp. 953-1010.
Goushi, et al. Triplet exciton confinement and unconfinement by adjacent hole-transport layers, Journal of Applied Physics, vol. 95, No. 12, pp. 7798-7802 (Jun. 15, 2004).
Uoyama, et al., Highly efficient organic light-emitting diodes from delayed fluorescence, Nature, vol. 492, pp. 234-238, Dec. 12, 2012.

* cited by examiner

9,10-DIHYDRO-ACRIDINE DERIVATIVE, AND PREPARATION METHOD AND USE THEREOF

CROSS-REFERENCE TO RELATED APPLICATION

This application claims the priority to Chinese Patent Application No. 2018110843897 filed on Sep. 17, 2018 with the State Intellectual Property Office of the People's Republic of China, and entitled "9,10-dihydro-acridine derivative and preparation method and use thereof", which is incorporated herein by reference in its entirety.

TECHNICAL FIELD

The present invention relates to the field of display technologies, and particularly to a 9,10-dihydro-acridine derivative, and a preparation method and use thereof.

RELATED ART

Organic light-emitting diodes (OLEDs) have broad application prospects in the field of display and illumination due to the advantages of ultrathin thickness, light weight, low power consumption, self-lighting, wide viewing angle, and fast response time, thus receiving more and more attention.

OLEDs are ambipolar carrier injection-type light-emitting devices. The light-emission mechanism is as follows. Driven by an external electric field, electrons and holes are injected into an organic functional layer respectively from a cathode and an anode, and recombined to form excitons in the organic light-emitting layer, and then the excitons go back to the ground state by radiation transition and emit light. The material of organic light emitting layer is of great importance for the performance of OLED devices.

In 1987, Deng Qingyun (C. W. Tang) and Vanslyke from Eastman Kodak Company (US) initially reported that a double-layer organic light-emitting device is fabricated by using a transparent conductive film as an anode, Alq3 as a light emitting layer, triarylamine as a hole transport layer, and Mg/Ag alloy as a cathode. Conventional fluorescent materials are easy to synthesize, and stable, and the service life of devices containing them is long. However, due to spin-forbidden transition of the electrons, only the singlet excitons of 25% can be utilized for emitting light, and the triplet excitons of 75% are wasted, so the external quantum efficiency of the device is generally lower than 5%, and needs to be further improved. In order to improve the efficiency of OLED devices, it is proposed to introduce heavy metal atoms into the molecules of organic materials. Due to the spin-quantum coupling of heavy metal atoms, the excitons are facilitated to transition from the lowest triplet state ($T_1$) to the ground state ($S_0$) to phosphoresce. In this method, the triplet and singlet excitons are both captured, allowing the internal quantum efficiency of the device to reach 100%. However, heavy metals such as iridium (Ir) and platinum (Pt), which are commonly used in phosphorescent devices, have a higher material cost, which limits their further development.

In order to reduce the cost and break through the internal quantum efficiency limit of 25% of OLED devices, Professor Adachi from Kyushu University in Japan proposed the mechanism of thermally activated delayed fluorescence (TADF). In organic small molecular materials with low singlet-triplet energy level difference ($\Delta E_{ST}$), the triplet excitons can be converted into singlet excitons by reverse intersystem crossing (RISC). In theory, the internal quantum efficiency of the device can reach 100%. TADF materials can combine the advantages of both fluorescent and phosphorescent materials, and are known as the third-generation organic light-emitting materials, which have attracted wide attention.

So far, a series of TADF materials with high luminescence efficiency have been developed. However, the blue TADF materials are limited by the short wavelength of blue light, the high energy required for radiation luminescence and the small $\Delta E_{ST}$ required by TADF materials, and the blue TADF materials have undesirable luminescence efficiency.

SUMMARY

Therefore, the technical problem to be solved by the present invention is to overcome the drawbacks in the prior art that the thermally activated delayed fluorescent material cannot achieve high blue light and deep blue light emitting efficiency.

To this end, the present invention provides the following technical solutions.

The present invention provides a 9,10-dihydro-acridine derivative having a structure of Formula (I):

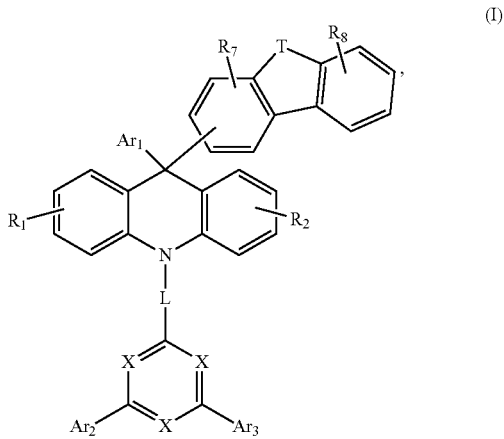

wherein each X is independently selected from N or $C(R_3)$; and T is selected from O, S, $C(R_4)(R_5)$ or $N(R_6)$;

$R_1$-$R_6$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, or a C3-C30 substituted or unsubstituted heteroaryl group;

$R_7$-$R_8$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, a C3-C30 substituted or unsubstituted heteroaryl group, or a ring A that shares a side with the adjacent phenyl group to form a fused ring, in which the ring A is selected from a phenyl ring, a 3- to 7-membered saturated or partially unsaturated carbocyclic ring, a 3- to 7-membered saturated or partially heterocyclic ring, a fused C6-C60 aryl group or a fused C3-C30 heteroaryl group;

$Ar_1$-$Ar_3$ are each independently selected from hydrogen, deuterium, halo, cyano, a C1-C30 substituted or unsubstituted alkyl group, a C2-C30 substituted or unsubstituted alkenyl group, a C2-C30 substituted or unsubstituted alkynyl group, a C3-C30 substituted or unsubstituted cycloalkyl group, a C1-C30 substituted or unsubstituted alkoxy group, a C1-C30 substituted or unsubstituted silyl group, a C6-C60 substituted or unsubstituted aryl group, or a C3-C30 substituted or unsubstituted heteroaryl group; and L is a single bond, a C1-C10 substituted or unsubstituted aliphatic hydrocarbon group, a C6-C60 substituted or unsubstituted aryl group, or a C3-C30 substituted or unsubstituted heteroaryl group;

in which the heteroaryl, heterocyclic ring and fused heteroaryl each independently have at least one heteroatom independently selected from nitrogen, sulfur, oxygen, phosphorus, boron or silicon.

Optionally, in the 9,10-dihydro-acridine derivative according to claim 1, L and $Ar_1$-$Ar_3$ are each independently selected from a C6-C60 substituted or unsubstituted fused aryl group, a C3-C30 substituted or unsubstituted bridged cycloalkyl group, a C3-C30 substituted or unsubstituted monocyclic heteroaryl group, or a C3-C30 substituted or unsubstituted fused heteroaryl group.

Optionally, in the 9,10-dihydro-acridine derivative, L and $Ar_1$-$Ar_3$ are each independently selected from phenyl, biphenylyl, adamantyl, naphthyl, anthracenyl, phenanthrenyl, fluorenyl, pyrenyl, perylenyl, corranulenyl, triphenylene, fluoranthenyl, pyridinyl, pyrimidinyl, pyranyl, thiopyranyl, pyrazinyl, pyridazinyl, triazinyl, phthalazinyl, phenazinyl, thienyl, furyl, pyrrolyl, pyrazolyl, imidazolyl, oxazolyl, thiazolyl, indolyl, carbazolyl, indolocarbazolyl, triarylamino, diarylamino, phenanthridinyl, acridinyl, perimidinyl, pteridinyl, quinazolinyl, quinoxalinyl, cinnolinyl, quinolyl, phenanthrolinyl, and carbolinyl that is unsubstituted or substituted with 1-5 $R_{1a}$, or a fused cyclic group, a spirocyclic group or a bicyclic group formed by the aforesaid groups, in which $R_{1a}$ is selected from cyano or a $C_1$-$C_6$ alkyl.

Optionally, in the 9,10-dihydro-acridine derivative, at least one X is nitrogen in the compound of Formula (I).

Optionally, in the 9,10-dihydro-acridine derivative, $R_1$-$R_6$ are each independently selected from hydrogen, a $C_1$-$C_6$ alkyl, phenyl, biphenylyl, adamantyl, naphthyl, anthracenyl, phenanthrenyl, fluorenyl, pyrenyl, perylenyl, corranulenyl, triphenylene, fluoranthenyl, pyridinyl, pyrimidinyl, pyranyl, thiopyranyl, pyrazinyl, pyridazinyl, triazinyl, phthalazinyl, phenazinyl, thienyl, furyl, pyrrolyl, pyrazolyl, imidazolyl, oxazolyl, thiazolyl, indolyl, carbazolyl, indolocarbazolyl, triarylamino, diarylamino, phenanthridinyl, acridinyl, perimidinyl, pteridinyl, quinazolinyl, quinoxalinyl, cinnolinyl, quinolyl, phenanthrolinyl or carbolinyl;

$R_7$-$R_8$ are each independently selected from hydrogen, a $C_1$-$C_6$ alkyl, phenyl, biphenylyl, adamantyl, naphthyl, anthracenyl, phenanthrenyl, fluorenyl, pyrenyl, perylenyl, corranulenyl, triphenylene, fluoranthenyl, pyridinyl, pyrimidinyl, pyranyl, thiopyranyl, pyrazinyl, pyridazinyl, triazinyl, phthalazinyl, phenazinyl, thienyl, furyl, pyrrolyl, pyrazolyl, imidazolyl, oxazolyl, thiazolyl, indolyl, carbazolyl, indolocarbazolyl, triarylamino, diarylamino, phenanthridinyl, acridinyl, perimidinyl, pteridinyl, quinazolinyl, quinoxalinyl, cinnolinyl, quinolyl, phenanthrolinyl, carbolinyl or a ring A that shares a side with the adjacent phenyl group to form a fused ring, where the ring A is selected from

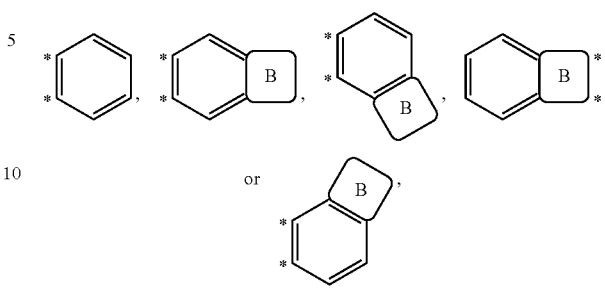

in which the ring B is selected from a benzene ring, a biphenyl ring, an adamantane ring, a naphthalene ring, an anthracene ring, a phenanthrene ring, a fluorene ring, a pyrene ring, a perylene ring, a corranulene ring, a triphenylene ring, a fluoranthene ring, a pyridine ring, a pyrimidine ring, a pyran ring, a thiapyran ring, a pyrazine ring, a pyridazine ring, a triazine ring, a phthalazine ring, a phenazine ring, a thiophene ring, a furan ring, a pyrrole ring, a pyrazole ring, an imidazole ring, an oxazole ring, a thiazole ring, an indole ring, a carbazole ring, an indolocarbazole ring, a triarylamine ring, a diarylamine ring, a phenanthridine ring, an acridine ring, a perimidine ring, a pteridine ring, a quinazoline ring, a quinoxaline ring, a cinnoline ring, a quinoline ring, a phenanthroline ring or a carboline ring.

Optionally, the 9,10-dihydro-acridine derivative has any of the following molecular structures:

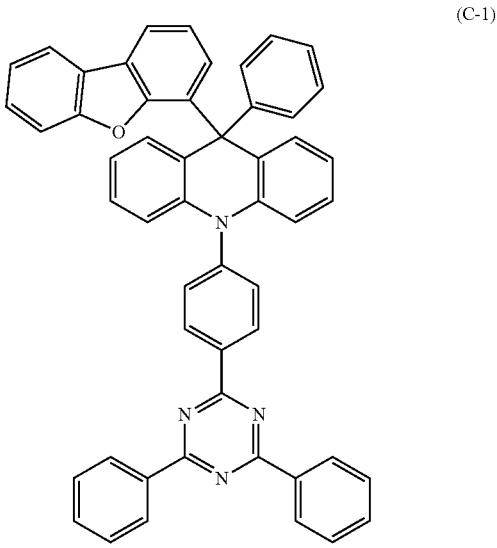

(C-1)

(C-2)
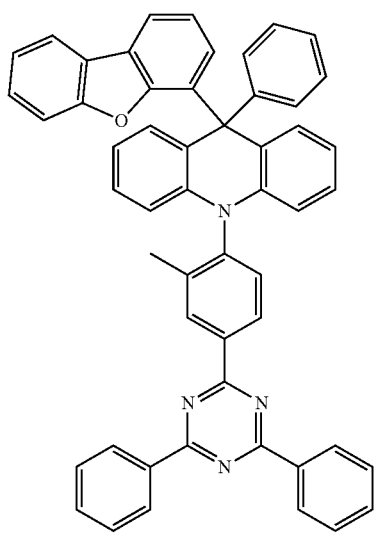
(C-5)
(C-3)
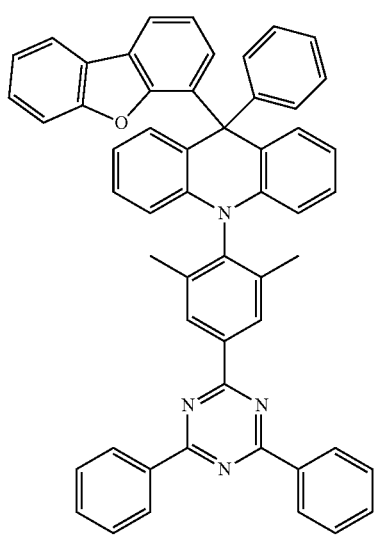
(C-6)
(C-4)
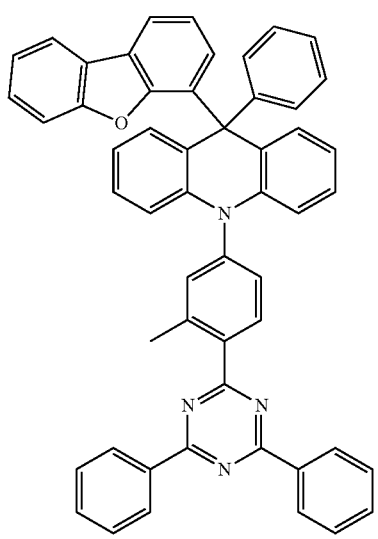
(C-7)

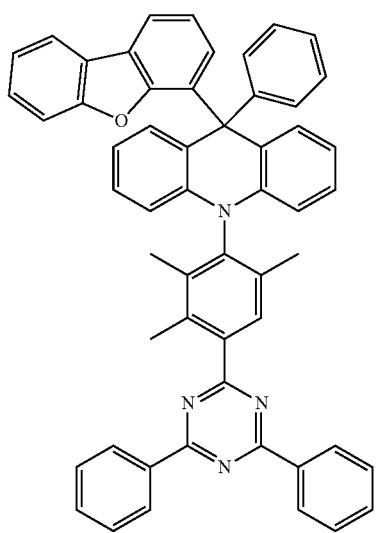
(C-8)
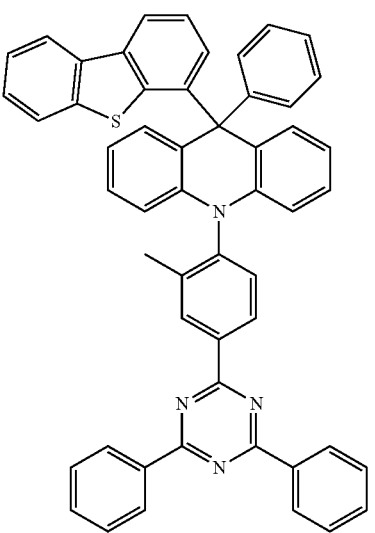
(C-11)
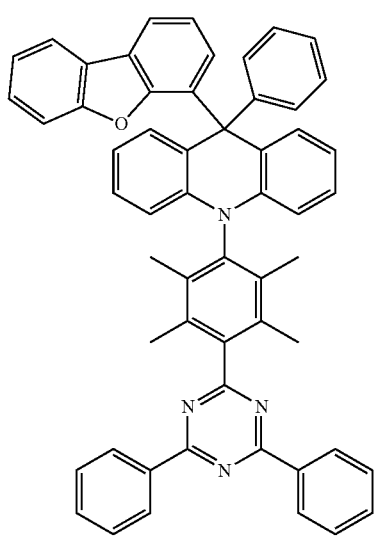
(C-9)
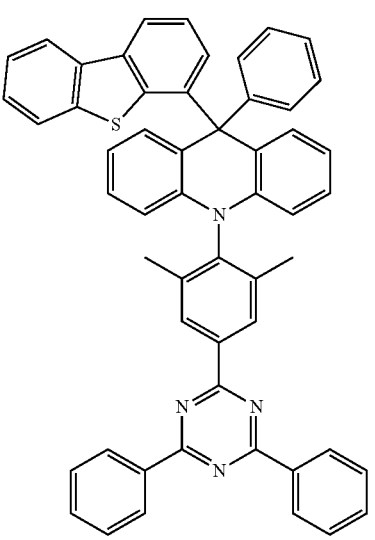
(C-12)
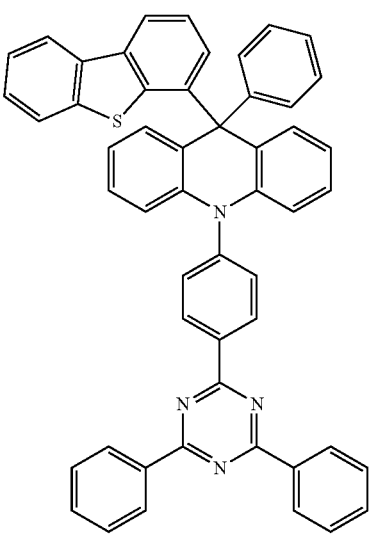
(C-10)
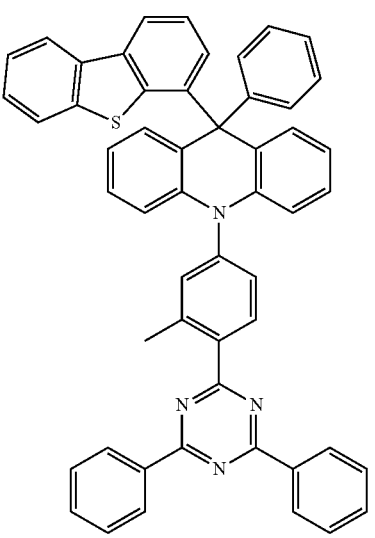
(C-13)

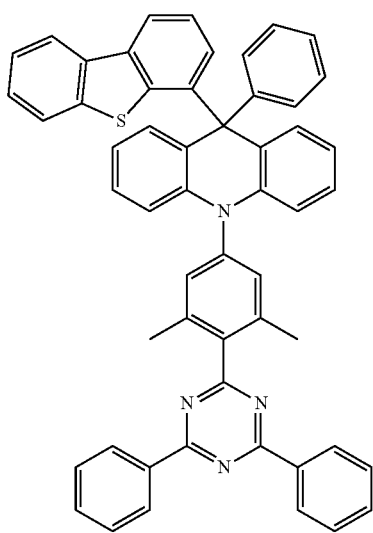
(C-14)
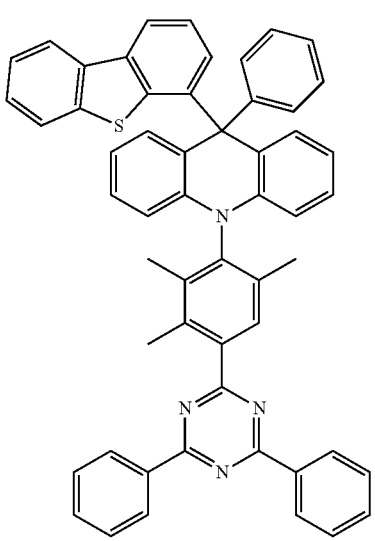
(C-17)
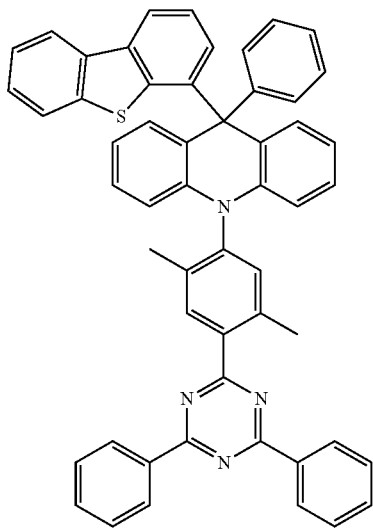
(C-15)
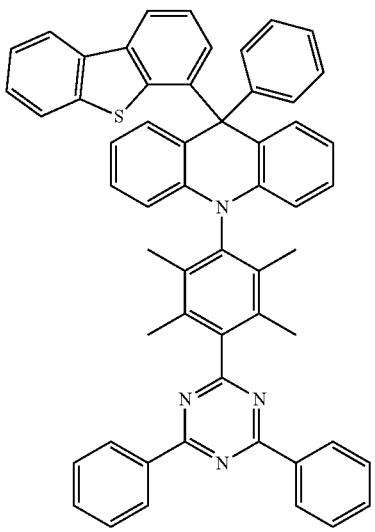
(C-18)
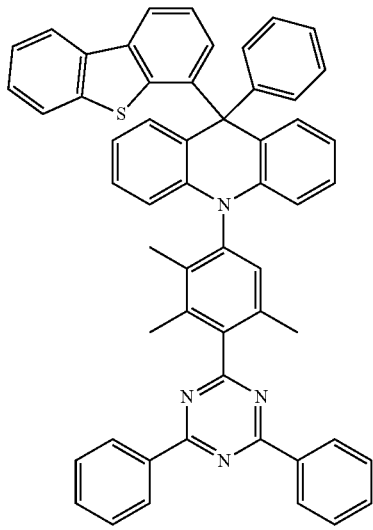
(C-16)
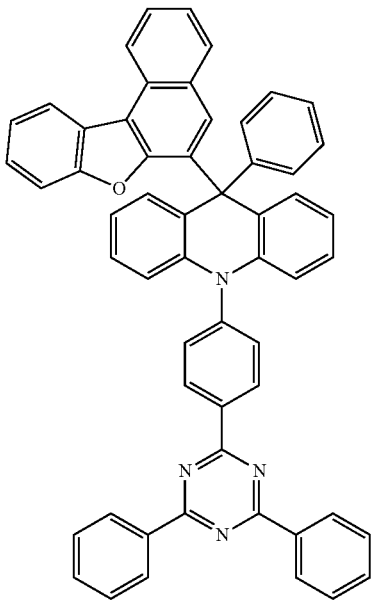
(C-19)

(C-20)
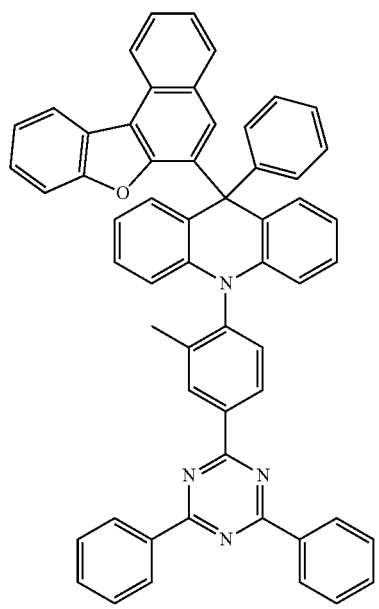
(C-21)
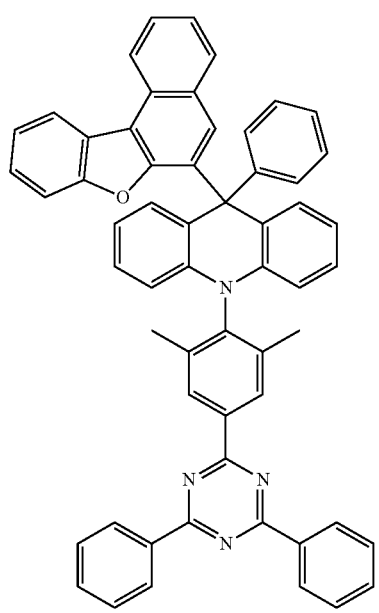
(C-22)
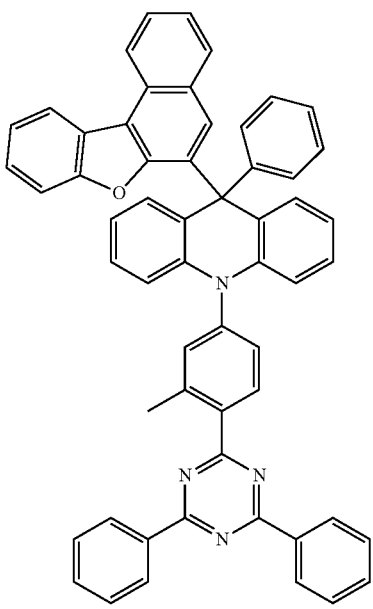
(C-23)
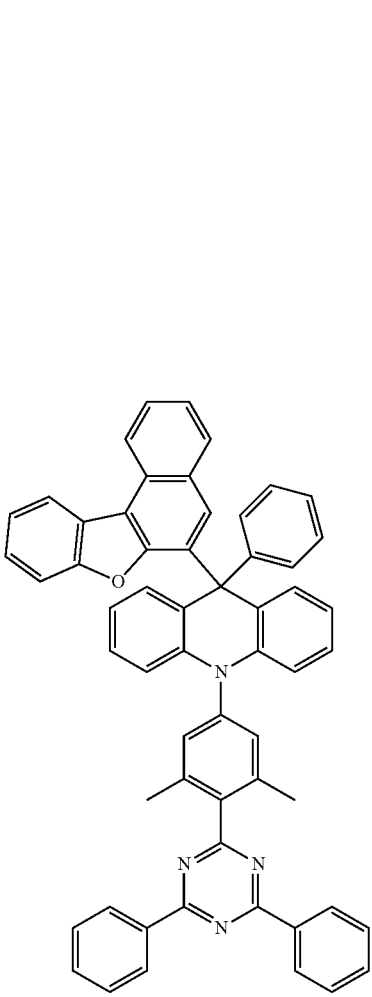

(C-24)
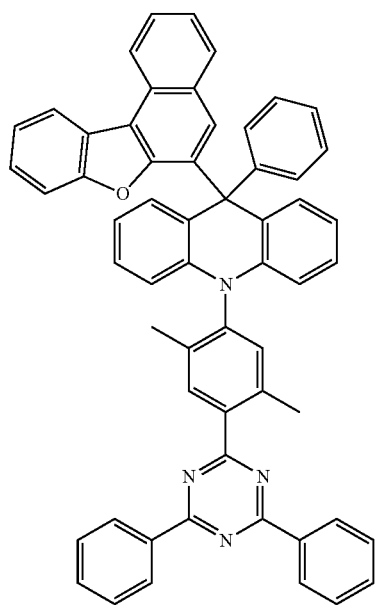
(C-25)
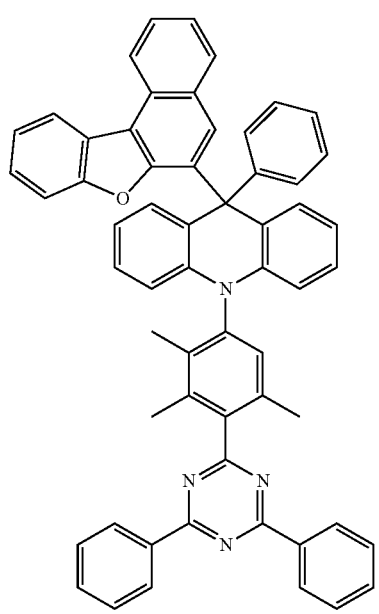
(C-26)
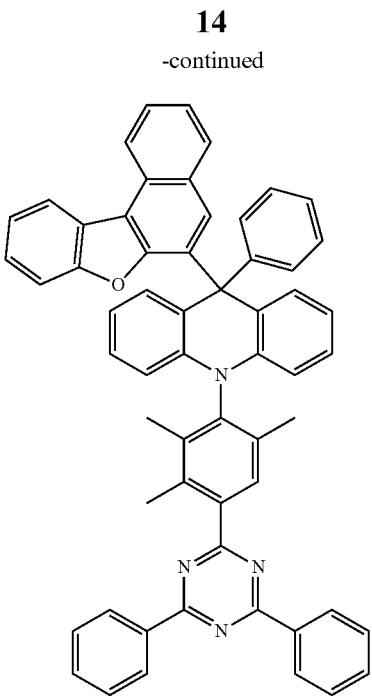
(C-27)
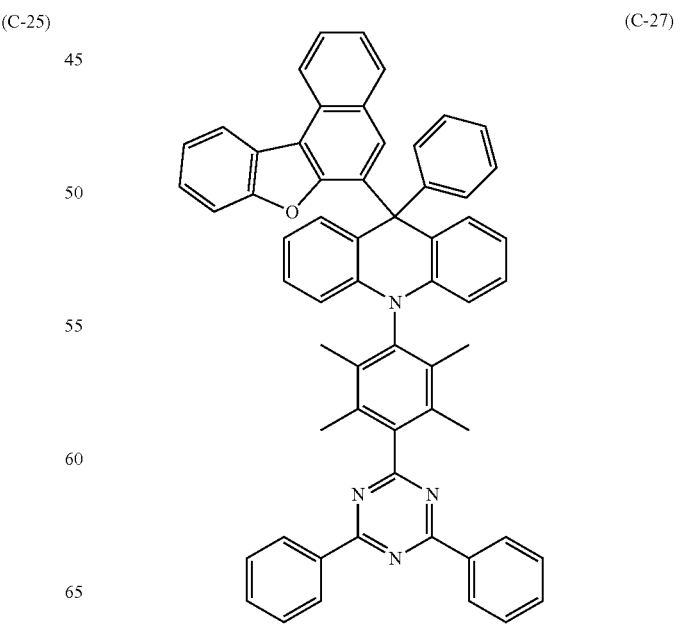

(C-28)
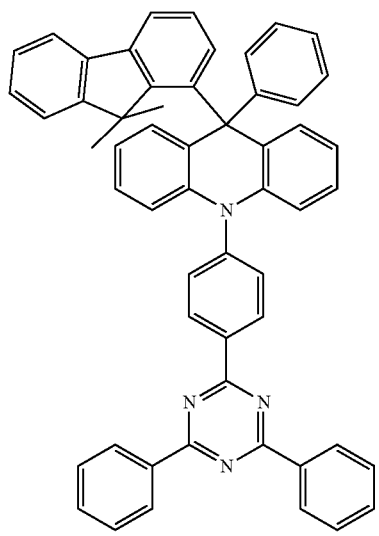
(C-31)
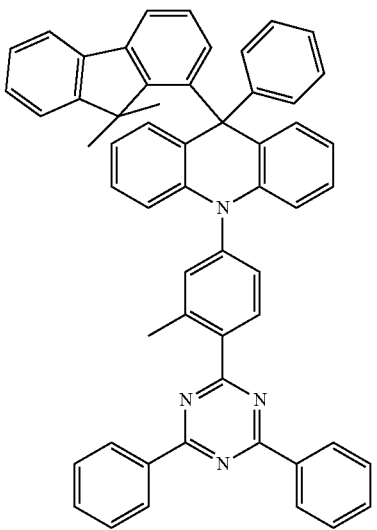
(C-29)
(C-32)
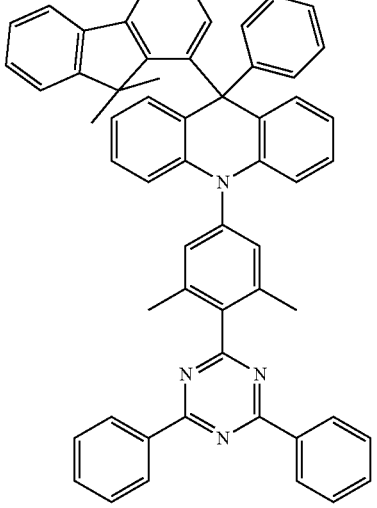
(C-30)
(C-33)
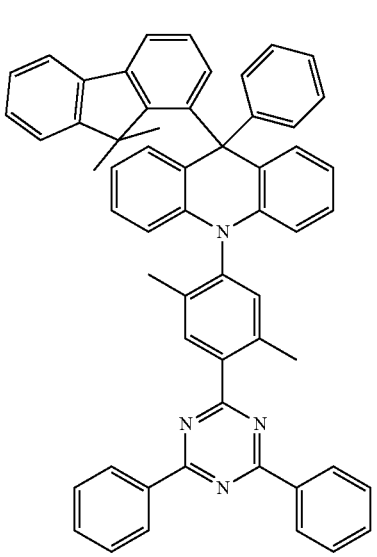

(C-34)
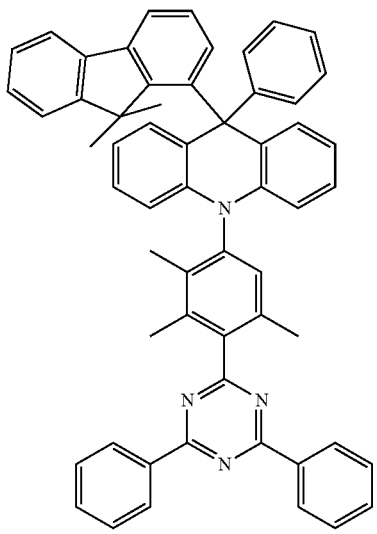
(C-35)
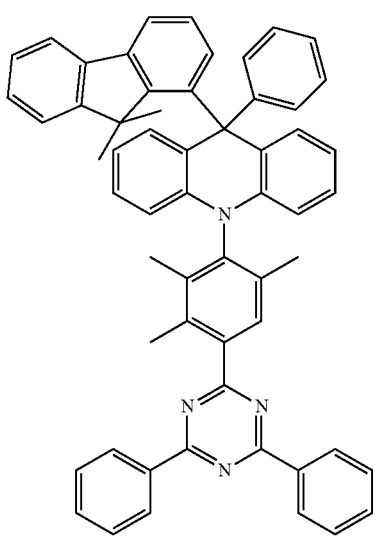
(C-36)
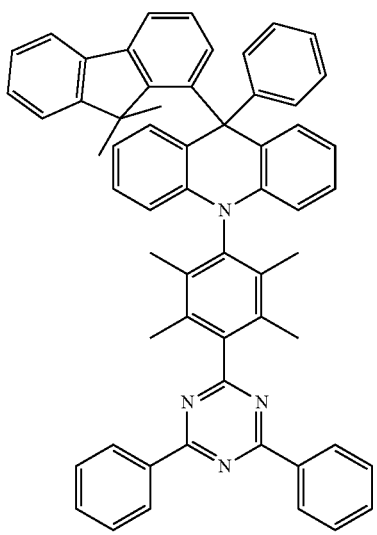
(C-37)
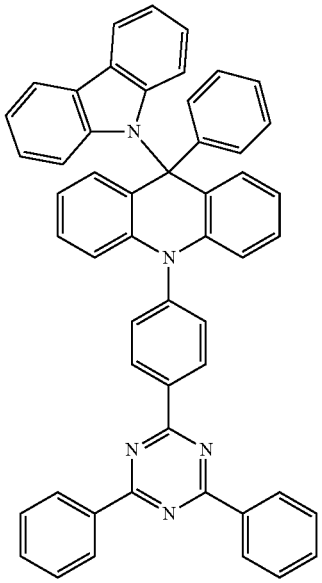
(C-38)
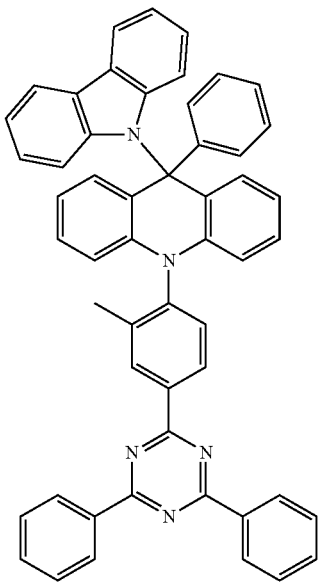

(C-39)
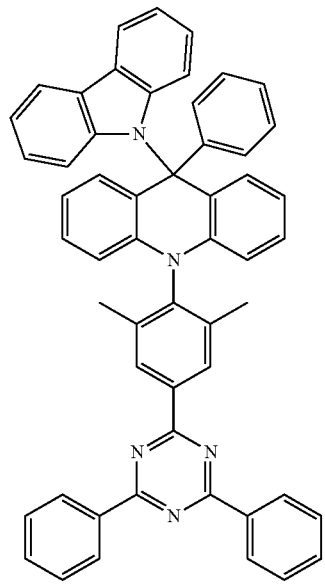
(C-40)
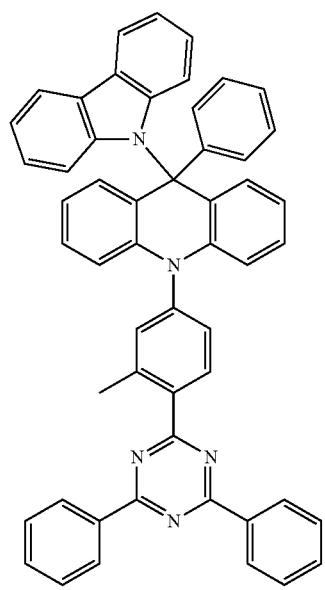
(C-41)
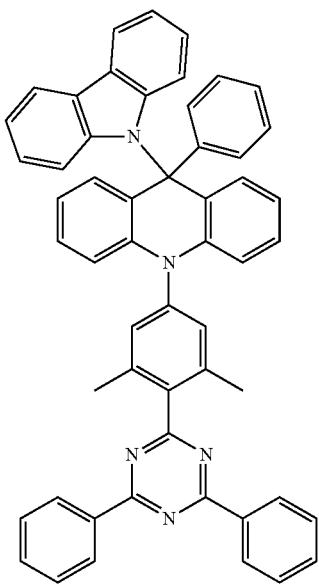
(C-42)
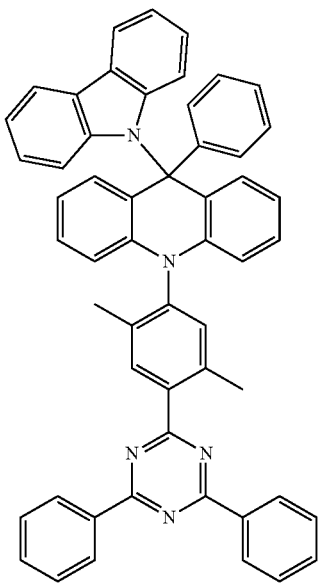

(C-43)
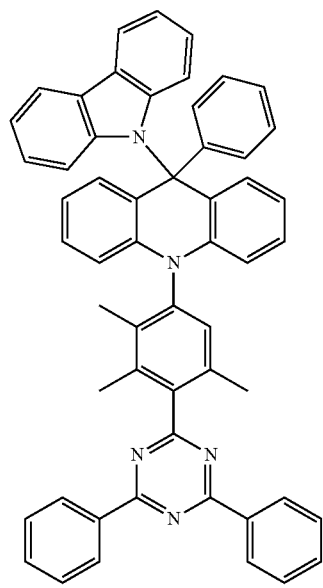
(C-44)
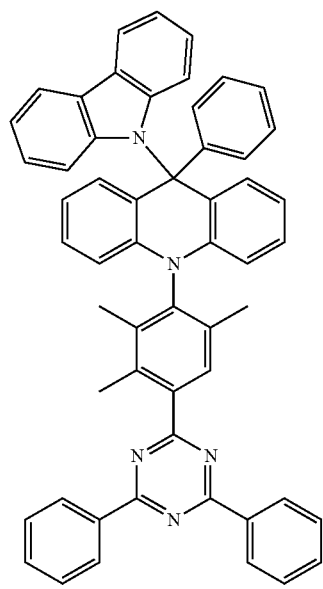
(C-45)
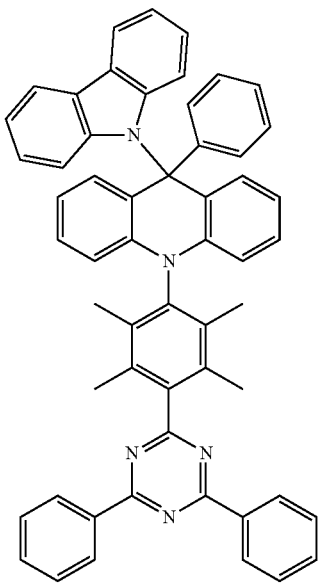
(C-46)
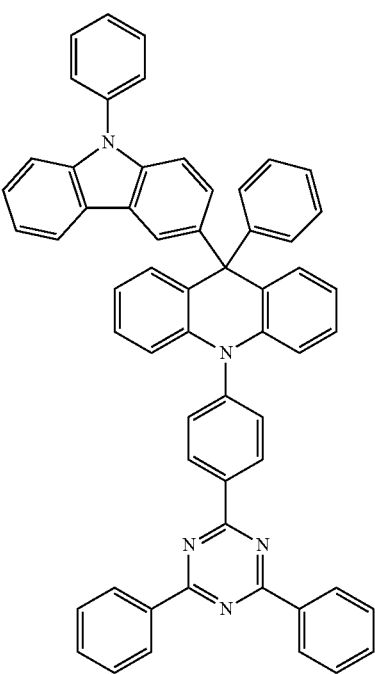

(C-47)
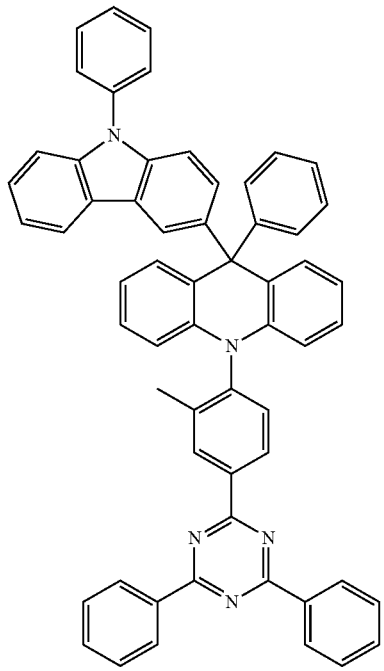
(C-49)
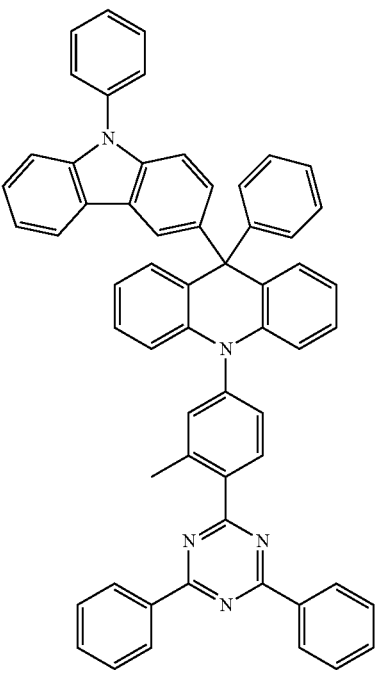
(C-48)
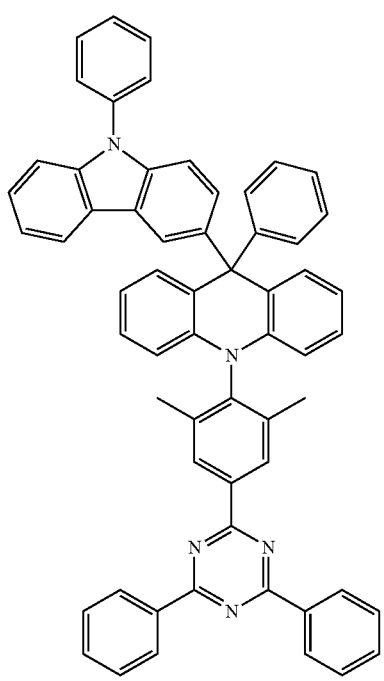
(C-50)
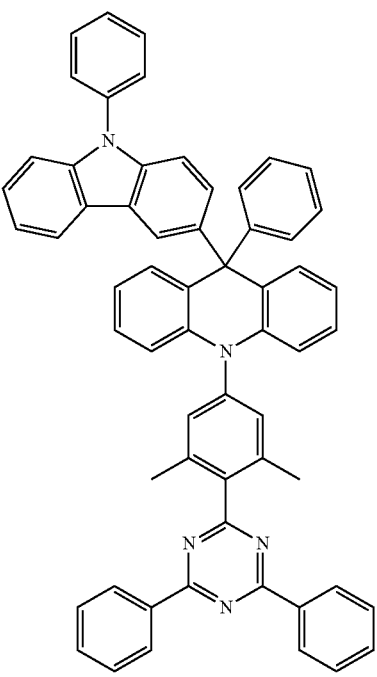

(C-51)
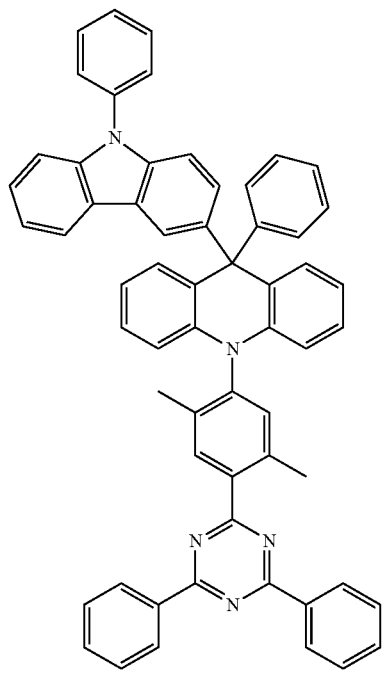
(C-53)
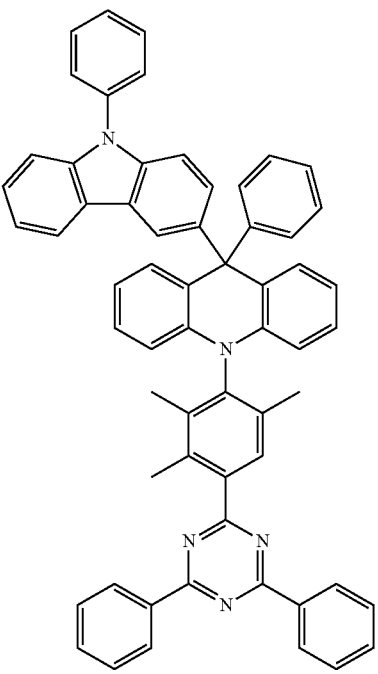
(C-52)
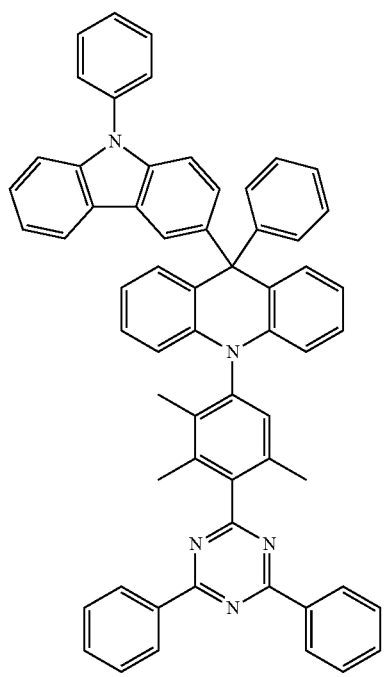
(C-54)
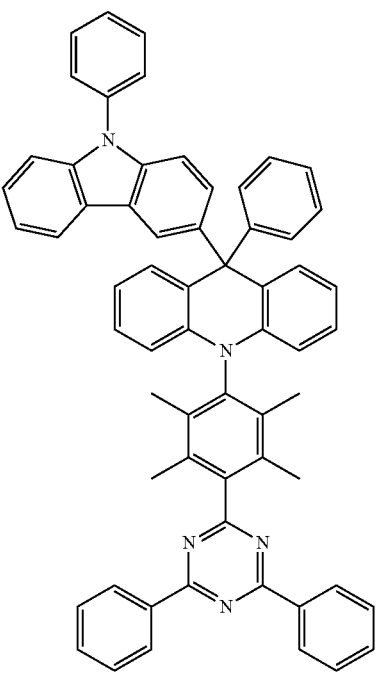

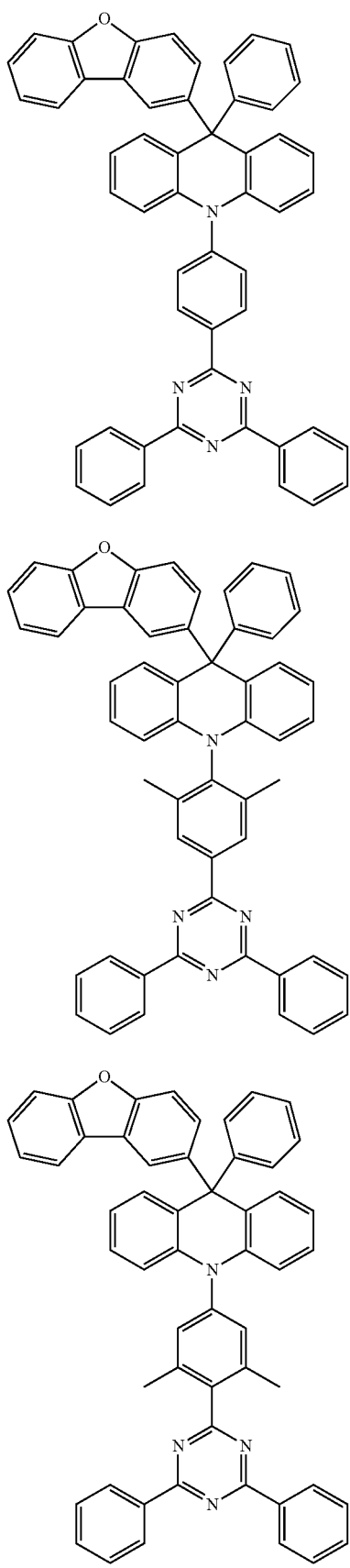
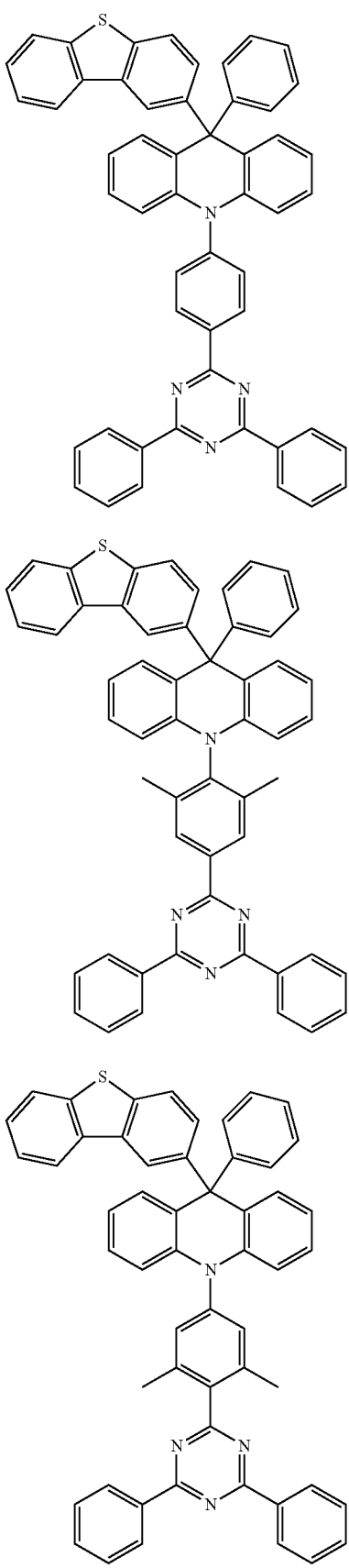

(C-61)
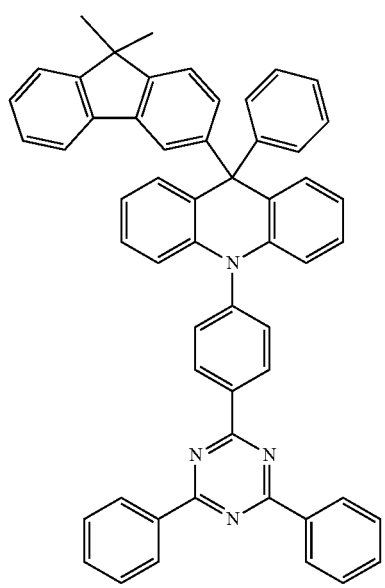
(C-62)
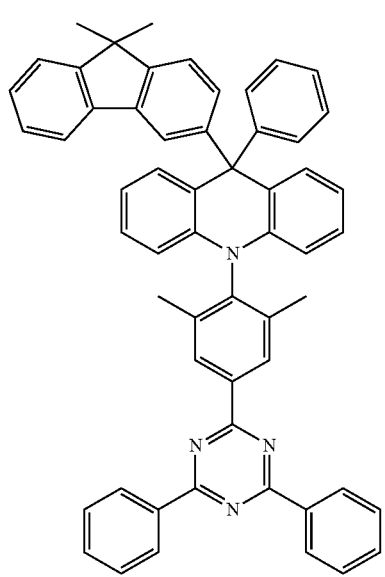
(C-63)
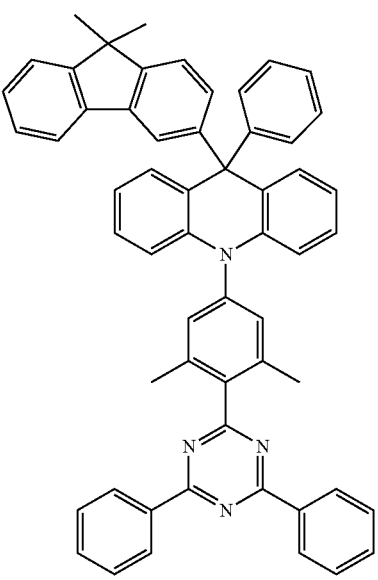
(C-64)
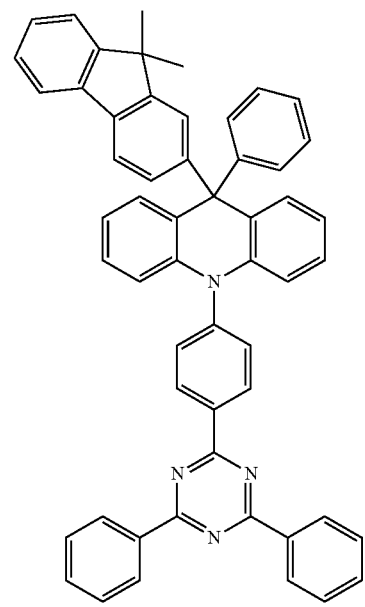

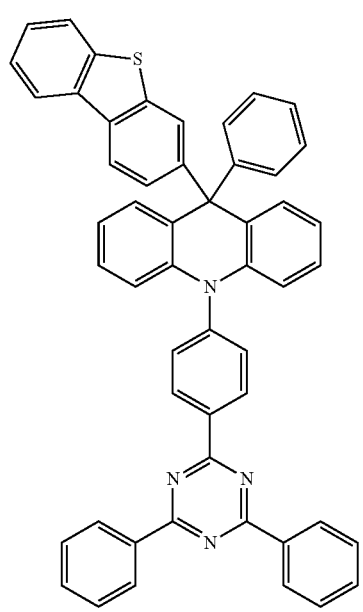
(C-65)
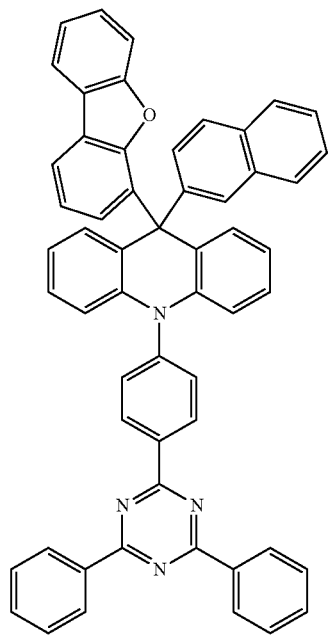
(C-67)
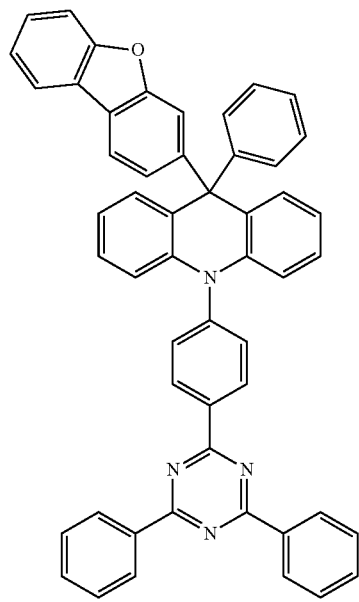
(C-66)
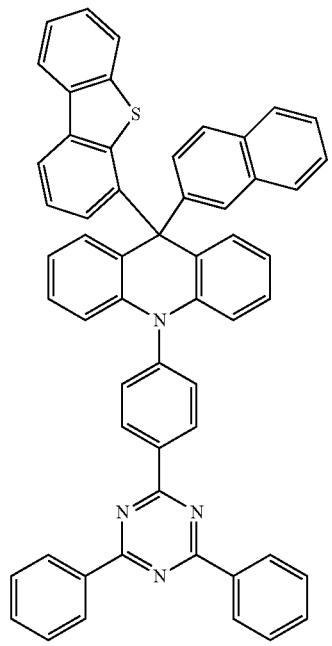
(C-68)

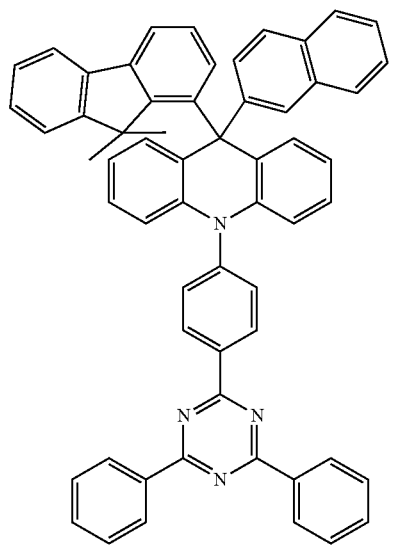 (C-69)
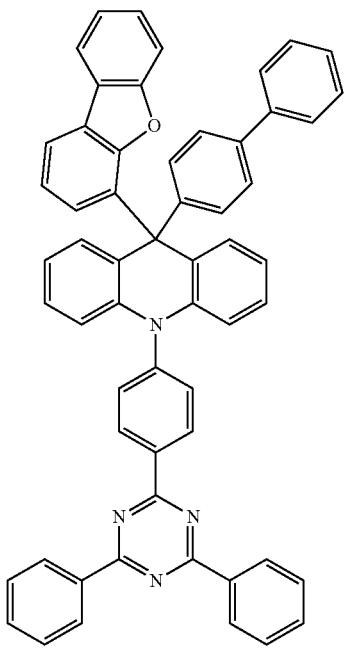 (C-71)
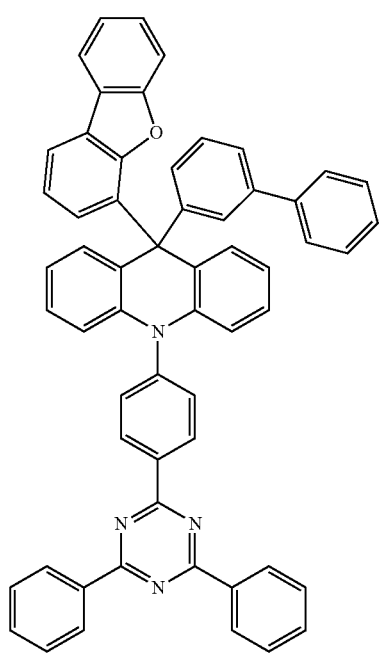 (C-70)
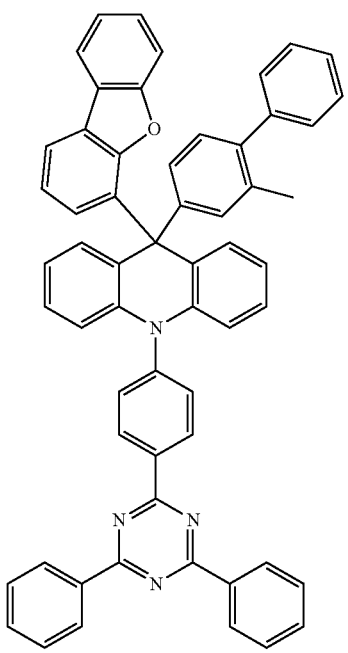 (C-72)

(C-73)
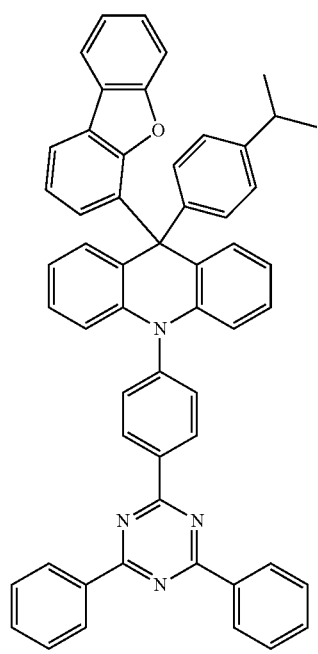
(C-75)
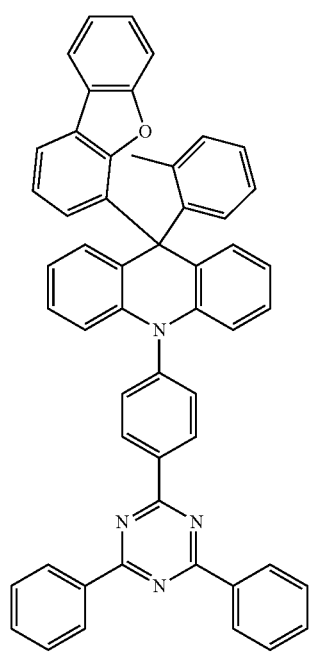
(C-74)
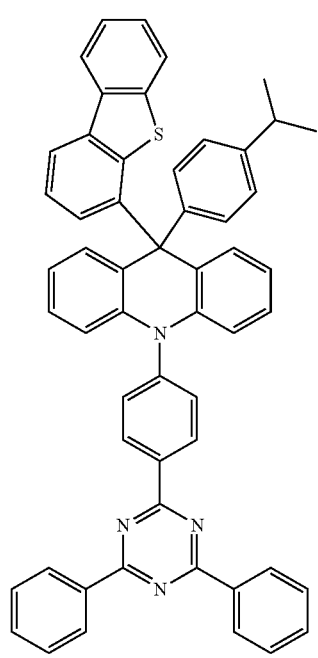
(C-76)
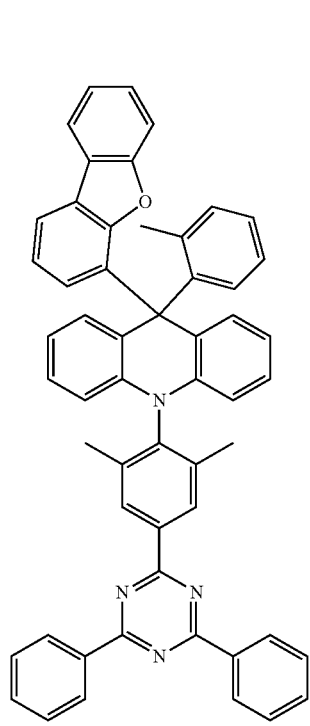

(C-77)
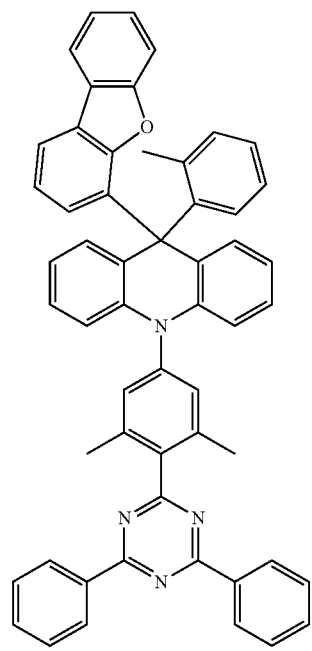
(C-78)
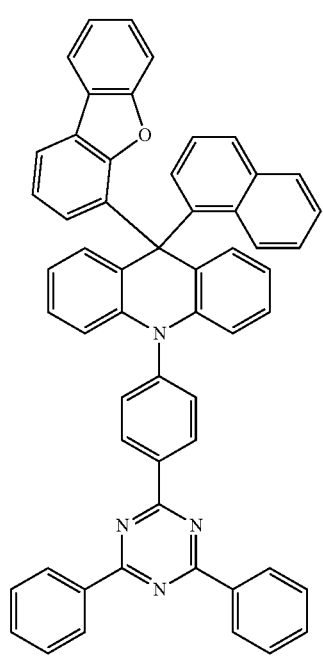
(C-79)
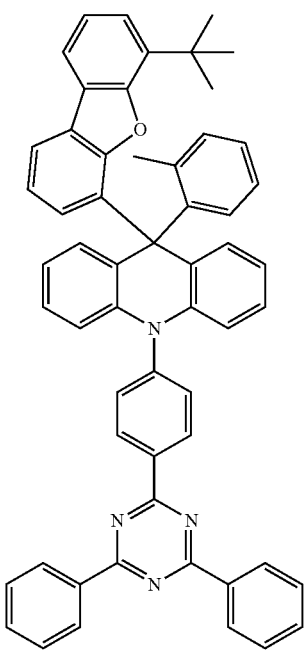
(C-80)
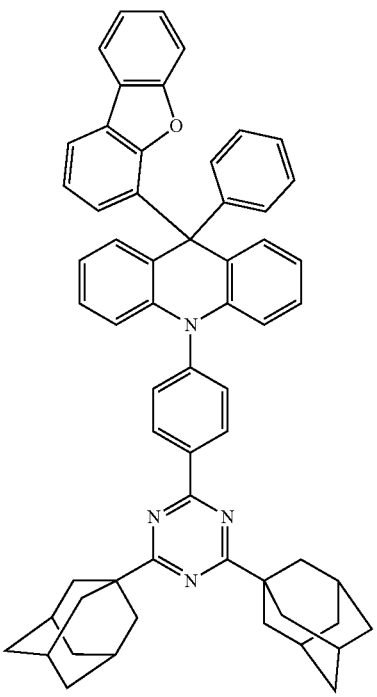

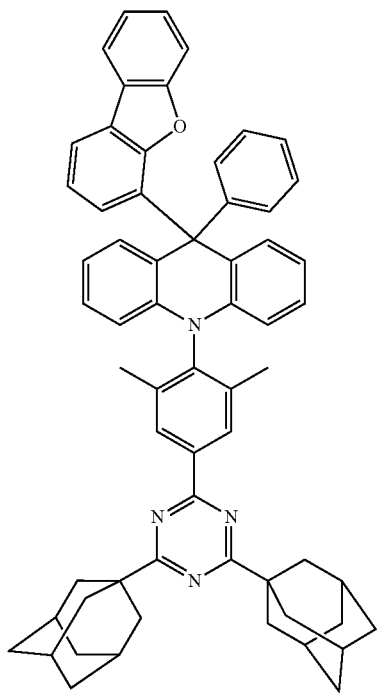
(C-81)
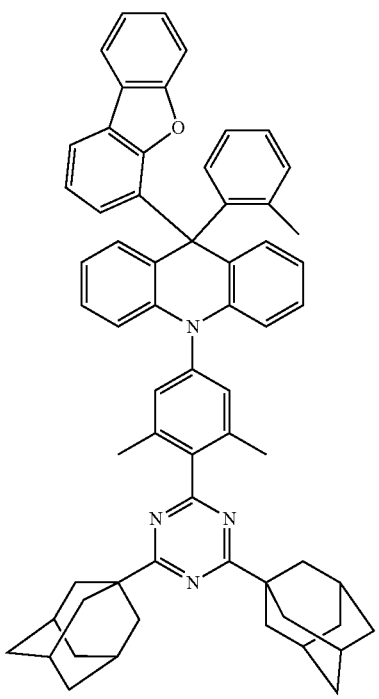
(C-83)
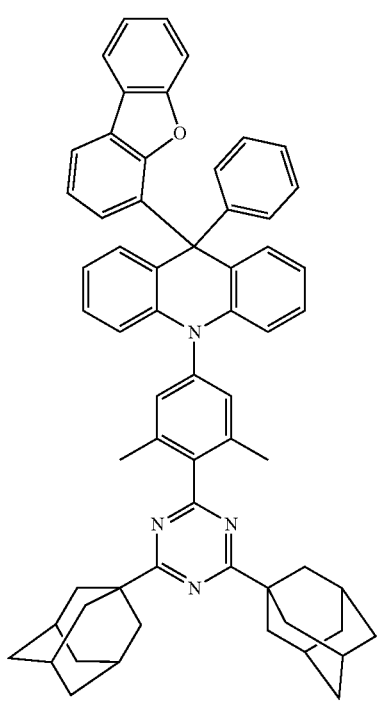
(C-82)
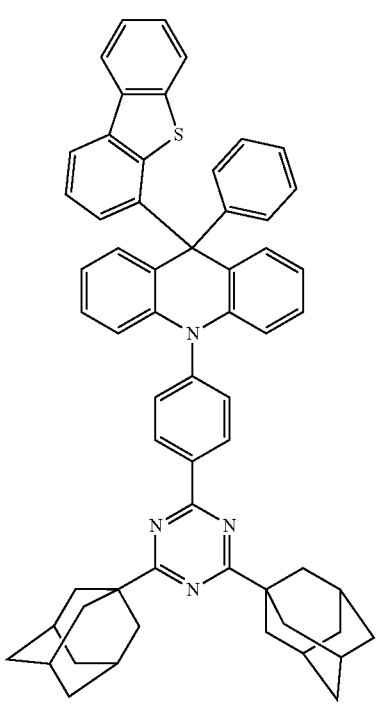
(C-84)

(C-85)
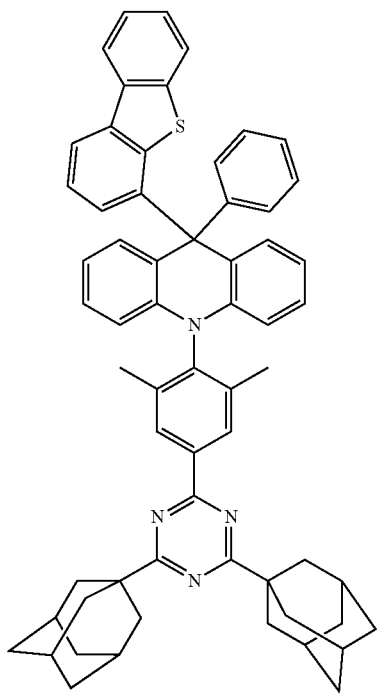
(C-87)
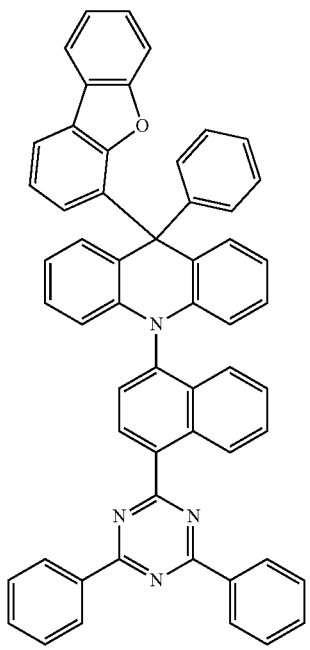
(C-86)
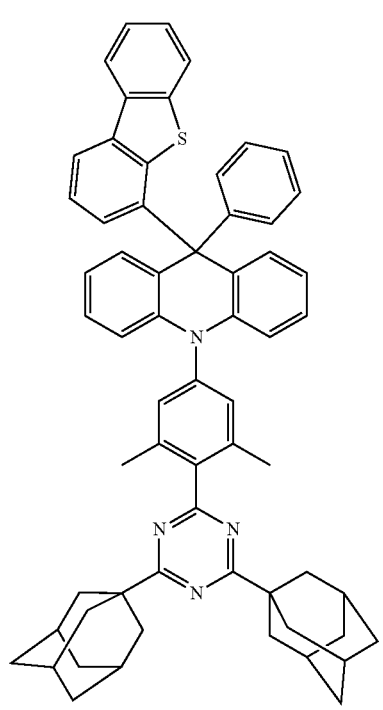
(C-88)
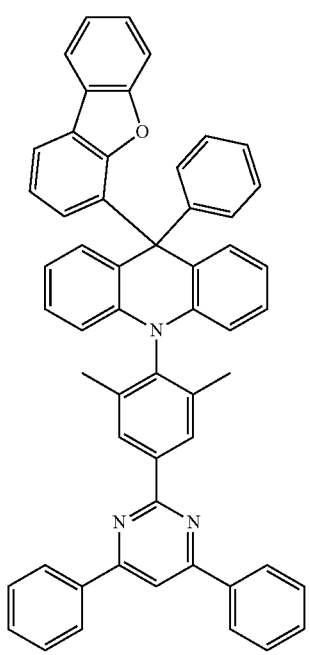

(C-89)
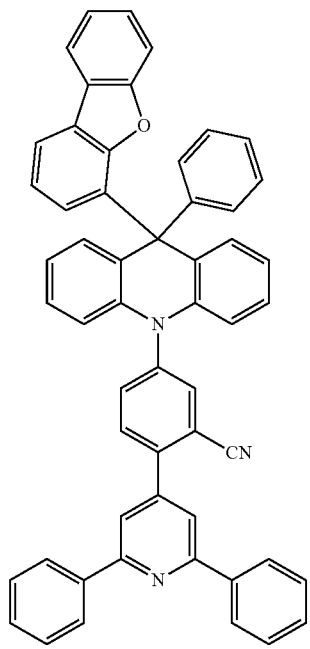
(C-91)
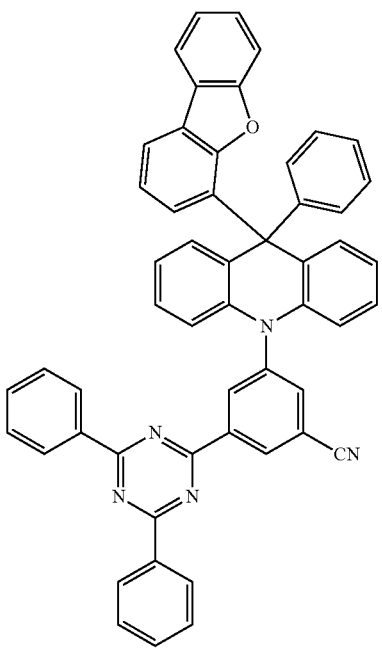
(C-90)
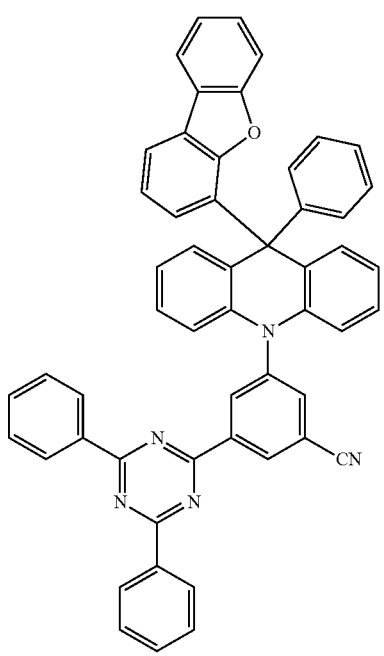
(C-92)
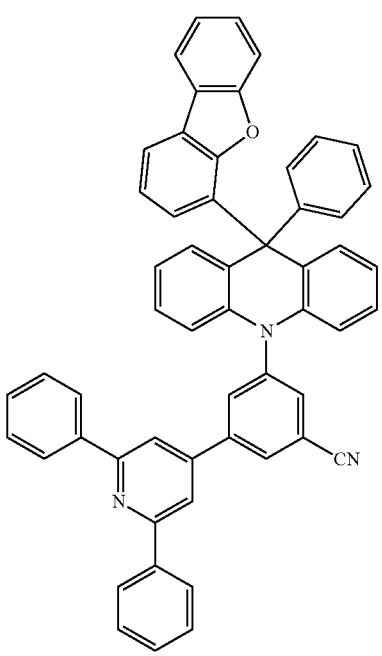

(C-93)
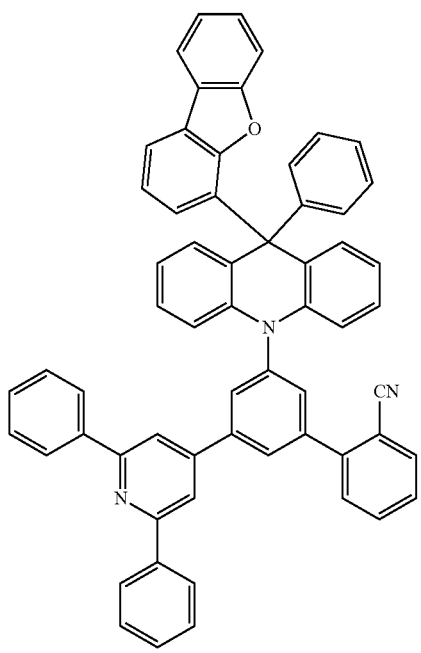
(C-95)
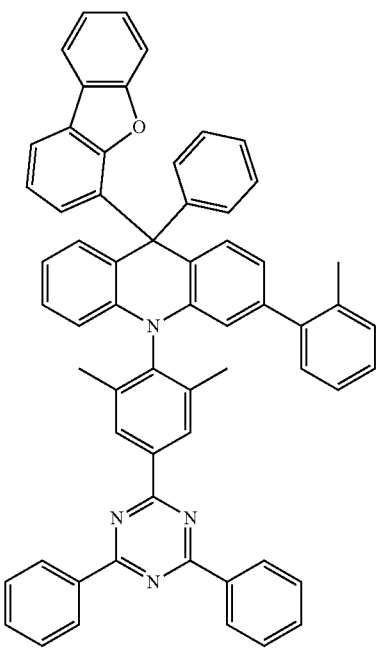
(C-94)
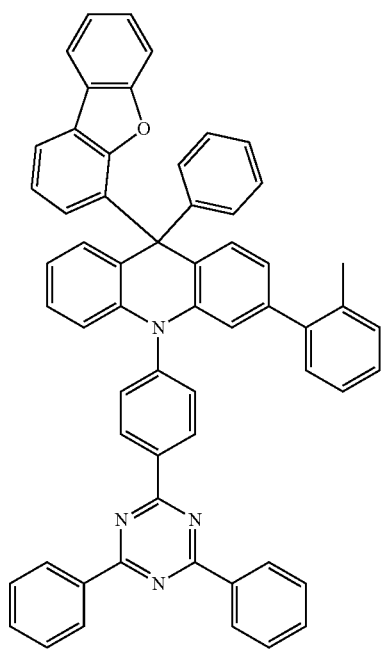
(C-96)
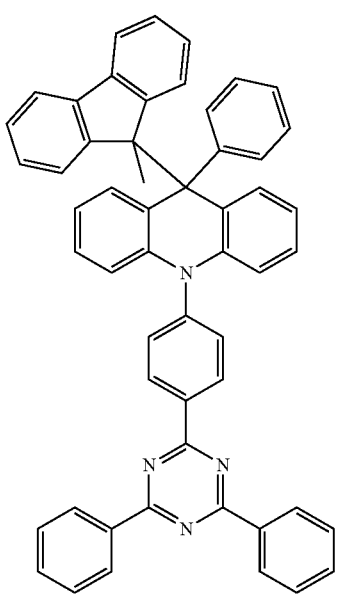

(C-97)

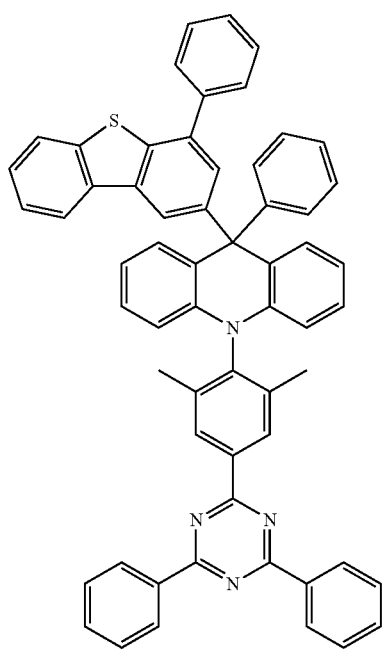

(C-99)

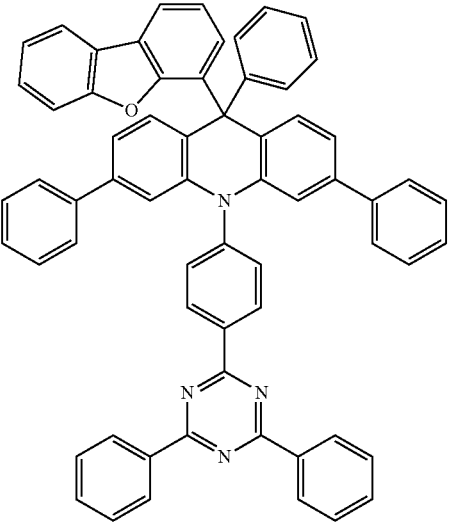

(C-100)

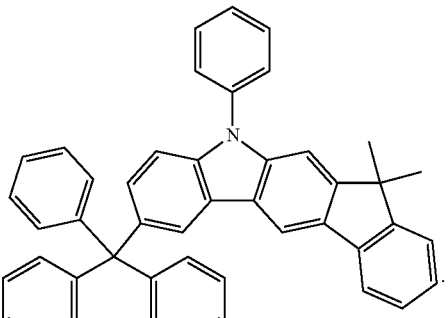

(C-98)

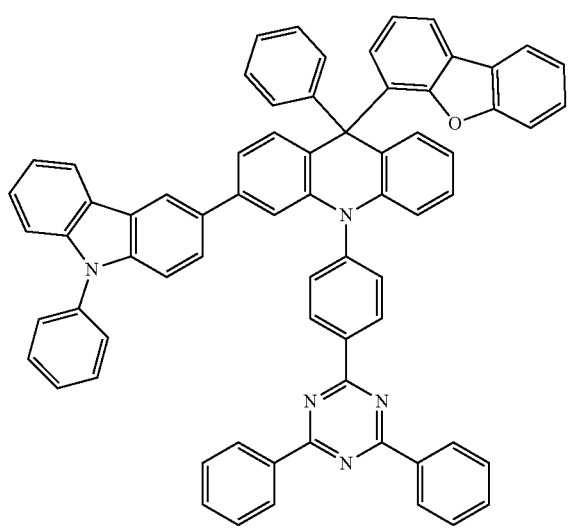

The present invention provides a method for preparing the 9,10-dihydro-acridine derivative. The compound of Formula (I) is synthesized through the following steps:

subjecting a compound of Formula (A) and a compound of Formula (B) as starting materials to a nucleophilic addition reaction, to obtain an intermediate 1; subjecting the intermediate 1 and a compound of Formula (C) to a dehydration-condensation reaction in the presence of Eaton's Reagent, to obtain an intermediate 2; and subjecting the intermediate 2 and a compound of Formula (D) to a coupling reaction in the presence of a catalyst, to obtain the compound of Formula (I);

where the synthesis route for the compound of Formula (I) is shown below:

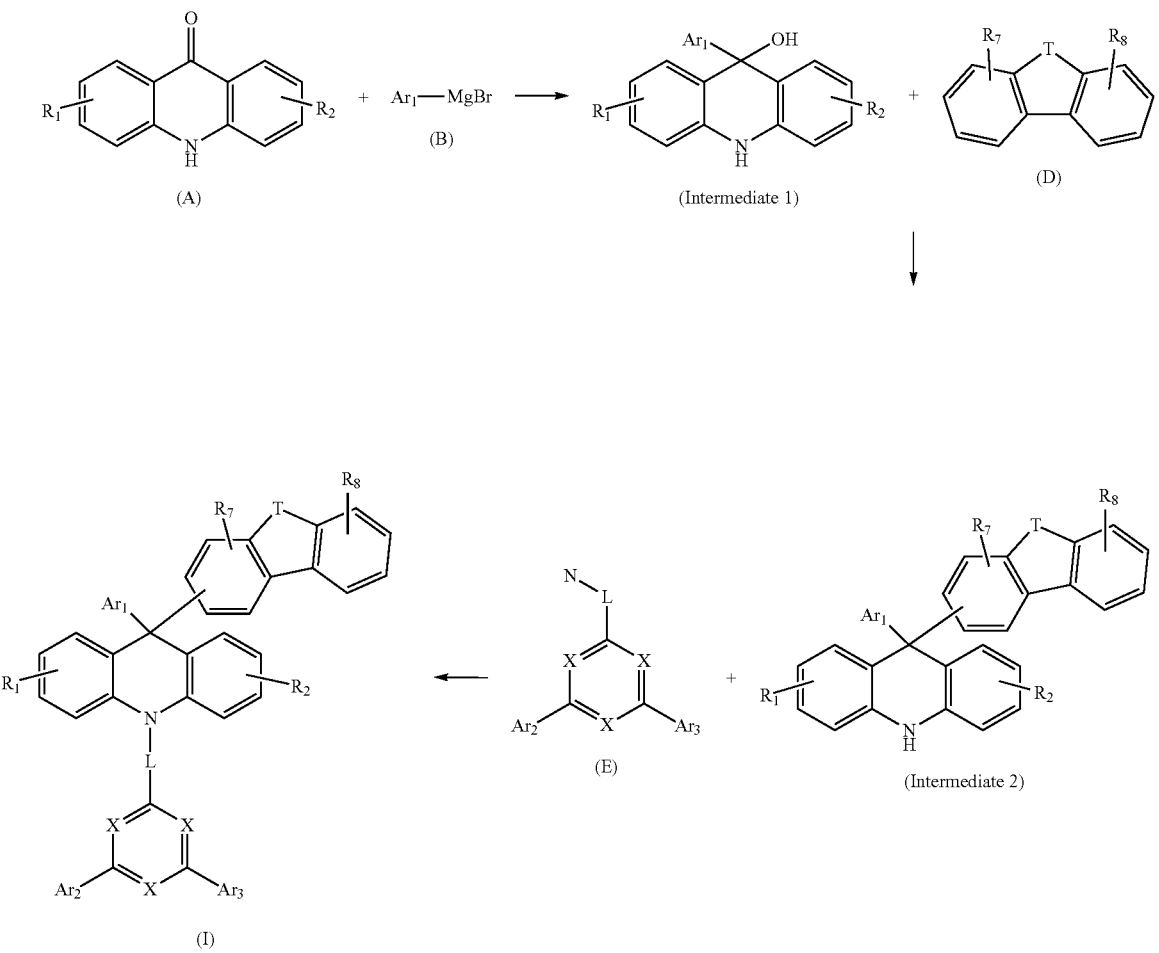

or subjecting the compound of Formula (A) and the compound of Formula (E) as starting materials to a nucleophilic addition reaction, to obtain an intermediate 3; subjecting the intermediate 3 to a nucleophilic substitution reaction, to obtain an intermediate 3'; subjecting the intermediate 3' and a compound of Formula (G) to a Suzuki reaction, to obtain an intermediate 4; and subjecting the intermediate 4 and the compound of Formula (E) to a coupling reaction in the presence of a catalyst, to obtain the compound of Formula (I);

where the synthesis route for the compound of Formula (I) is shown below:

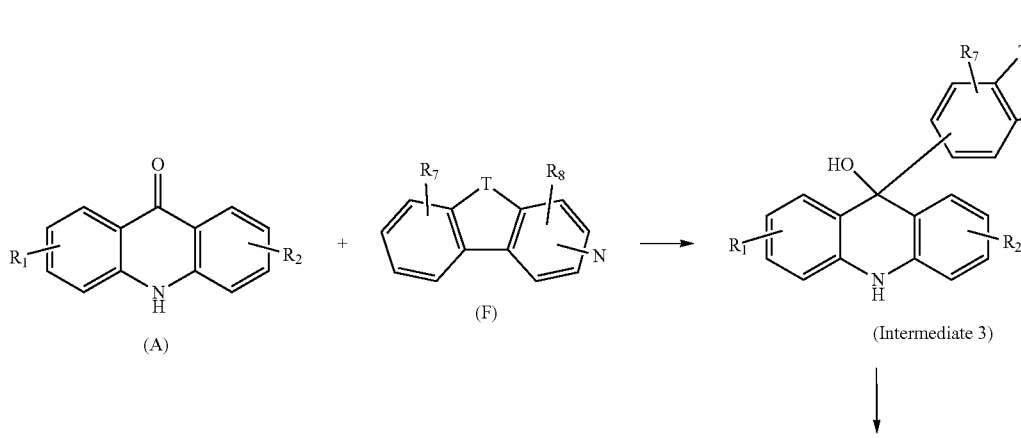

-continued

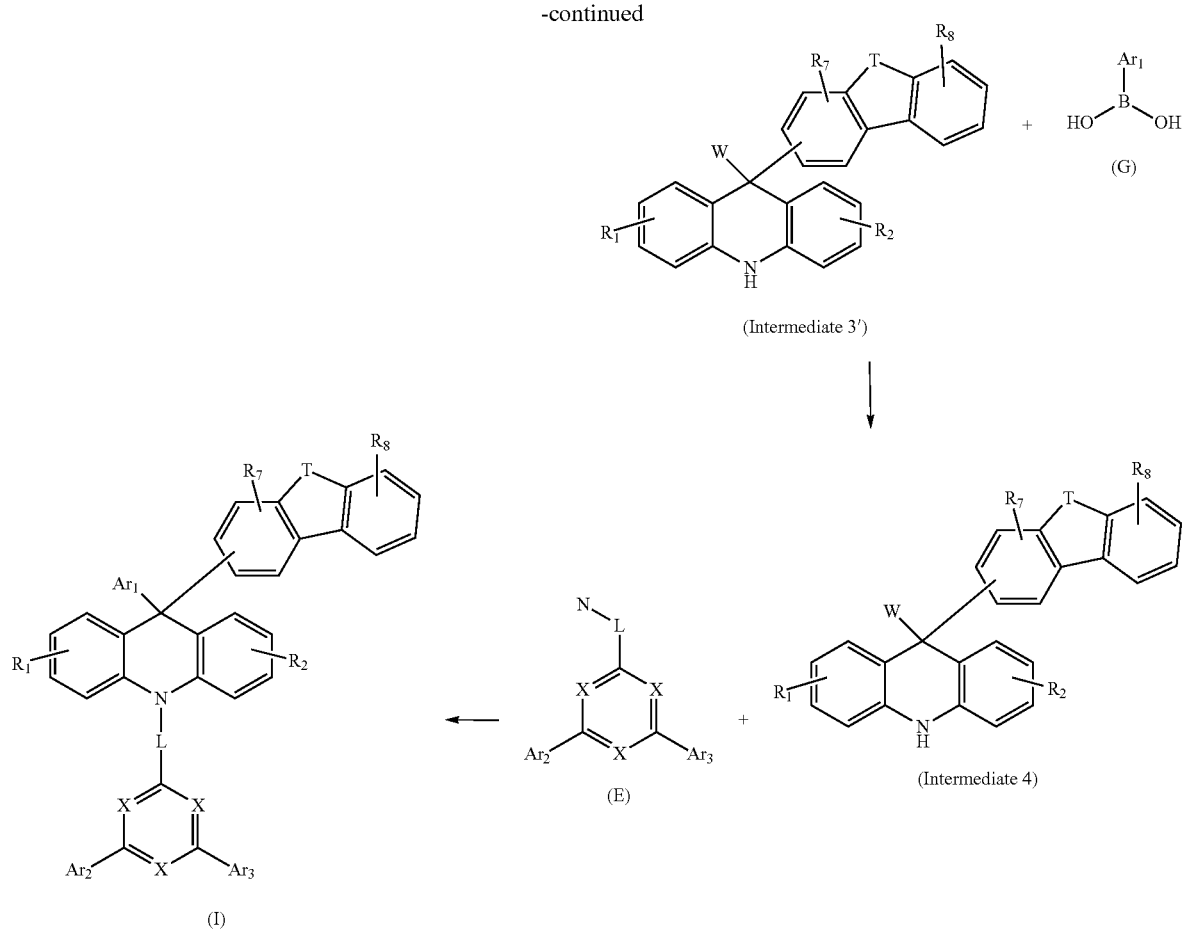

in which N is selected from fluoro, chloro, bromo or iodo, and W is selected from fluoro, chloro, bromo, iodo or triflyl.

The present invention provides use of the 9,10-dihydro-acridine derivative as a thermally activated delayed fluorescent material.

The present invention provides an organic light-emitting device, having at least one functional layer containing a 9,10-dihydro-acridine derivative according to any one of claims 1 to 6.

Optionally, in the organic light-emitting device, the functional layer is a light emitting layer.

Further optionally, the material of the light-emitting layer in the organic light-emitting device comprises a host material and a guest luminescent dye, where the guest luminescent material is the 9,10-dihydro-acridine derivative.

Further optionally, the material of the light emitting layer comprises a host material and a guest luminescent dye, where the host material is the 9,10-dihydro-acridine derivative, and the guest luminescent dye used has thermally activated delayed fluorescence.

The technical solution of the invention has the following advantages.

1. The 9,10-dihydro-acridine derivative provided in the present invention has a structure of Formula (I), and the electron donating group

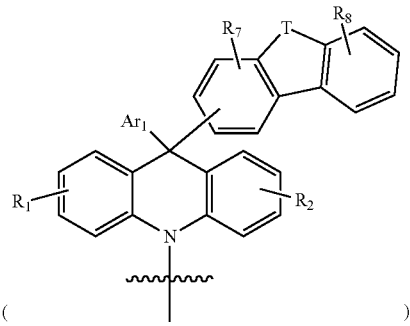

and the electron withdrawing group

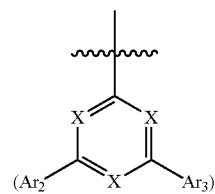

in the 9,10-dihydro-acridine derivative are distributed on different groups, such that the HOMO level distributed on the electron donating group and the LUMO level distributed on the electron withdrawing group are relatively separated, to obtain a small $\Delta E_{ST}$. The HOMO and LUMO levels are appropriately overlapped at the group L, which, together with the rigid twisted structure of the 9,10-dihydro-acridine derivative, allows the compound have a high luminescence efficiency. In the electron donating group of the 9,10-dihydro-acridine derivative, the dihydro-acridinyl group is linked to a dibenzoheterocyclic ring via a σ bond. The introduction of modifying groups via a σ bond allows the further adjustment of the triplet ($T_1$) and singlet ($S_1$) energy levels of the compound, and enables the 9,10-dihydro-acridine derivative to have both a high $S_1$ energy level and a small $\Delta E_{ST}$, thereby achieving the emission in the blue and deep blue regions. As can be known from FIG. 2, the electron donating group formed by connection via a σ bond provided in the present invention has higher singlet and triplet energy levels and smaller $\Delta E_{ST}$ than an electron donating group formed by connection in the form of a spirocyclic ring. As can be known from FIG. 3, compared with the molecule of a TADF material having an electron-donating group formed by connection in the form of a spirocyclic ring, the molecule of the TADF material having an electron-donating group connected by the above σ bond has high singlet and triplet energy levels, and reduced singlet-triplet energy level difference, enabling efficient emission in the blue and deep blue regions. In addition, by connecting the dihydro-acridinyl group and the dibenzoheterocyclic ring by a σ bond, the material molecules have better electron and hole transport rates, and balanced hole and electron transport efficiencies, to further improve the luminescence efficiency of the device.

Moreover, the 9,10-dihydro-acridine derivative of Formula (I) has a high glass transition temperature, high thermal stability and morphological stability, and excellent film forming performance, and is not prone to crystallization when used as a host material in the light emitting layer, thus facilitating the improvement of the performance and luminescence efficiency of the OLED device.

The 9,10-dihydro-acridine derivative, as a new thermally activated delayed fluorescent material promotes the conversion of triplet ($T_1$) excitons into singlet ($S_1$) excitons by reverse intersystem crossing (RISC) due to the small $\Delta E_{ST}$, and then the $S_1$ excitons undergo radiation transition to fluoresce, achieving a theoretical internal quantum efficiency of 100%. In addition, by designing the intramolecular connection mode of the dihydro-acridridyl group and the dibenzoheterocyclic ring by a σ bond, emission in the blue and deep blue regions is realized, and a blue light-emitting TADF material molecule with high luminescence efficiency is obtained. Moreover, the blue light-emitting TADF material molecule has good thermal stability and relatively balanced electron and hole transport efficiencies. When the 9,10-dihydro-acridine derivative is used as a fluorescent material in an OLED device, high blue light emitting efficiency of the device can be achieved, and a high external quantum efficiency is attained.

2. In the 9,10-dihydro-acridine derivative provided in the present invention, by further adjusting the substituents R1-R8 and Ar1-Ar3, the electron-donating group and the electron withdrawing group in the material molecule can be further adjusted, thereby further improving the hole and electron transport performance of the material molecule, and improving the balance in charge transport. In addition, the singlet energy level of the material molecule can be further increased and a small ΔEst is maintained, thereby enhancing the luminescence efficiency of the 9,10-dihydro-acridine derivative as a blue light emitting material. Moreover, by configuring the substituent groups to adjust the electron donating and withdrawing groups, the distribution of the LUMO level or the HOMO level becomes more uniform, so the HOMO and LUMO levels are further optimized.

3. The preparation method of the 9,10-dihydro-acridine derivative provided in the present invention has the advantages of readily available starting materials, mild reaction conditions, and simple operation steps, so a simple and easy-to-implement preparation method is provided for the mass production of the above 9,10-dihydro-acridine derivative.

4. The organic light-emitting device provided in the present invention has at least one functional layer containing the 9,10-dihydro-acridine derivative. The functional layer is a light emitting layer.

When used as a guest luminescent dye in the light emitting layer, the thermally activated delayed fluorescence of the 9,10-dihydro-acridine derivative enables the triplet excitons of the material molecule to be converted into singlet excitons, and the singlet excitons fluoresce with a high luminescence efficiency. Moreover, the 9,10-dihydro-acridine derivative can achieve high-efficiency emission in blue and deep blue regions, which facilitates the obtaining of a blue organic light-emitting device with high luminescence efficiency, so as to solve the problem of low luminescence efficiency of blue OLED devices due to the high blue light energy.

In addition, when the 9,10-dihydro-acridine derivative is used as a host material in the light emitting layer, the host material has ambipolarity and narrow energy gap, which facilitates the recombination of electrons and holes in the host material, enlarges the recombination region, and thus reduces the exciton concentration, thereby effectively reducing the exciton quenching, and solving the problem of low efficiency and short service life due to exciton quenching. In addition, compared with a conventional host material, the high inter-system crossing (RISC) rate of conversion from $T_1$ to $S_1$ of the 9,10-dihydro-acridine derivative as a host material can inhibit the Dexter energy transfer (DET) from the host material to the luminescent dye, promotes the FÖrster energy transfer, increase the proportion of singlet excitons, and suppress the triplet excitons, thereby greatly reducing the exciton loss due to Dexter energy transfer (DET), effectively reducing the efficiency roll-off of the organic light-emitting device, and improving the external quantum efficiency of the device.

BRIEF DESCRIPTION OF THE DRAWINGS

In order to more clearly explain the technical solutions in the specific embodiments of the present invention or in the prior art, the drawings used in the description of the specific embodiments or the prior art will be briefly described below.

Obviously, the drawings depicted below are merely some embodiments of the present invention, and those skilled in the art can obtain other drawings based on these drawings without any creative efforts.

LIST OF REFERENCE NUMERALS

Figure 1:
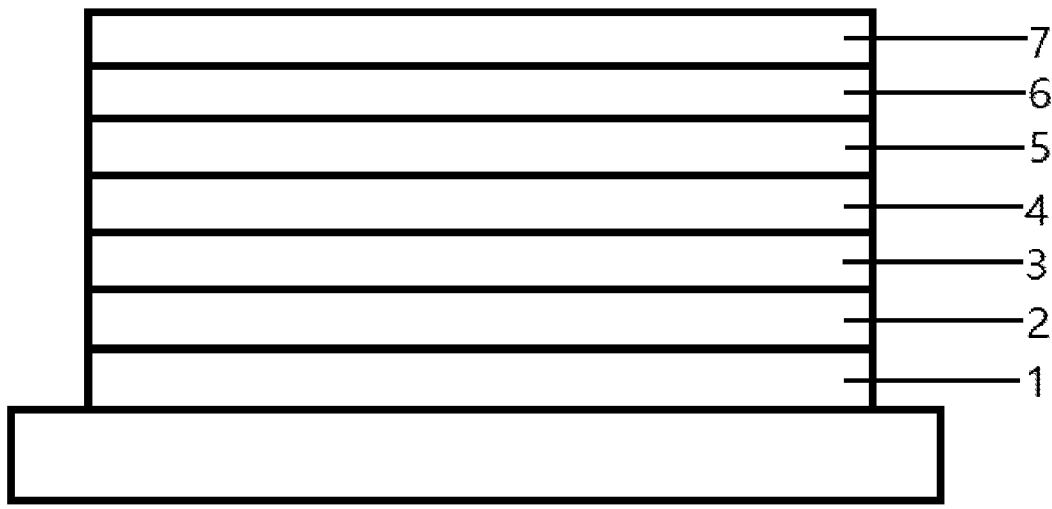
FIG. 1 is a schematic structural view of an organic light-emitting device according to Examples 67 to 77 and Comparative Examples 1 and 2 of the present invention.

1-anode, 2-hole injection layer, 3-hole transport layer, 4-light emitting layer, 5-electron transport layer, 6-electron injection layer, 7-cathode.

DETAILED DESCRIPTION

The technical solutions of the present invention will be described clearly and fully with reference to the accompanying drawings. Apparently, the embodiments described are some preferred embodiments, rather than all of the embodiments of the present invention. All other embodiments obtained by a person of ordinary skill in the art without creative efforts based on the embodiments of the present invention shall fall within the protection scope of the present invention.

It is to be understood that in the description of the present invention, the terms "first" and "second" are used herein for purposes of description, and are not intended to indicate or imply relative importance.

The present invention can be embodied in many different forms and is not limited to the embodiments described herein. Conversely, these embodiments are provided for the purpose of making the disclosure of the present invention more thorough and comprehensive and conveying the concept of the present invention fully to those skilled in the art, and the scope of the present invention is defined merely by the claims. In the figures, for the sake of clarity, the dimensions and relative dimensions of the layers and regions will be exaggerated. It should be understood that when an element, for example, a layer, is referred to as being "formed" or "disposed" "on" another element, the element may be directly disposed on the other element or an intervening element may be present. Conversely, when an element is referred to as being "directly formed on" or "directly disposed on" another element, no intervening element is present.

Example 1

This example provides a 9,10-dihydro-acridine derivative having a structure of Formula C-1:

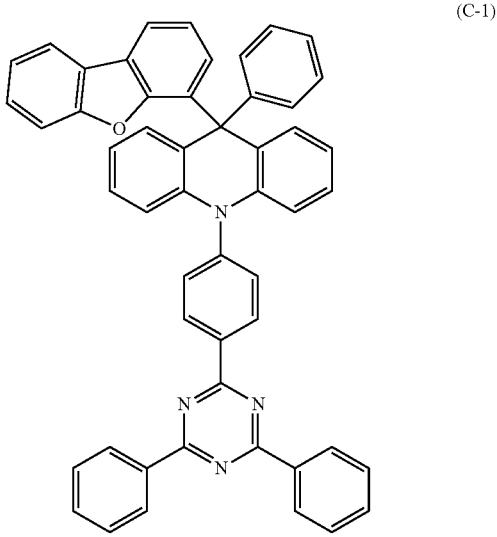 [SMILES: c1ccc(-c2nc(-c3ccccc3)nc(-c3ccc(N4c5ccccc5C(c5ccccc5)(c5cccc6c5oc5ccccc56)c5ccccc54)cc3)n2)cc1]

(C-1)

The synthesis route for the 9,10-dihydro-acridine derivative of Formula C-1 is shown below:

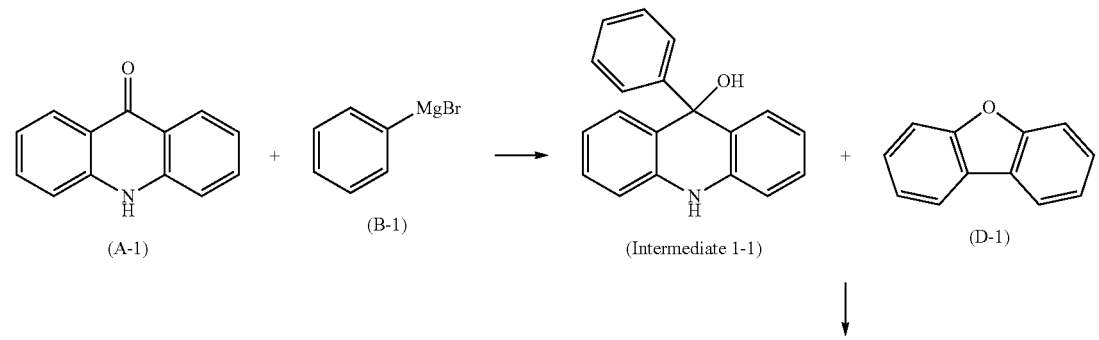

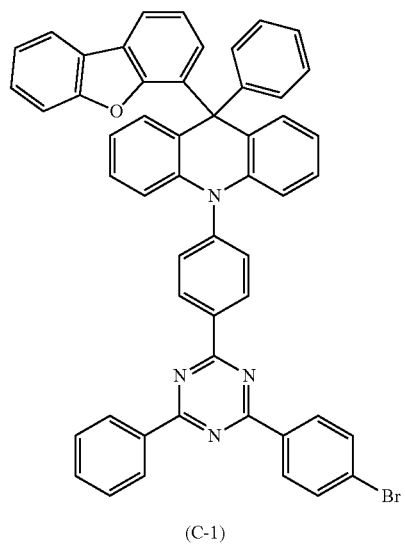

(C-1)

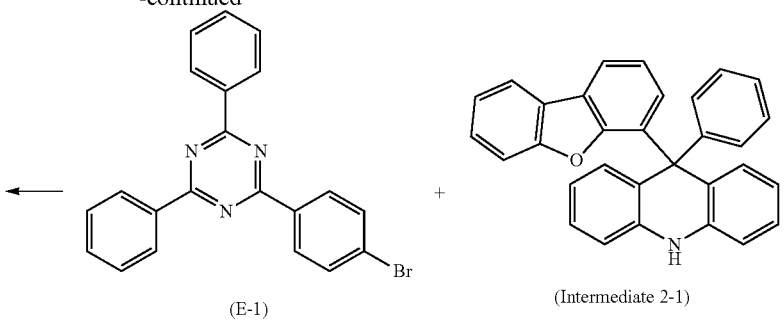

(E-1)

(Intermediate 2-1)

The method for preparing the 9,10-dihydro-acridine derivative of Formula C-1 comprises specifically the following steps.

(1) Synthesis of Intermediate 1-1

Under nitrogen atmosphere, 9(10H)-acridone (the compound A-1) (19.5 g, 100 mmol) and tetrahydrofuran (700 mL) were added to a 1 L three-neck flask. A phenyl magnesium bromide (the compound B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the Intermediate 1-1 as a solid (24 g, yield: 88%);

(2) Synthesis of Intermediate 2-1

Under nitrogen atmosphere, the compound 1-1 (22.0 g, 80 mmol), dibenzofuran (the compound D-1) (27 g, 160 mmol), and dichloromethane (600 mL) were added to a 1 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the intermediate 2-1 as a solid (13.5 g, yield: 40%).

(3) Synthesis of 9,10-dihydro-acridine Derivative C-1

Under nitrogen atmosphere, the intermediate 2-1 (8 g, 20 mmol), palladium diacetate (0.13 g, 0.6 mmol), tri-tert-butylphosphine (0.45 g, 2.2 mmol), the compound E-1 (8.5 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-1 (12.0 g, yield 82%).

Element analysis: (C52H34N4O) calculated: C, 85.46; H, 4.69; N, 7.67; O, 2.19. found: C, 85.49; H, 4.71; N, 7.66; O, 2.14, HRMS (ESI) m/z (M+): calculated: 730.2732. found: 730.2745.

Example 2

This example provides a 9,10-dihydro-acridine derivative having a structure of Formula C-2:

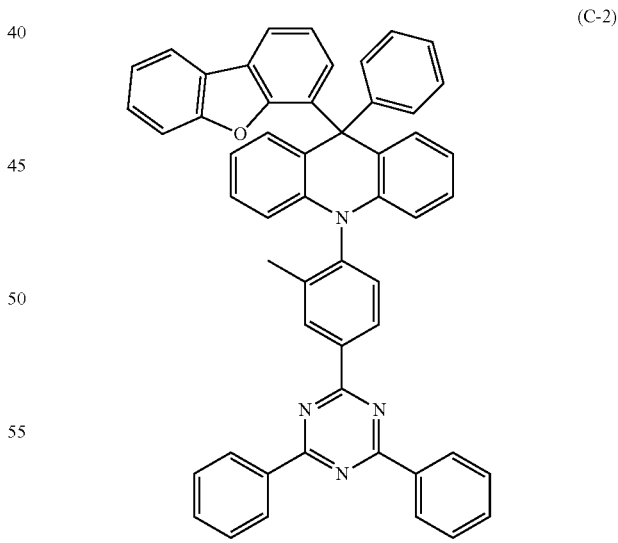

(C-2)

The preparation steps of the 9,10-dihydro-acridine derivative of Formula C-2 were the same as those for the 9,10-dihydro-acridine derivative of Formula C-1 provided in Example 1, except that:

the compound E-1 in Step (3) of Example 1 was replaced by the compound of Formula E-2. The yield was 80%.

Example 3

This example provides a 9,10-dihydro-acridine derivative having a structure of Formula C-3:

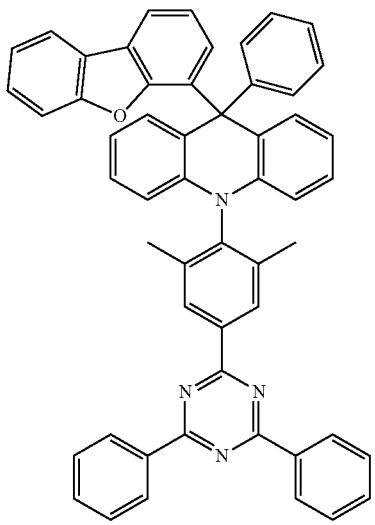

(C-3)

The preparation steps of the 9,10-dihydro-acridine derivative of Formula C-3 were the same as those for the 9,10-dihydro-acridine derivative of Formula C-1 provided in Example 1, except that:

the compound E-1 in Step (3) of Example 1 was replaced by the compound of Formula E-3. The yield was 78%.

Example 4

This example provides a 9,10-dihydro-acridine derivative having a structure of Formula C-4:

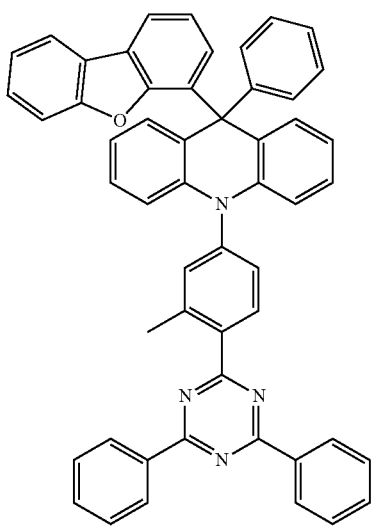

(C-4)

The preparation steps of the 9,10-dihydro-acridine derivative of Formula C-4 were the same as those for the 9,10-dihydro-acridine derivative of Formula C-1 provided in Example 1, except that:

the compound E-1 in Step (3) of Example 1 was replaced by the compound of Formula E-4. The yield was 85%.

Example 5

This example provides a 9,10-dihydro-acridine derivative having a structure of Formula C-5:

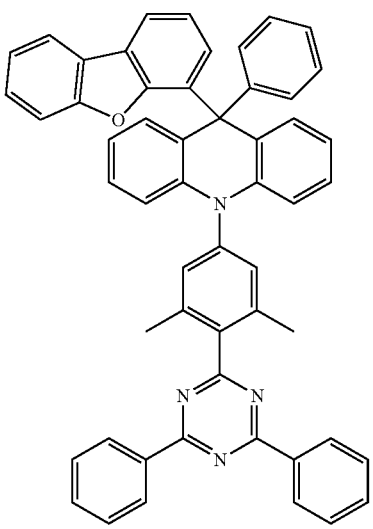

(C-5)

The preparation steps of the 9,10-dihydro-acridine derivative of Formula C-5 were the same as those for the 9,10-dihydro-acridine derivative of Formula C-1 provided in Example 1, except that:

the compound E-1 in Step (3) of Example 1 was replaced by the compound of Formula E-5. The yield was 84%.

Example 6

This example provides a 9,10-dihydro-acridine derivative having a structure of Formula C-6:

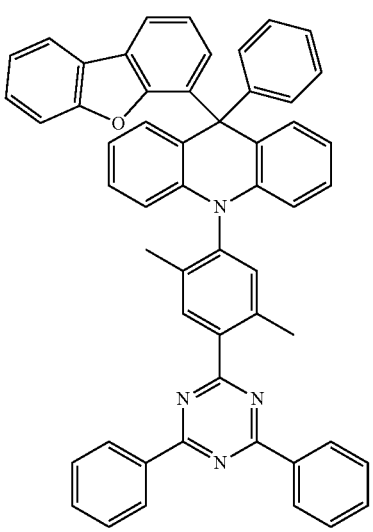

(C-6)

The preparation steps of the 9,10-dihydro-acridine derivative of Formula C-6 were the same as those for the 9,10-dihydro-acridine derivative of Formula C-1 provided in Example 1, except that:

the compound E-1 in Step (3) of Example 1 was replaced by the compound of Formula E-6. The yield was 77%.

Example 7

This example provides a 9,10-dihydro-acridine derivative having a structure of Formula C-7:

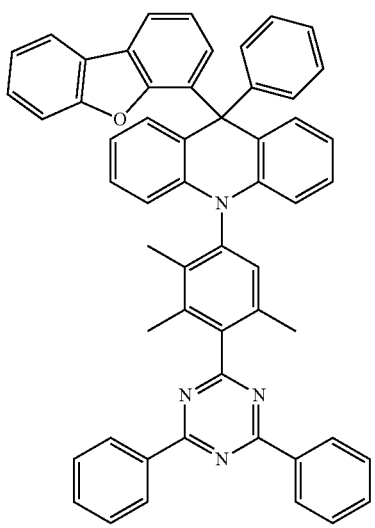

(C-7)

The preparation steps of the 9,10-dihydro-acridine derivative of Formula C-7 were the same as those for the 9,10-dihydro-acridine derivative of Formula C-1 provided in Example 1, except that:

the compound E-1 in Step (3) of Example 1 was replaced by the compound of Formula E-7. The yield was 79%.

Example 8

This example provides a 9,10-dihydro-acridine derivative having a structure of Formula C-8:

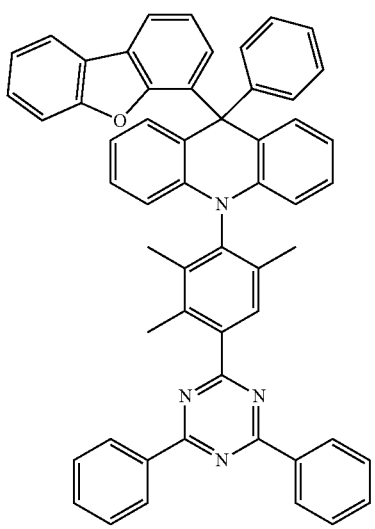

(C-8)

The preparation steps of the 9,10-dihydro-acridine derivative of Formula C-8 were the same as those for the 9,10-dihydro-acridine derivative of Formula C-1 provided in Example 1, except that:

the compound E-1 in Step (3) of Example 1 was replaced by the compound of Formula E-8. The yield was 75%.

Example 9

This example provides a 9,10-dihydro-acridine derivative having a structure of Formula C-9:

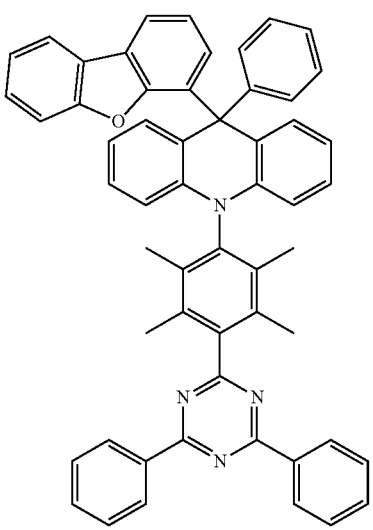

(C-9)

The preparation steps of the 9,10-dihydro-acridine derivative of Formula C-9 were the same as those for the 9,10-dihydro-acridine derivative of Formula C-1 provided in Example 1, except that:

the compound E-1 in Step (3) of Example 1 was replaced by the compound of Formula E-9. The yield was 73%.

The structures of the compounds E-2, E-3, E-4, E-5, E-6, E-7, E-8, and E-9 are shown below:

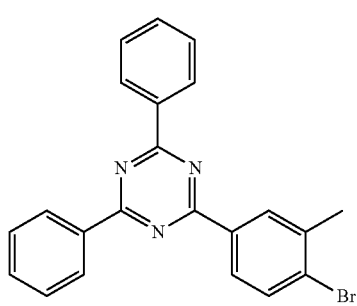

(E-2)

(E-3)
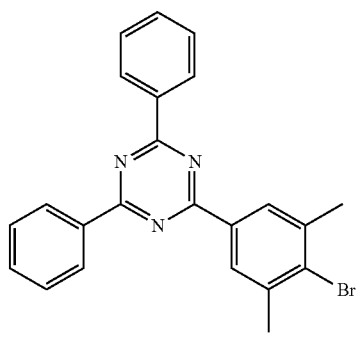
(E-4)
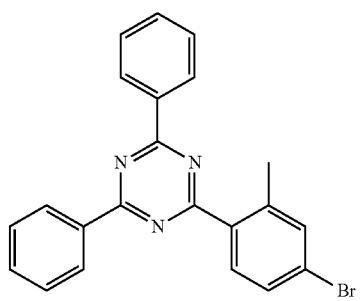
(E-5)
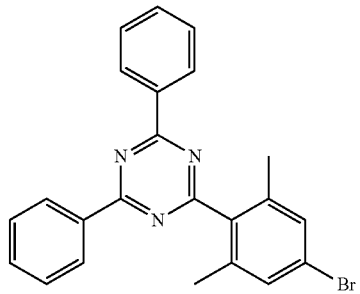
(E-6)
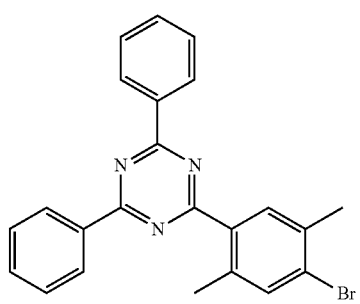
(E-7)
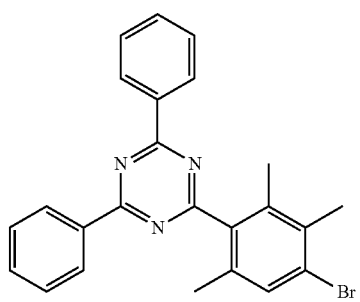
(E-8)
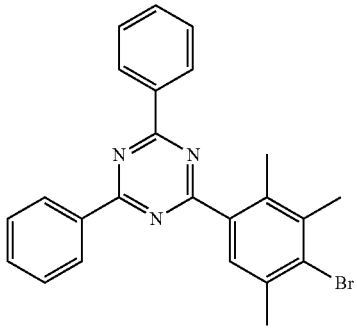
(E-9)
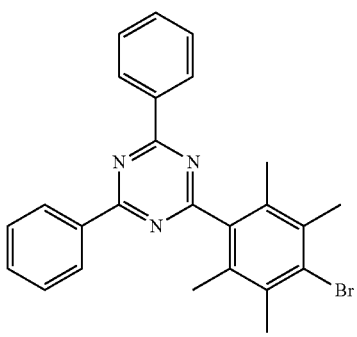
Example 10
This example provides a 9,10-dihydro-acridine derivative having a structure of Formula C-10:
(C-10)
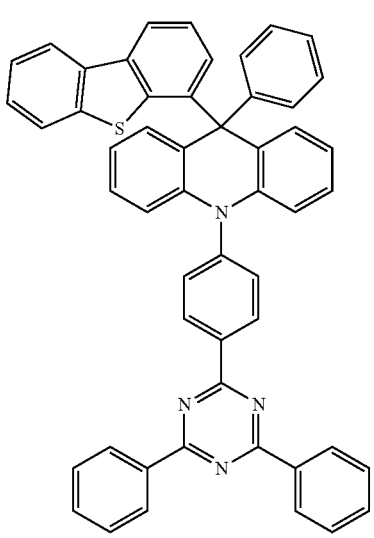
The synthesis route for the 9,10-dihydro-acridine derivative of Formula C-10 is shown below:

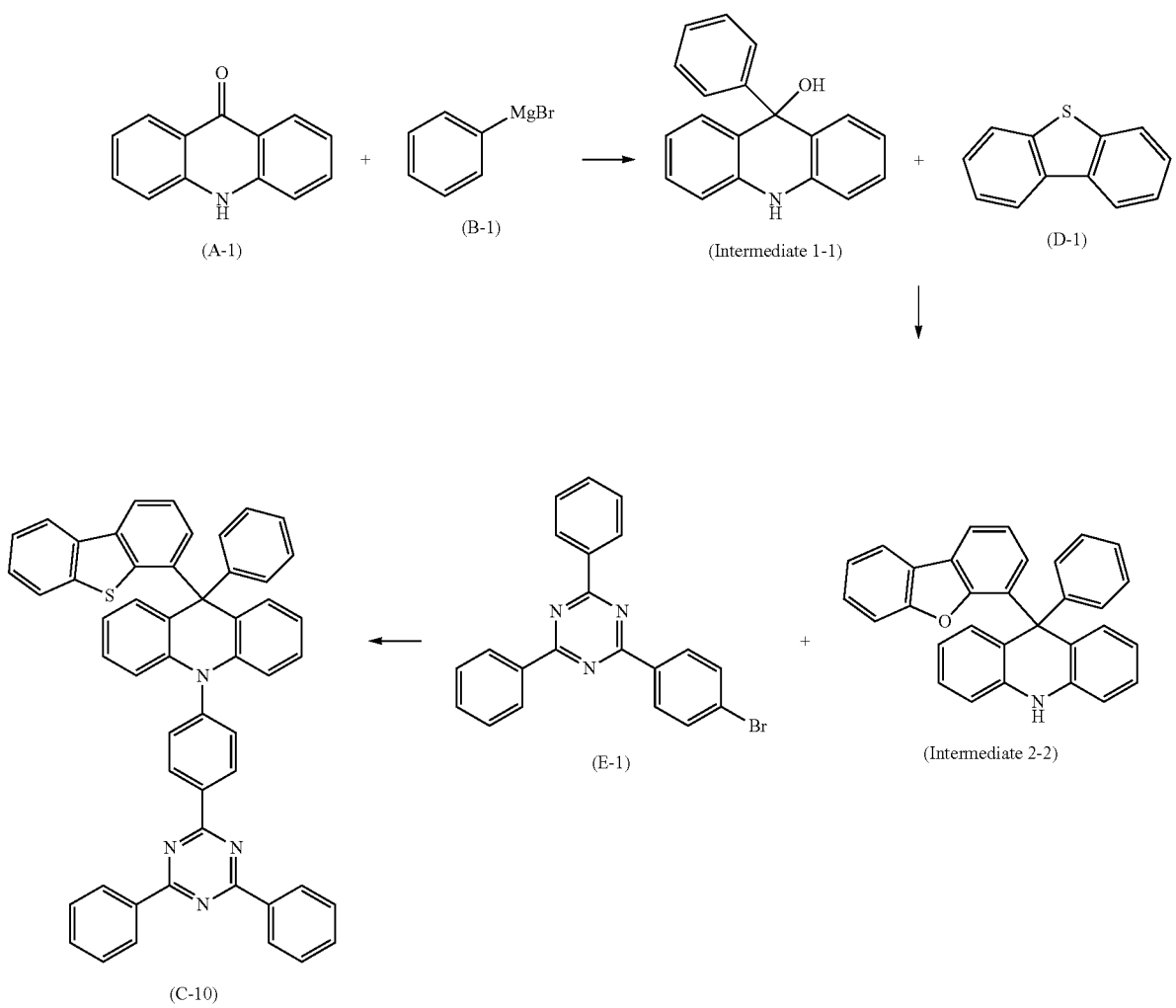

The method for preparing the 9,10-dihydro-acridine derivative of Formula C-1 comprises specifically the following steps.

(1) Synthesis of Intermediate 1-1

Under nitrogen atmosphere, 9(10H)-acridone (the compound A-1) (19.5 g, 100 mmol) and tetrahydrofuran (700 mL) were added to a 1 L three-neck flask. A phenyl magnesium bromide (the compound B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the solid compound 1-1 (24 g, yield: 88%).

(2) Synthesis of Intermediate 2-2

Under nitrogen atmosphere, the compound 1-1 (22.0 g, 80 mmol), dibenzothiophene (the compound D-2) (29 g, 160 mmol), and dichloromethane (600 mL) were added to a 1 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the solid compound 1-3 (13.3 g).

(3) Synthesis of 9,10-dihydro-acridine Derivative C-10

Under nitrogen atmosphere, the compound 2-2 (8.8 g, 20 mmol), palladium diacetate (0.13 g, 0.6 mmol), tri-tert-butylphosphine (0.45 g, 2.2 mmol), the compound E-1 (8.5 g 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-10 (12.5 g, yield 83%).

Element analysis: (C52H34N4S) calculated: C, 83.62; H, 4.59; N, 7.50; S, 4.29. found: C, 83.60; H, 4.61; N, 7.47; S, 4.33, HRMS (ESI) m/z (M+): calculated: 746.2504. found: 746.2521.

Example 11

This example provides a 9,10-dihydro-acridine derivative having a structure of Formula C-11:

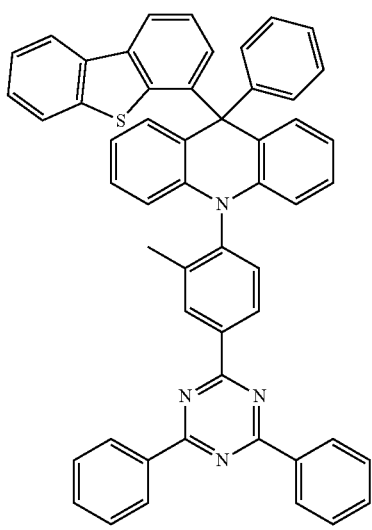
(C-11)

The preparation steps of the 9,10-dihydro-acridine derivative of Formula C-11 were the same as those for the 9,10-dihydro-acridine derivative of Formula C-10 provided in Example 10, except that:
the compound E-1 in Step (3) of Example 10 was replaced by the compound of Formula E-2. The yield was 81%.

Example 12

This example provides a 9,10-dihydro-acridine derivative having a structure of Formula C-12:

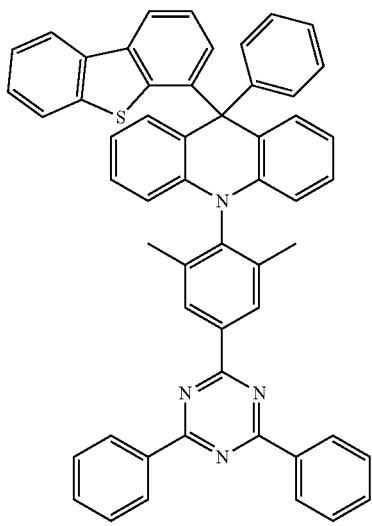
(C-12)

The preparation steps of the 9,10-dihydro-acridine derivative of Formula C-12 were the same as those for the 9,10-dihydro-acridine derivative of Formula C-10 provided in Example 10, except that:
the compound E-1 in Step (3) of Example 10 was replaced by the compound of Formula E-3. The yield was 78%.

Example 13

This example provides a 9,10-dihydro-acridine derivative having a structure of Formula C-13:

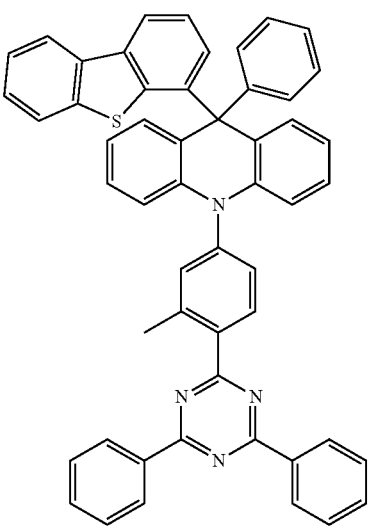
(C-13)

The preparation steps of the 9,10-dihydro-acridine derivative of Formula C-13 were the same as those for the 9,10-dihydro-acridine derivative of Formula C-10 provided in Example 10, except that:
the compound E-1 in Step (3) of Example 10 was replaced by the compound of Formula E-4. The yield was 86%.

Example 14

This example provides a 9,10-dihydro-acridine derivative having a structure of Formula C-14:

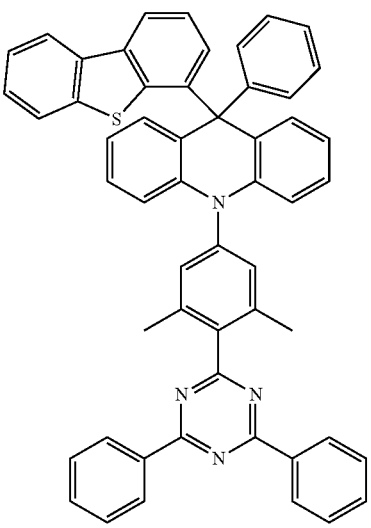
(C-14)

The preparation steps of the 9,10-dihydro-acridine derivative of Formula C-14 were the same as those for the 9,10-dihydro-acridine derivative of Formula C-10 provided in Example 10, except that:
the compound E-1 in Step (3) of Example 10 was replaced by the compound of Formula E-5. The yield was 83%.

Example 15

This example provides a 9,10-dihydro-acridine derivative having a structure of Formula C-15:

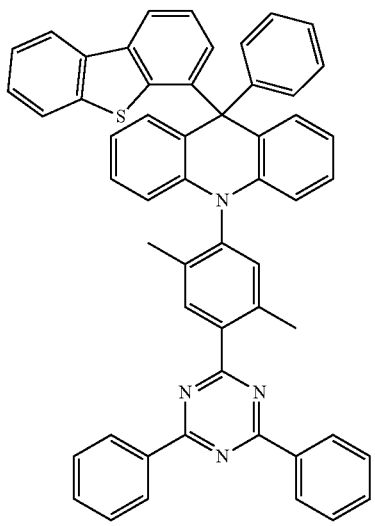

(C-15)

The preparation steps of the 9,10-dihydro-acridine derivative of Formula C-15 were the same as those for the 9,10-dihydro-acridine derivative of Formula C-10 provided in Example 10, except that:
the compound E-1 in Step (3) of Example 10 was replaced by the compound of Formula E-6. The yield was 79%.

Example 16

This example provides a 9,10-dihydro-acridine derivative having a structure of Formula C-16:

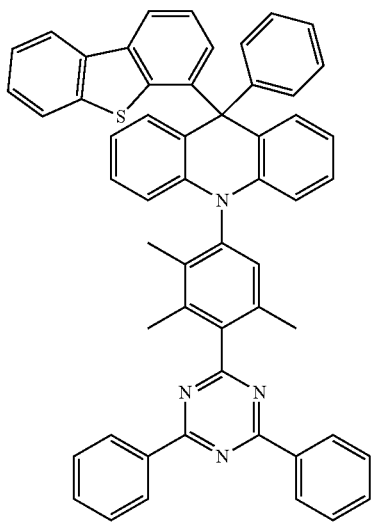

(C-16)

The preparation steps of the 9,10-dihydro-acridine derivative of Formula C-16 were the same as those for the 9,10-dihydro-acridine derivative of Formula C-10 provided in Example 10, except that:
the compound E-1 in Step (3) of Example 10 was replaced by the compound of Formula E-7. The yield was 79%.

Example 17

This example provides a 9,10-dihydro-acridine derivative having a structure of Formula C-17:

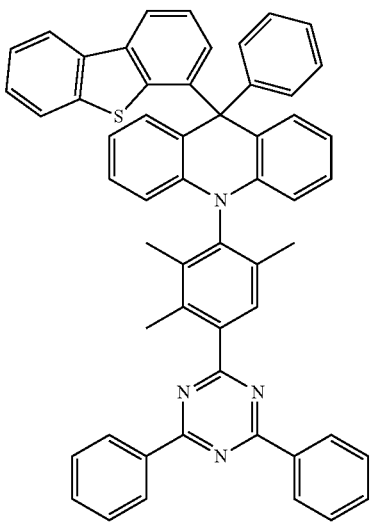

(C-17)

The preparation steps of the 9,10-dihydro-acridine derivative of Formula C-17 were the same as those for the 9,10-dihydro-acridine derivative of Formula C-10 provided in Example 10, except that:
the compound E-1 in Step (3) of Example 10 was replaced by the compound of Formula E-8. The yield was 74%.

Example 18

This example provides a 9,10-dihydro-acridine derivative having a structure of Formula C-18:

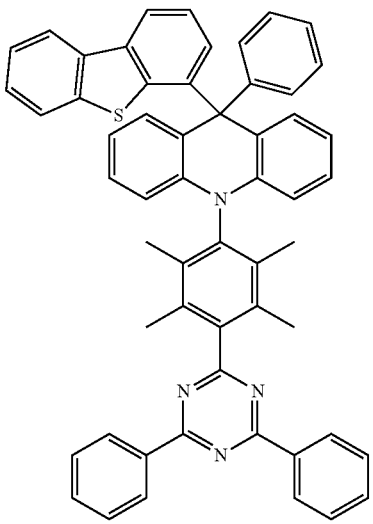

(C-18)

The preparation steps of the 9,10-dihydro-acridine derivative of Formula C-18 were the same as those for the 9,10-dihydro-acridine derivative of Formula C-10 provided in Example 10, except that:
the compound E-1 in Step (3) of Example 10 was replaced by the compound of Formula E-9. The yield was 78%.

Example 19

This example provides a 9,10-dihydro-acridine derivative having a structure of Formula C-19:

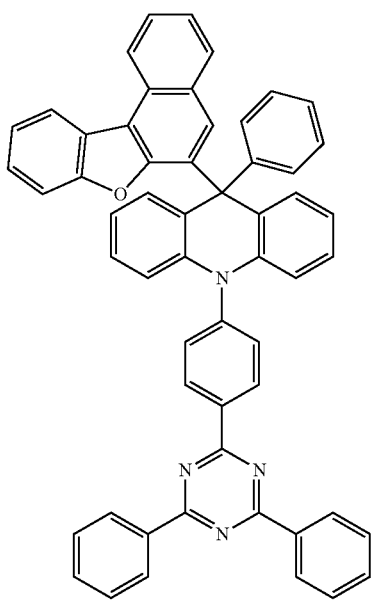

(C-19)

The synthesis route for the 9,10-dihydro-acridine derivative of Formula C-19 is shown below:

The method for preparing the 9,10-dihydro-acridine derivative of Formula C-19 comprises specifically the following steps.

(1) Synthesis of Intermediate 1-1

Under nitrogen atmosphere, 9(10H)-acridone (the compound A-1) (19.5 g, 100 mmol) and tetrahydrofuran (700 mL) were added to a 1 L three-neck flask. A phenyl magnesium bromide (the compound B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the solid compound 1-1 (24 g, yield: 88%).

(2) Synthesis of Intermediate 2-3

Under nitrogen atmosphere, the compound 1-1 (22.0 g, 80 mmol), the compound D-3 (35 g, 160 mmol), and dichloromethane (1000 mL) were added to a 2 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the

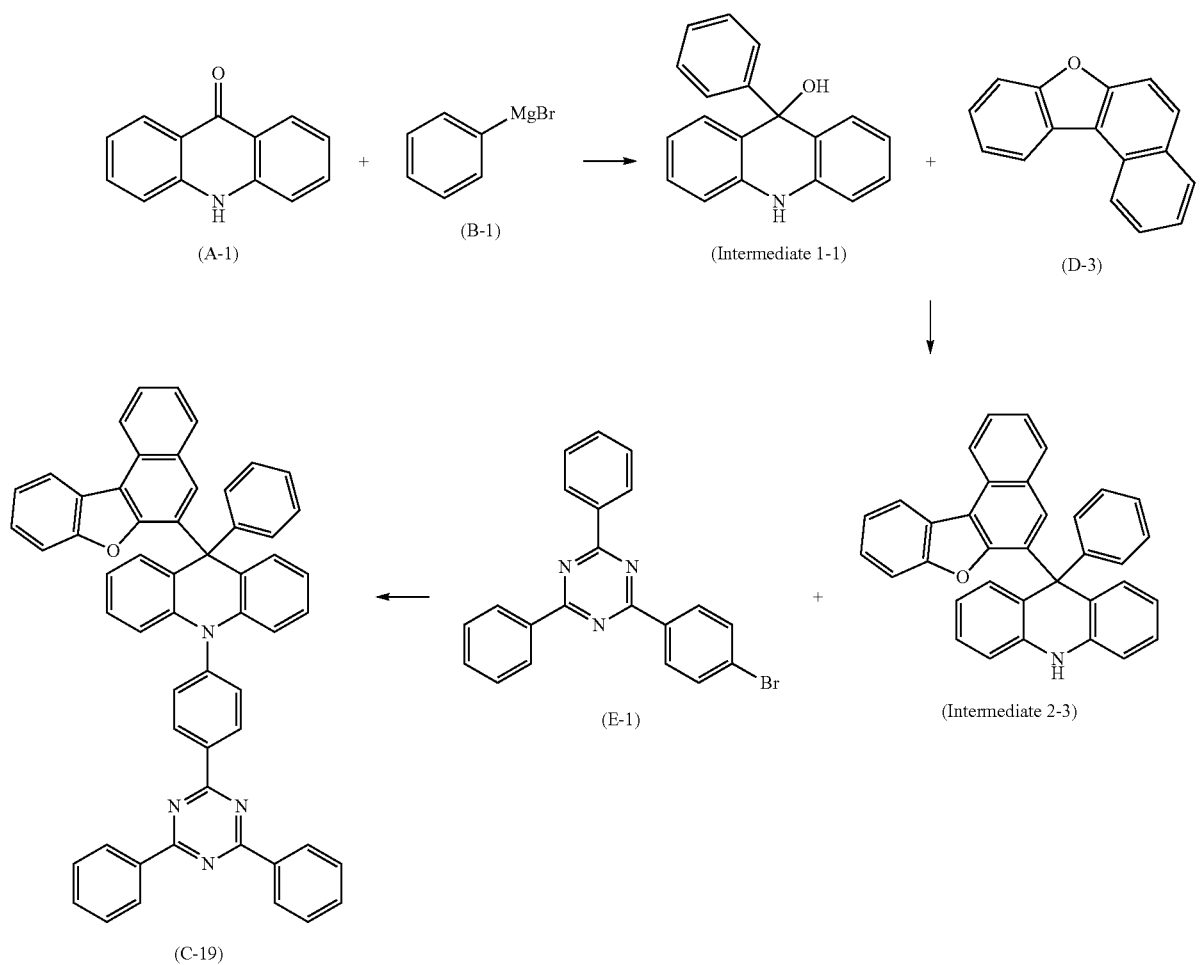

solvent was removed by rotary evaporation. The residue was purified by column chromatography on silica gel, to obtain the solid compound 2-3 (12.8 g, yield 34%).

(3) Synthesis of 9,10-dihydro-acridine Derivative C-19

Under nitrogen atmosphere, the compound 2-3 (9.5 g, 20 mmol), palladium diacetate (0.13 g, 0.6 mmol), tri-tert-butylphosphine (0.45 g, 2.2 mmol), the compound E-1 (8.5 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-19 (12.0 g, yield 82%).

Element analysis: (C56H36N4O) calculated: C, 86.13; H, 4.65; N, 7.17; O, 2.05. found: C, 86.10; H, 4.67; N, 7.15; O, 2.08, HRMS (ESI) m/z (M+): calculated: 780.2889. found: 780.2877.

Example 20

This example provides a 9,10-dihydro-acridine derivative having a structure of Formula C-20:

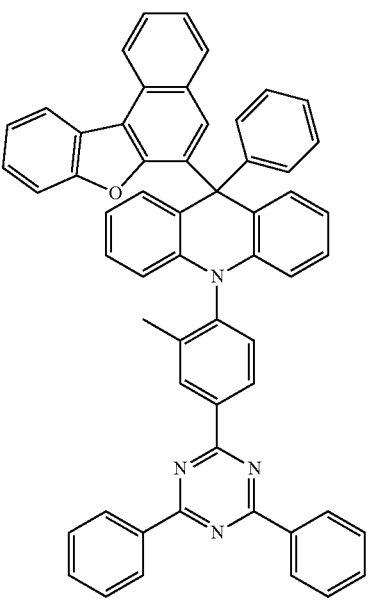
(C-20)

The preparation steps of the 9,10-dihydro-acridine derivative of Formula C-20 were the same as those for the 9,10-dihydro-acridine derivative of Formula C-19 provided in Example 19, except that:

the compound E-1 in Step (3) of Example 19 was replaced by the compound of Formula E-2. The yield was 85%.

Example 21

This example provides a 9,10-dihydro-acridine derivative having a structure of Formula C-21:

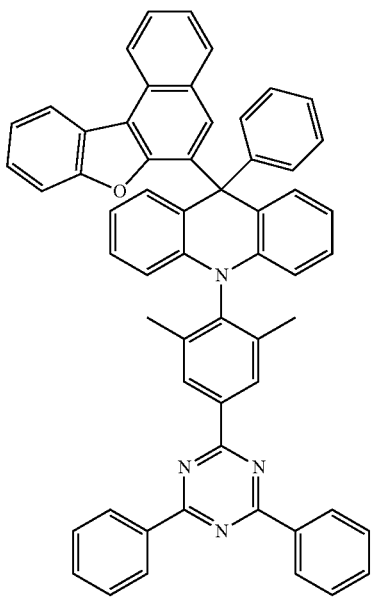
(C-21)

The preparation steps of the 9,10-dihydro-acridine derivative of Formula C-21 were the same as those for the 9,10-dihydro-acridine derivative of Formula C-19 provided in Example 19, except that:

the compound E-1 in Step (3) of Example 19 was replaced by the compound of Formula E-3. The yield was 81%.

Example 22

This example provides a 9,10-dihydro-acridine derivative having a structure of Formula C-22:

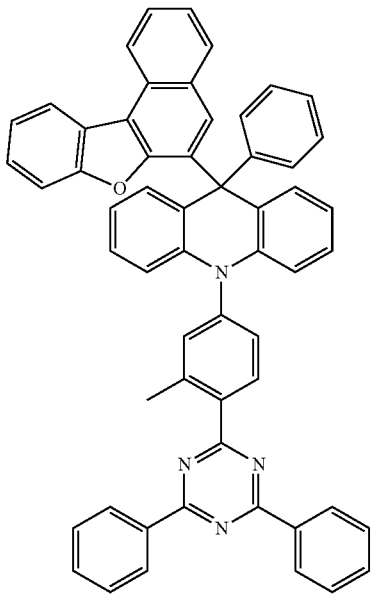
(C-22)

The preparation steps of the 9,10-dihydro-acridine derivative of Formula C-22 were the same as those for the 9,10-dihydro-acridine derivative of Formula C-19 provided in Example 19, except that:

the compound E-1 in Step (3) of Example 19 was replaced by the compound of Formula E-4. The yield was 85%.

Example 23

This example provides a 9,10-dihydro-acridine derivative having a structure of Formula C-23:

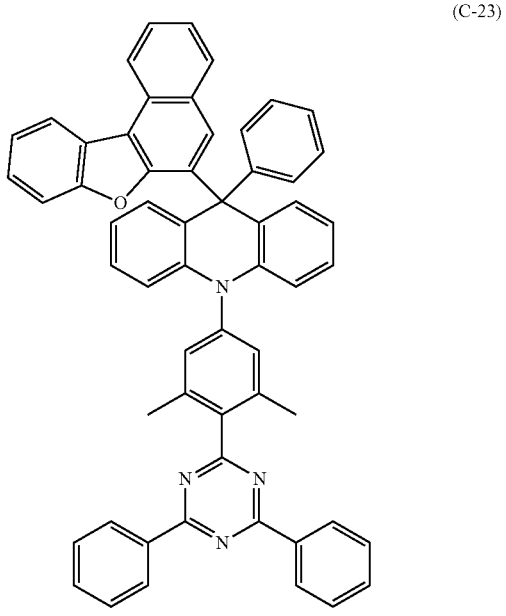 [SMILES: Cc1cc(N2c3ccccc3C(c3ccccc3)(c3cc4ccccc4c4c3oc3ccccc34)c3ccccc32)cc(C)c1-c1nc(-c2ccccc2)nc(-c2ccccc2)n1]

(C-23)

The preparation steps of the 9,10-dihydro-acridine derivative of Formula C-23 were the same as those for the 9,10-dihydro-acridine derivative of Formula C-19 provided in Example 19, except that:
the compound E-1 in Step (3) of Example 19 was replaced by the compound of Formula E-5. The yield was 84%.

Example 24

This example provides a 9,10-dihydro-acridine derivative having a structure of Formula C-24:

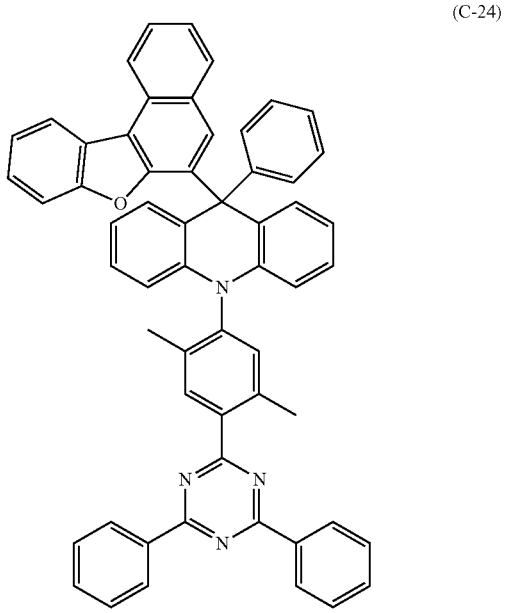 [SMILES: Cc1cc(N2c3ccccc3C(c3ccccc3)(c3cc4ccccc4c4c3oc3ccccc34)c3ccccc32)c(C)cc1-c1nc(-c2ccccc2)nc(-c2ccccc2)n1]

(C-24)

The preparation steps of the 9,10-dihydro-acridine derivative of Formula C-24 were the same as those for the 9,10-dihydro-acridine derivative of Formula C-19 provided in Example 19, except that:
the compound E-1 in Step (3) of Example 19 was replaced by the compound of Formula E-6. The yield was 79%.

Example 25

This example provides a 9,10-dihydro-acridine derivative having a structure of Formula C-25:

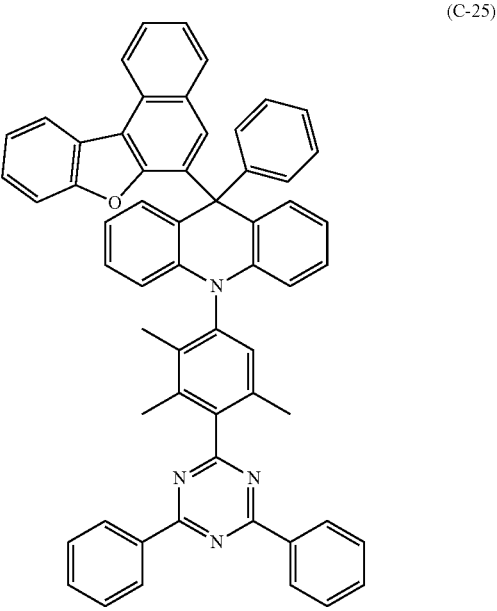 [SMILES: Cc1cc(N2c3ccccc3C(c3ccccc3)(c3cc4ccccc4c4c3oc3ccccc34)c3ccccc32)c(C)c(C)c1-c1nc(-c2ccccc2)nc(-c2ccccc2)n1]

(C-25)

The preparation steps of the 9,10-dihydro-acridine derivative of Formula C-25 were the same as those for the 9,10-dihydro-acridine derivative of Formula C-19 provided in Example 19, except that:
the compound E-1 in Step (3) of Example 19 was replaced by the compound of Formula E-7. The yield was 76%.

Example 26

This example provides a 9,10-dihydro-acridine derivative having a structure of Formula C-26:

(C-26)

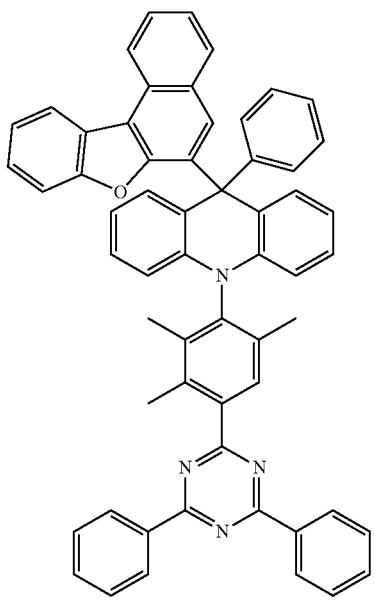

The preparation steps of the 9,10-dihydro-acridine derivative of Formula C-26 were the same as those for the 9,10-dihydro-acridine derivative of Formula C-19 provided in Example 19, except that:

the compound E-1 in Step (3) of Example 19 was replaced by the compound of Formula E-8. The yield was 73%.

Example 27

This example provides a 9,10-dihydro-acridine derivative having a structure of Formula C-27:

(C-27)

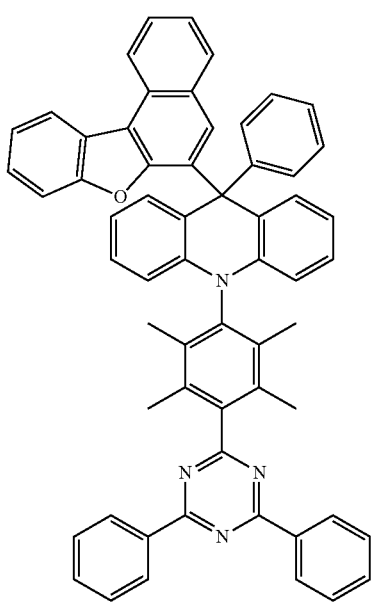

The preparation steps of the 9,10-dihydro-acridine derivative of Formula C-27 were the same as those for the 9,10-dihydro-acridine derivative of Formula C-19 provided in Example 19, except that:

the compound E-1 in Step (3) of Example 19 was replaced by the compound of Formula E-9. The yield was 75%.

Example 28

This example provides a 9,10-dihydro-acridine derivative having a structure of Formula C-37:

(C-37)

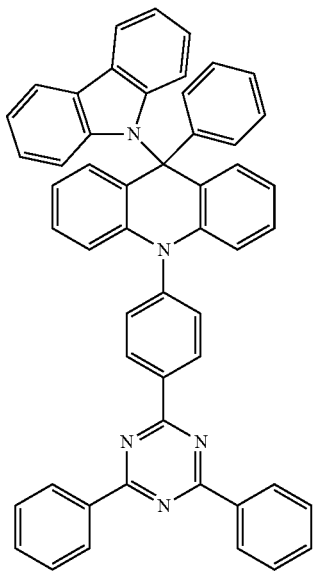

The synthesis route for the 9,10-dihydro-acridine derivative of Formula C-37 is shown below:

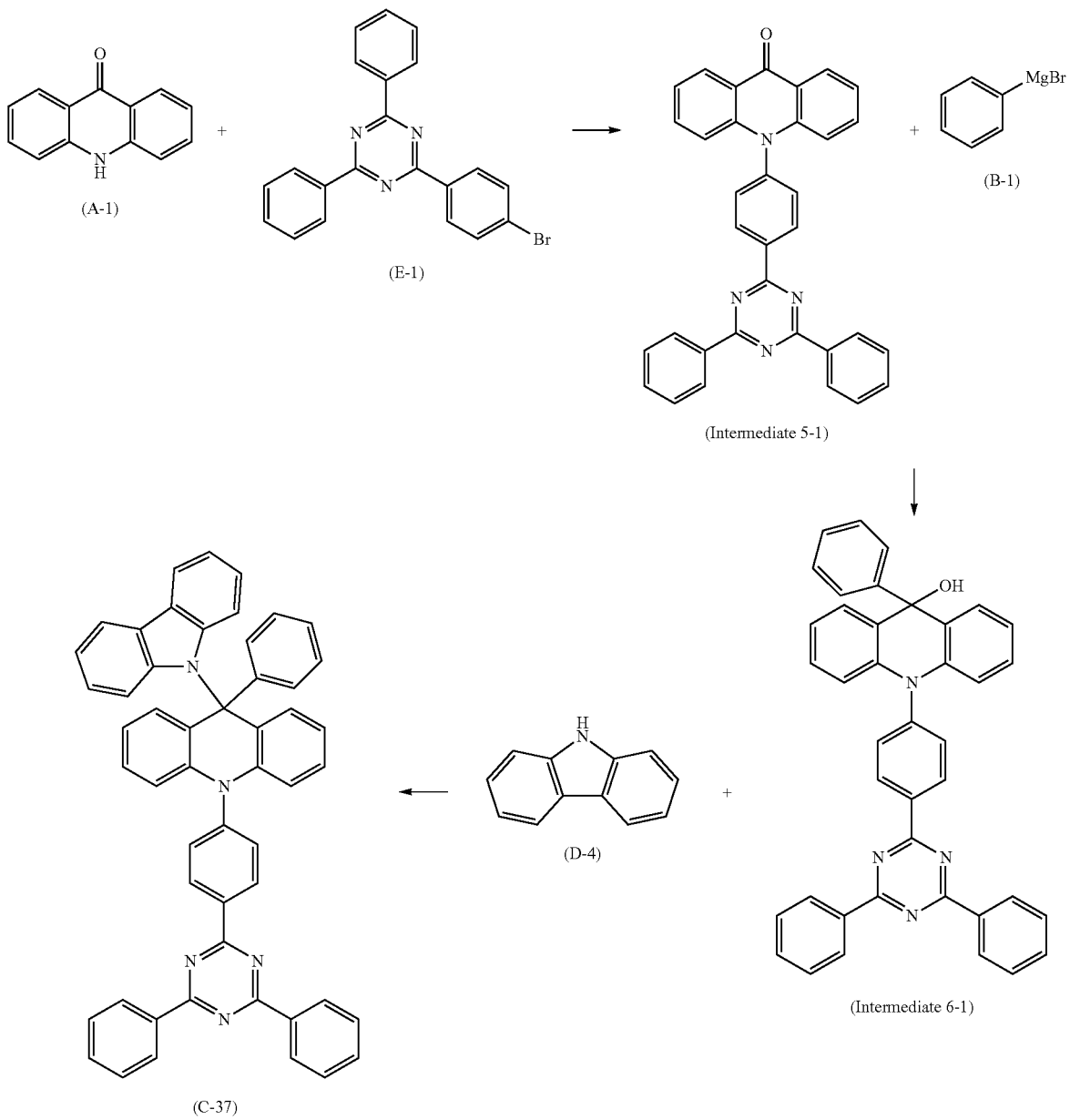

The method for preparing the 9,10-dihydro-acridine derivative of Formula C-37 comprises specifically the following steps.

(1) Synthesis of Intermediate 5-1

Under nitrogen atmosphere, 9(10H)-acridone (the compound A-1) (19.5 g, 100 mmol), palladium diacetate (0.65 g, 3 mmol), tri-tert-butylphosphine (2.25 g, 11.0 mmol), the compound E-1 (42.5 g, 110 mmol), sodium-t-butoxide (28.5 g), and toluene (100 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the intermediate 5-1 as a solid (63.8 g, yield 87%).

(2) Synthesis of Intermediate 6-1

Under nitrogen atmosphere, the compound 5-1 (40 g, 80 mmol) and tetrahydrofuran (800 mL) were added. A phenyl magnesium bromide (the compound B-1) solution (88 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the Intermediate 6-1 as a solid (34.8 g, yield: 78%).

(3) Synthesis of 9,10-dihydro-acridine Derivative C-37

Under nitrogen atmosphere, the compound 6-1 (29 g, 50 mmol), tetrahydrofuran (1000 mL), triphenylphosphine (19 g, 150 mmol), carbazole (the compound D-4) (10 g, 60 mmol), and DEAD (diethyl azodiformate) (10.5 g, 60 mmol) were added, and reacted at room temperature for 12 hrs. The reaction solution was extracted with dichloromethane (3×), and then the solvent was removed by rotary evaporation. The residue was purified by column chromatography on silica gel, to obtain a solid compound C-37 (23.5 g, yield: 65%).

Element analysis: (C56H36N4O) calculated: (C58H39N5) calculated: C, 86.43; H, 4.88; N, 8.69. found: C, 86.47; H, 4.85; N, 8.67, HRMS (ESI) m/z (M+): calculated: 805.3205. found: 805.3237.

Example 29

This example provides a 9,10-dihydro-acridine derivative having a structure of Formula C-38:

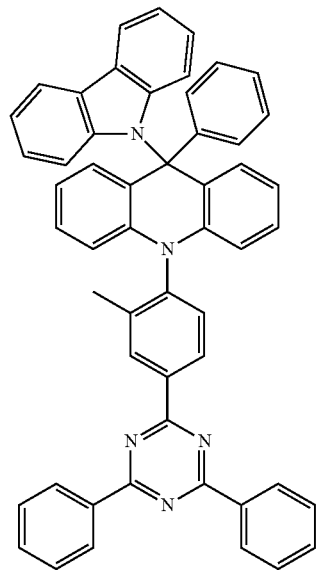
(C-38)

The preparation steps of the 9,10-dihydro-acridine derivative of Formula C-38 were the same as those for the 9,10-dihydro-acridine derivative of Formula C-37 provided in Example 28, except that:

the compound E-1 in Step (3) of Example 28 was replaced by the compound of Formula E-2. The yield was 84%.

Example 30

This example provides a 9,10-dihydro-acridine derivative having a structure of Formula C-39:

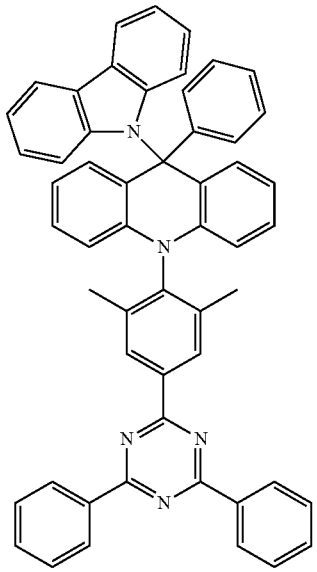
(C-39)

The preparation steps of the 9,10-dihydro-acridine derivative of Formula C-39 were the same as those for the 9,10-dihydro-acridine derivative of Formula C-37 provided in Example 28, except that:

the compound E-1 in Step (3) of Example 28 was replaced by the compound of Formula E-3. The yield was 81%.

Example 31

This example provides a 9,10-dihydro-acridine derivative having a structure of Formula C-40:

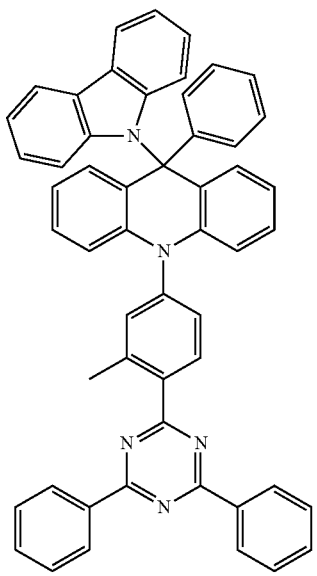
(C-40)

The preparation steps of the 9,10-dihydro-acridine derivative of Formula C-40 were the same as those for the 9,10-dihydro-acridine derivative of Formula C-37 provided in Example 28, except that:

the compound E-1 in Step (3) of Example 28 was replaced by the compound of Formula E-4. The yield was 85%.

Example 32

This example provides a 9,10-dihydro-acridine derivative having a structure of Formula C-41:

(C-41)

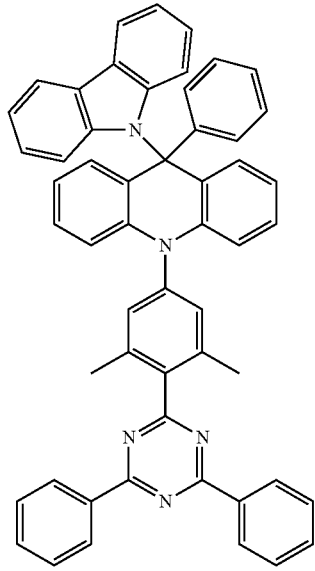

The preparation steps of the 9,10-dihydro-acridine derivative of Formula C-41 were the same as those for the 9,10-dihydro-acridine derivative of Formula C-37 provided in Example 28, except that:
the compound E-1 in Step (3) of Example 28 was replaced by the compound of Formula E-5. The yield was 85%.

Example 33

This example provides a 9,10-dihydro-acridine derivative having a structure of Formula C-42:

(C-42)

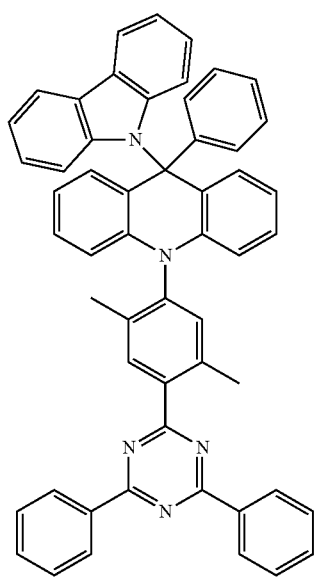

The preparation steps of the 9,10-dihydro-acridine derivative of Formula C-42 were the same as those for the 9,10-dihydro-acridine derivative of Formula C-37 provided in Example 28, except that:

the compound E-1 in Step (3) of Example 28 was replaced by the compound of Formula E-6. The yield was 79%.

Example 34

This example provides a 9,10-dihydro-acridine derivative having a structure of Formula C-43:

(C-43)

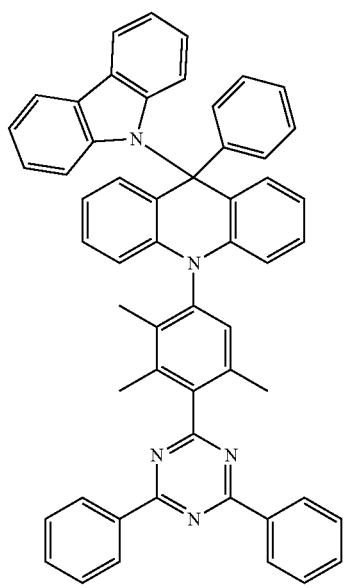

The preparation steps of the 9,10-dihydro-acridine derivative of Formula C-43 were the same as those for the 9,10-dihydro-acridine derivative of Formula C-37 provided in Example 28, except that:
the compound E-1 in Step (3) of Example 28 was replaced by the compound of Formula E-7. The yield was 76%.

Example 35

This example provides a 9,10-dihydro-acridine derivative having a structure of Formula C-44:

(C-44)

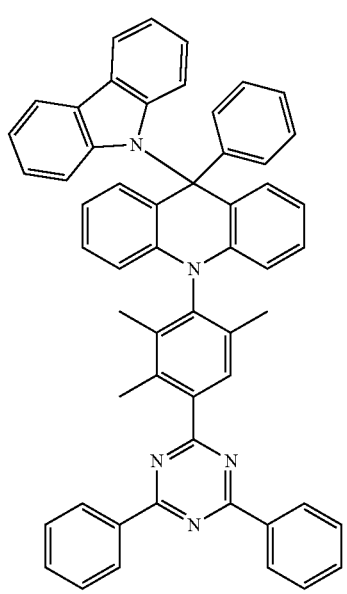

The preparation steps of the 9,10-dihydro-acridine derivative of Formula C-44 were the same as those for the 9,10-dihydro-acridine derivative of Formula C-37 provided in Example 28, except that:

the compound E-1 in Step (3) of Example 28 was replaced by the compound of Formula E-8. The yield was 73%.

Example 36

This example provides a 9,10-dihydro-acridine derivative having a structure of Formula C-45:

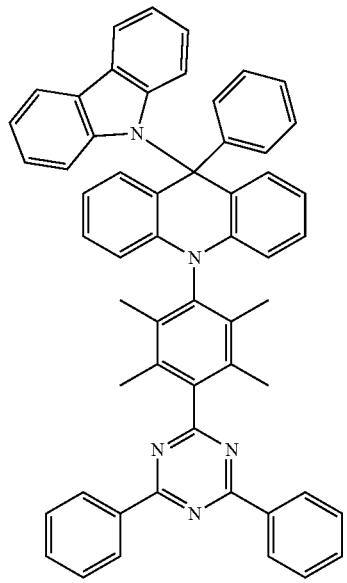

(C-45)

The preparation steps of the 9,10-dihydro-acridine derivative of Formula C-45 were the same as those for the 9,10-dihydro-acridine derivative of Formula C-37 provided in Example 28, except that:

the compound E-1 in Step (3) of Example 28 was replaced by the compound of Formula E-9. The yield was 78%.

Example 37

This example provides a 9,10-dihydro-acridine derivative having a structure of Formula C-46:

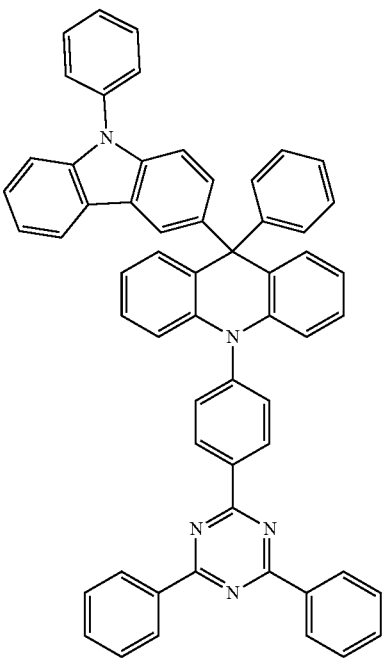

(C-46)

The synthesis route for the 9,10-dihydro-acridine derivative of Formula C-46 is shown below:

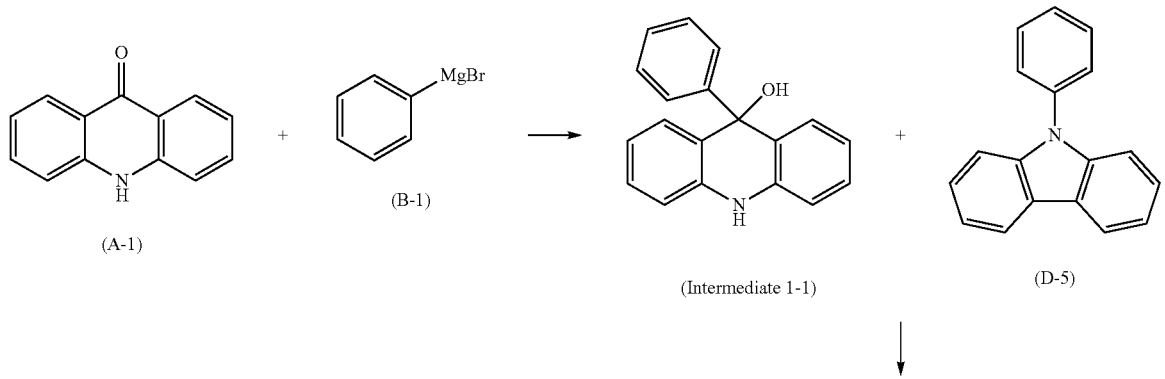

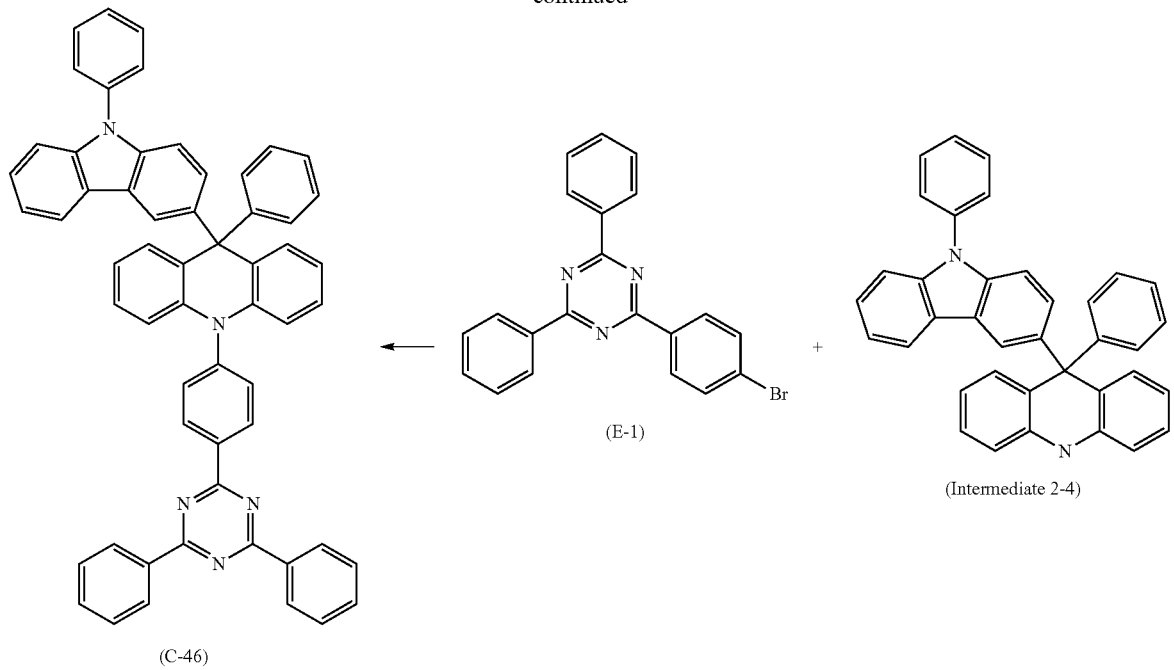

(C-46)

The method for preparing the 9,10-dihydro-acridine derivative of Formula C-46 comprises specifically the following steps.

(1) Synthesis of Intermediate 1-1

Under nitrogen atmosphere, 9(10H)-acridone (the compound A-1) (19.5 g, 100 mmol) and tetrahydrofuran (700 mL) were added to a 1 L three-neck flask. A phenyl magnesium bromide (the compound B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the solid compound 1-1 (24 g, yield: 88%).

(2) Synthesis of Intermediate 2-4

Under nitrogen atmosphere, the compound 1-1 (22.0 g, 80 mmol), 9-phenylcarbazole (the compound D-5) (20 g, 80 mmol), and dichloromethane (800 mL) were added. Then, a solution of boron trifluoride (11.5 mL, 80 mmol) in diethyl ether was added dropwise, reacted at room temperature for 5 hrs, and then quenched by adding water. The reaction solution was extracted with toluene (3×), and then the solvent was removed by rotary evaporation. The residue was purified by column chromatography on silica gel, to obtain the intermediate 2-4 as a solid (33.3 g, yield: 85%).

(3) Synthesis of 9,10-dihydro-acridine Derivative C-46

Under nitrogen atmosphere, the compound 2-4 (10.0 g, 20 mmol), palladium diacetate (0.13 g, 0.6 mmol), tri-tert-butylphosphine (0.45 g, 2.2 mmol), the compound E-1 (8.5 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-46 (13.5 g, yield 84%).

Element analysis: (C58H39N5) calculated: C, 86.43; H, 4.88; N, 8.69; found: C, 86.47; H, 4.82; N, 8.72, HRMS (ESI) m/z (M+): calculated: 805.3205; found: 805.3237.

Example 38

This example provides a 9,10-dihydro-acridine derivative having a structure of Formula C-47:

(C-47)

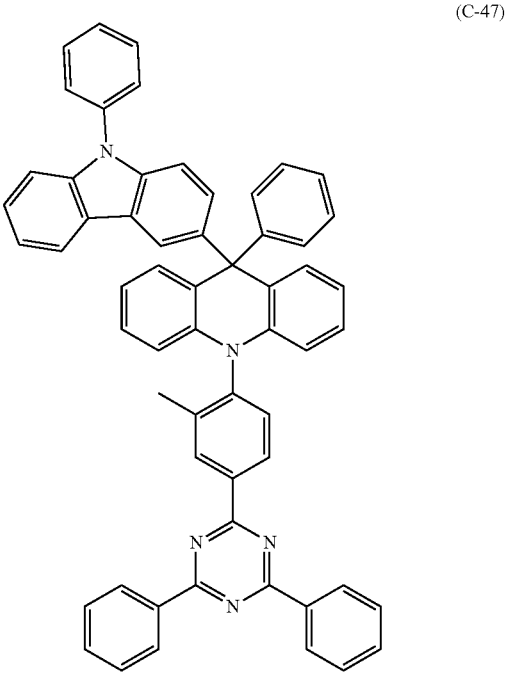 [SMILES: Cc1cc(-c2nc(-c3ccccc3)nc(-c3ccccc3)n2)ccc1N1c2ccccc2C(c2ccccc2)(c2ccc3c(c2)c2ccccc2n3-c2ccccc2)c2ccccc21]

The preparation steps of the 9,10-dihydro-acridine derivative of Formula C-47 were the same as those for the 9,10-dihydro-acridine derivative of Formula C-46 provided in Example 37, except that:

the compound E-1 in Step (3) of Example 37 was replaced by the compound of Formula E-2. The yield was 82%.

Example 38

This example provides a 9,10-dihydro-acridine derivative having a structure of Formula C-48:

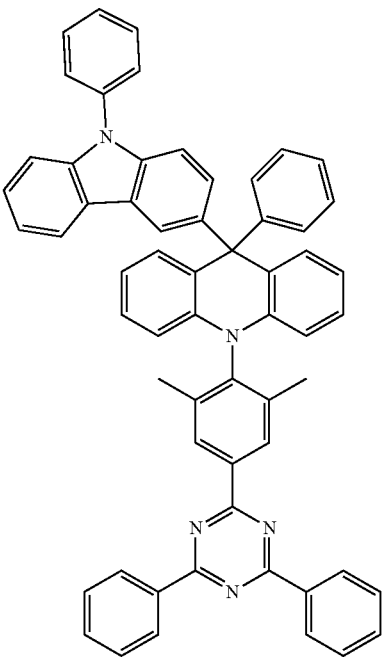

(C-48)

The preparation steps of the 9,10-dihydro-acridine derivative of Formula C-48 were the same as those for the 9,10-dihydro-acridine derivative of Formula C-46 provided in Example 37, except that:

the compound E-1 in Step (3) of Example 37 was replaced by the compound of Formula E-3. The yield was 80%.

Example 40

This example provides a 9,10-dihydro-acridine derivative having a structure of Formula C-49:

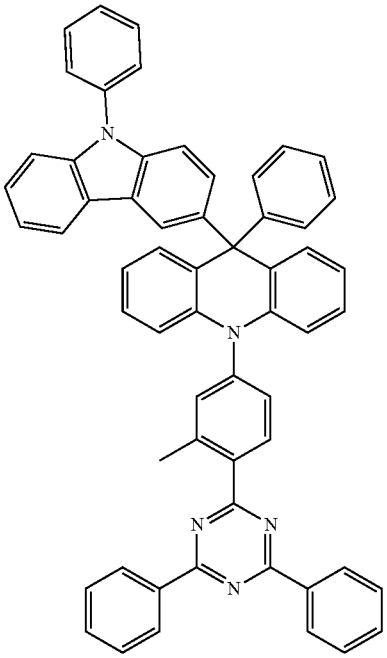

(C-49)

The preparation steps of the 9,10-dihydro-acridine derivative of Formula C-49 were the same as those for the 9,10-dihydro-acridine derivative of Formula C-46 provided in Example 37, except that:

the compound E-1 in Step (3) of Example 37 was replaced by the compound of Formula E-4. The yield was 81%.

Example 41

This example provides a 9,10-dihydro-acridine derivative having a structure of Formula C-50:

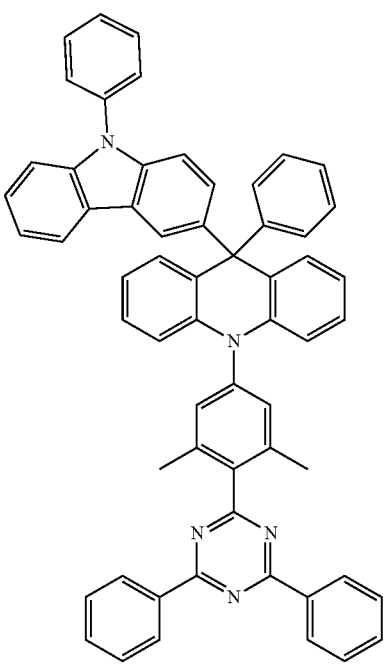

(C-50)

The preparation steps of the 9,10-dihydro-acridine derivative of Formula C-50 were the same as those for the 9,10-dihydro-acridine derivative of Formula C-46 provided in Example 37, except that:

the compound E-1 in Step (3) of Example 37 was replaced by the compound of Formula E-5. The yield was 853%.

Example 42

This example provides a 9,10-dihydro-acridine derivative having a structure of Formula C-51:

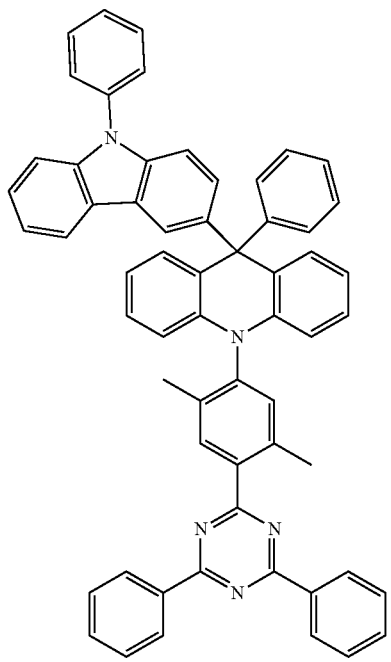

(C-51)

The preparation steps of the 9,10-dihydro-acridine derivative of Formula C-51 were the same as those for the 9,10-dihydro-acridine derivative of Formula C-46 provided in Example 37, except that:

the compound E-1 in Step (3) of Example 37 was replaced by the compound of Formula E-6. The yield was 77%.

Example 43

This example provides a 9,10-dihydro-acridine derivative having a structure of Formula C-52:

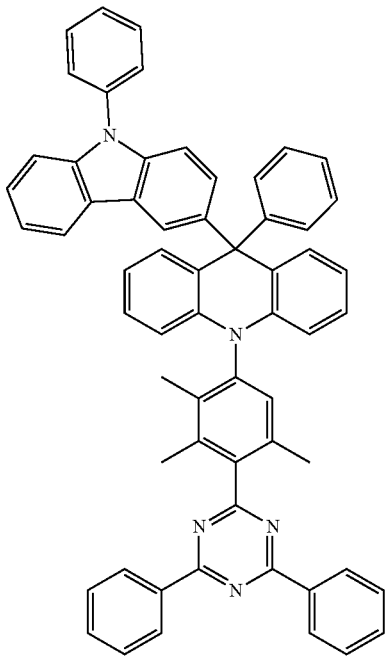

(C-52)

The preparation steps of the 9,10-dihydro-acridine derivative of Formula C-52 were the same as those for the 9,10-dihydro-acridine derivative of Formula C-46 provided in Example 37, except that:

the compound E-1 in Step (3) of Example 37 was replaced by the compound of Formula E-7. The yield was 79%.

Example 44

This example provides a 9,10-dihydro-acridine derivative having a structure of Formula C-53:

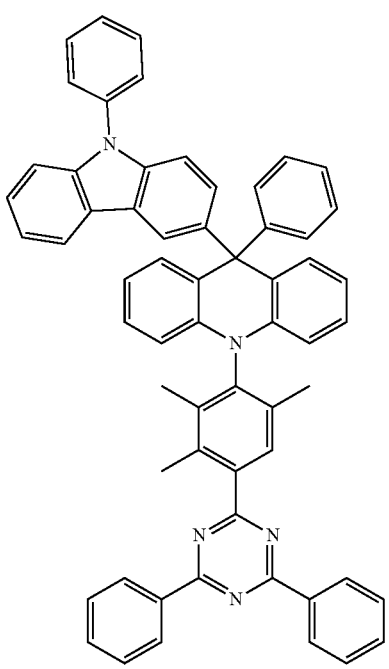

(C-53)

The preparation steps of the 9,10-dihydro-acridine derivative of Formula C-53 were the same as those for the 9,10-dihydro-acridine derivative of Formula C-46 provided in Example 37, except that:

the compound E-1 in Step (3) of Example 37 was replaced by the compound of Formula E-8. The yield was 76%.

Example 45

This example provides a 9,10-dihydro-acridine derivative having a structure of Formula C-54:

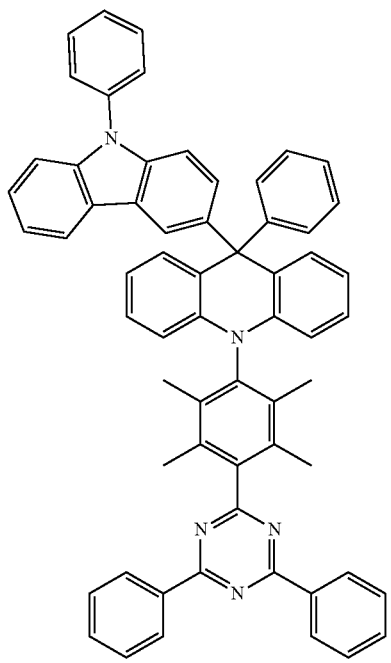

(C-54)

The preparation steps of the 9,10-dihydro-acridine derivative of Formula C-54 were the same as those for the 9,10-dihydro-acridine derivative of Formula C-46 provided in Example 37, except that:

the compound E-1 in Step (3) of Example 37 was replaced by the compound of Formula E-9. The yield was 72%.

Example 46

This example provides a 9,10-dihydro-acridine derivative having a structure of Formula C-55:

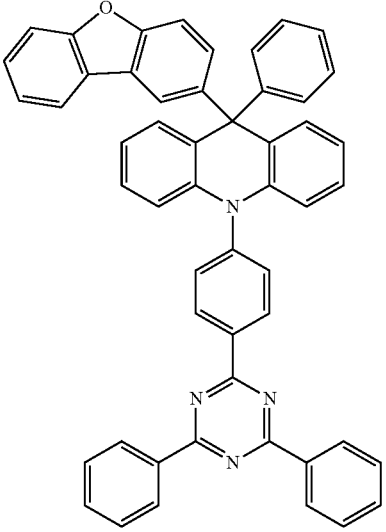

(C-55)

The synthesis route for the 9,10-dihydro-acridine derivative of Formula C-55 is shown below:

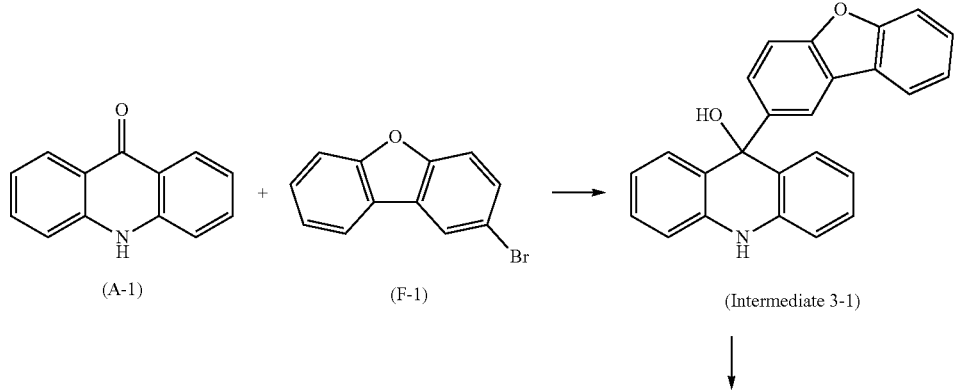

-continued

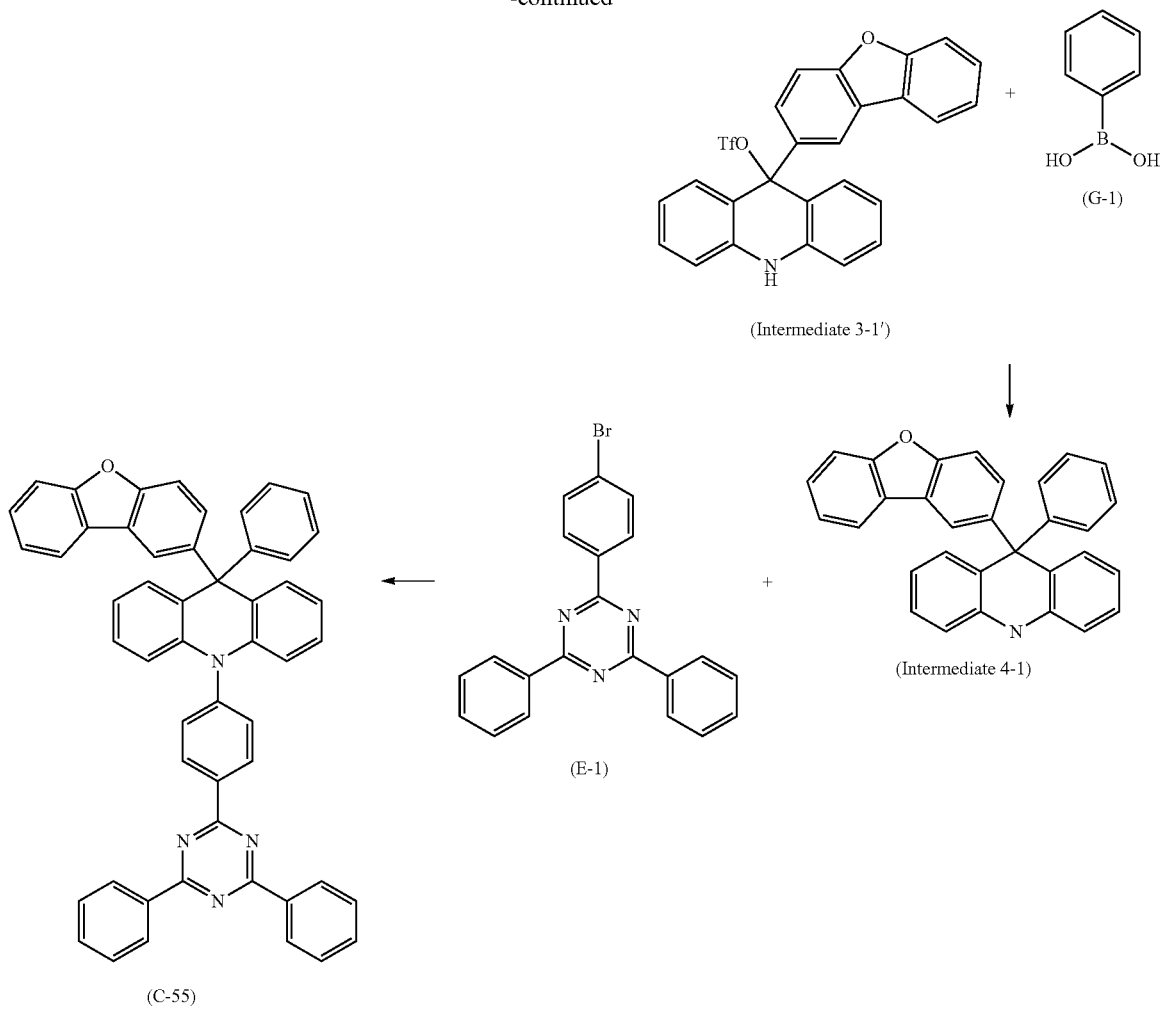

The method for preparing the 9,10-dihydro-acridine derivative of Formula C-55 comprises specifically the following steps.

(1) Synthesis of Intermediate 3-1

Under nitrogen atmosphere, the compound F-1 (24.6 g, 100 mmol), and tetrahydrofuran (500 mL) were added. At −78° C., n-butyl lithium (63 mL, 1.6 M) was added dropwise, reacted for 30 min at a low temperate and then for 3 hrs at an elevated temperature of 30° C., and then cooled to −78° C. A solution of 9(10H)-acridone (the compound A-1) (500 mL, 0.2 M, 9.5 g (100 mmol)) was added, slowly heated to 30° C., reacted for 15 hrs, and then quenched by adding an aqueous ammonium chloride solution. The reaction solution was extracted with chloroform, and then the solvent was removed by rotary evaporation. The residue was purified by column chromatography on silica gel, to obtain the intermediate 3-1 as a solid (20.3 g, yield 56%).

(2) Synthesis of Intermediate 3-1'

Under nitrogen atmosphere, the compound 3-1 (14.5 g, 40 mmol), triethylamine (5.0 g, 48 mmol), and dichloromethane (400 mL) were added. Trifluoromethanesulfonic anhydride (13.5 g, 48 mmol) was added at −20° C., and reacted at room temperature for 3 hrs. The reaction solution was extracted with toluene (3×), and then the solvent was removed by rotary evaporation. The residue was washed with methanol (3×), to obtain the intermediate 3-1' (17 g, yield: 87%).

(3) Synthesis of Intermediate 4-1

Under nitrogen atmosphere, the compound 3-1' (14.8 g, 30 mmol), phenylboronic acid (the compound G-1) (3.7 g, 30 mmol), potassium phosphate (70 g, 33 mmol), tetrakis (triphenylphosphine) palladium (1.7 g, 1.5 mmol), water (50 mL), and 1,4-dioxane (300 mL) were added, reacted at 120° C. for 8 hrs, and then cooled to room temperature. The reaction solution was extracted with chloroform, and then the solvent was removed by rotary evaporation. The residue was purified by column chromatography on silica gel, to obtain the intermediate 4-1 as a solid (10.3 g, yield 81%).

(4) Synthesis of 9,10-dihydro-acridine Derivative C-55

Under nitrogen atmosphere, the compound 4-1 (8.5 g, 20 mmol), palladium diacetate (0.13 g, 0.6 mmol), tri-tert-butylphosphine (0.45 g, 2.2 mmol), the compound E-1 (8.5 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-55 (12.3 g, yield 84%).

Element analysis: (C52H34N4O) calculated: C, 85.46; H, 4.69; N, 7.67; O, 2.19. found: C, 85.41; H, 4.73; N, 7.69; O, 2.23, HRMS (ESI) m/z (M+): calculated: 730.2732. found: 730.2749.

Example 47

This example provides a 9,10-dihydro-acridine derivative having a structure of Formula C-56:

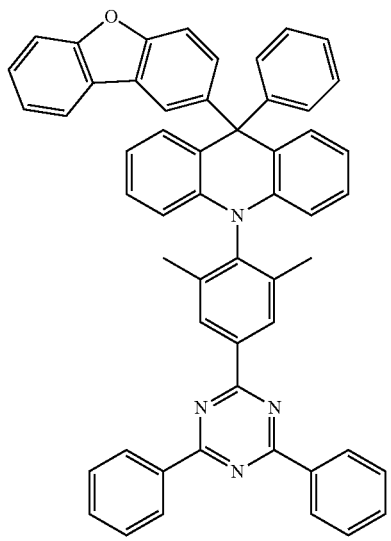
(C-56)

The preparation steps of the 9,10-dihydro-acridine derivative of Formula C-56 were the same as those for the 9,10-dihydro-acridine derivative of Formula C-55 provided in Example 46, except that:

the compound E-1 in Step (4) of Example 46 was replaced by the compound of Formula E-3. The yield was 82%.

Example 48

This example provides a 9,10-dihydro-acridine derivative having a structure of Formula C-57:

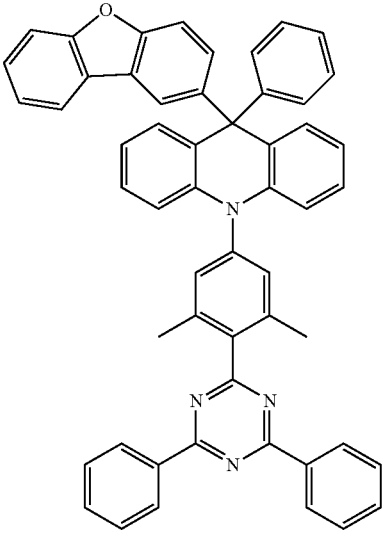
(C-57)

The preparation steps of the 9,10-dihydro-acridine derivative of Formula C-57 were the same as those for the 9,10-dihydro-acridine derivative of Formula C-55 provided in Example 46, except that:

the compound E-1 in Step (4) of Example 46 was replaced by the compound of Formula E-5. The yield was 81%.

Example 49

This example provides a 9,10-dihydro-acridine derivative having a structure of Formula C-58:

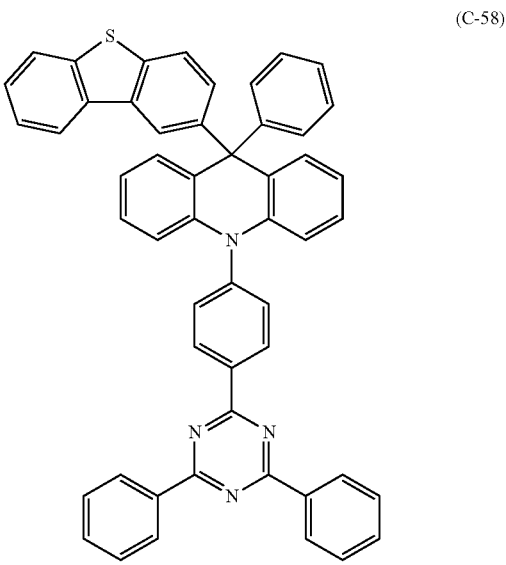 [SMILES: c1ccc(-c2nc(-c3ccccc3)nc(-c3ccc(N4c5ccccc5C(c5ccccc5)(c5ccc6sc7ccccc7c6c5)c5ccccc54)cc3)n2)cc1]
(C-58)

The synthesis route for the 9,10-dihydro-acridine derivative of Formula C-58 is shown below:

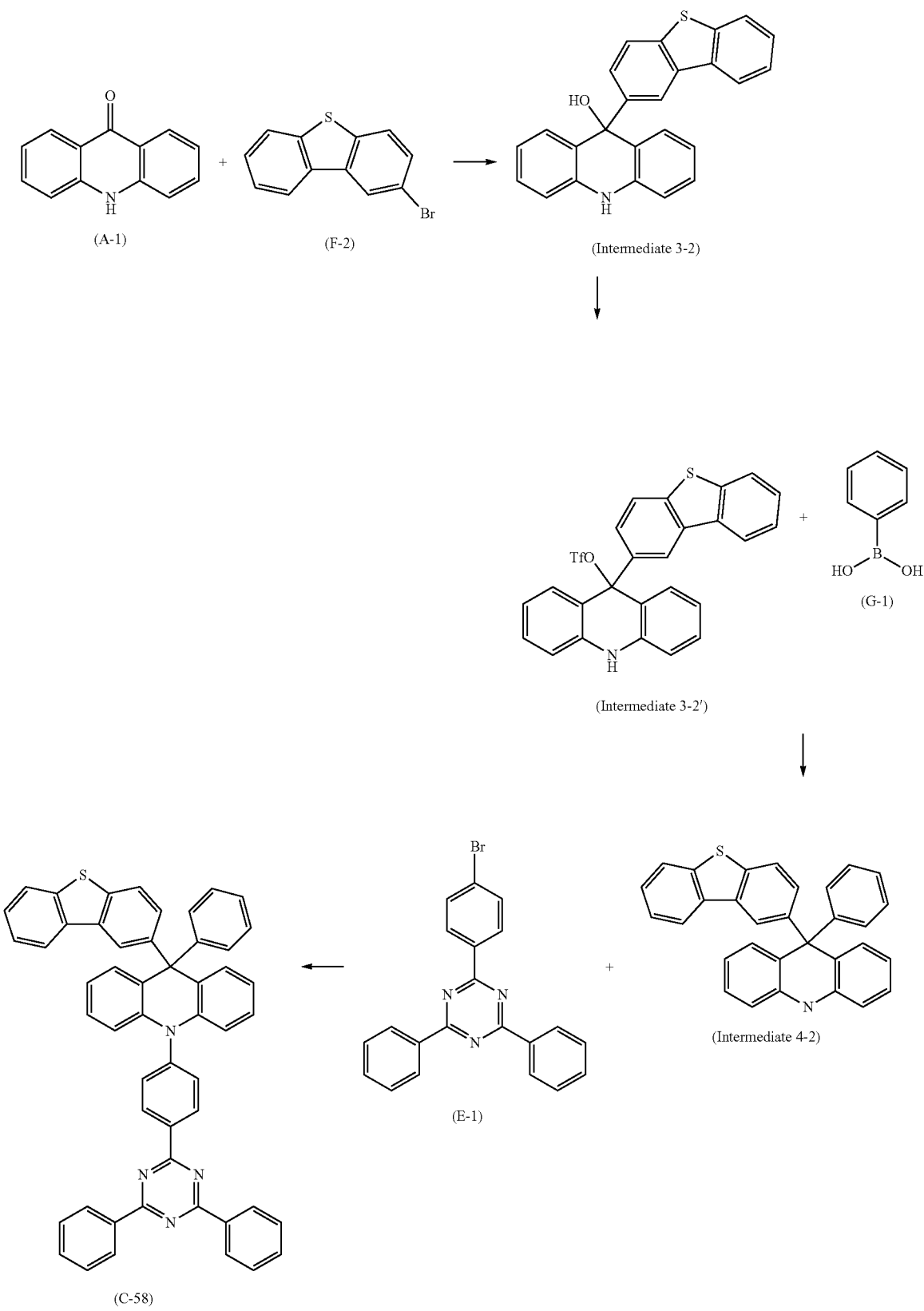

The preparation steps of the 9,10-dihydro-acridine derivative of Formula C-58 were the same as those for the 9,10-dihydro-acridine derivative of Formula C-55 provided in Example 46, except that:

the compound F-1 in Step (1) of Example 46 was replaced by the compound of Formula F-2. The yield was 83%.

Element analysis: (C52H34N4S) calculated: C, 83.62; H, 4.59; N, 7.50; S, 4.29. found: C, 83.57; H, 4.60; N, 7.52; S, 4.25, HRMS (ESI) m/z (M+): calculated: 746.2504. found: 746.2513.

Example 50

This example provides a 9,10-dihydro-acridine derivative having a structure of Formula C-61:

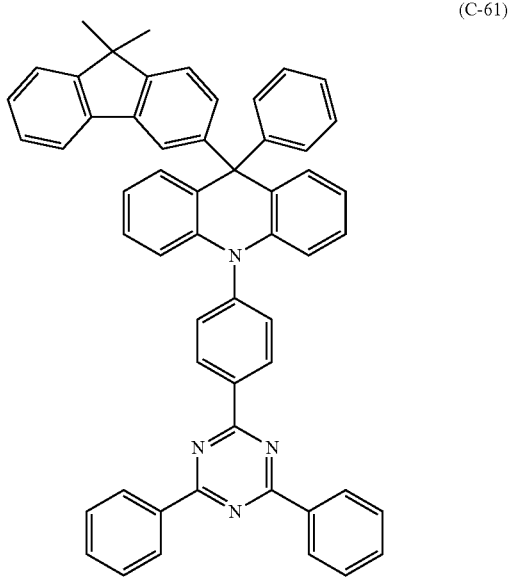 [SMILES: CC1(C)c2ccccc2-c2cc(C3(c4ccccc4)c4ccccc4N(c4ccc(-c5nc(-c6ccccc6)nc(-c6ccccc6)n5)cc4)c4ccccc43)ccc21]

The synthesis route for the 9,10-dihydro-acridine derivative of Formula C-61 is shown below:

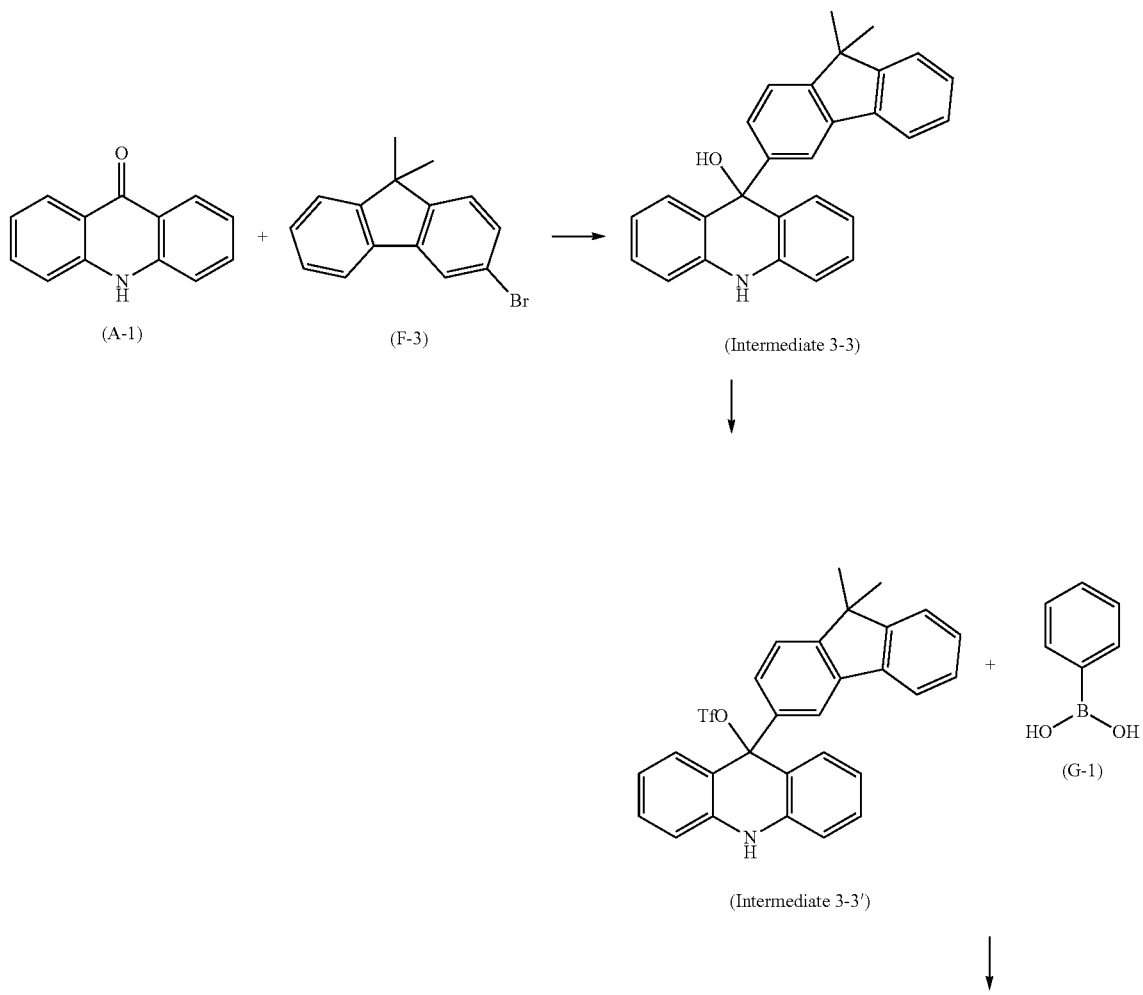

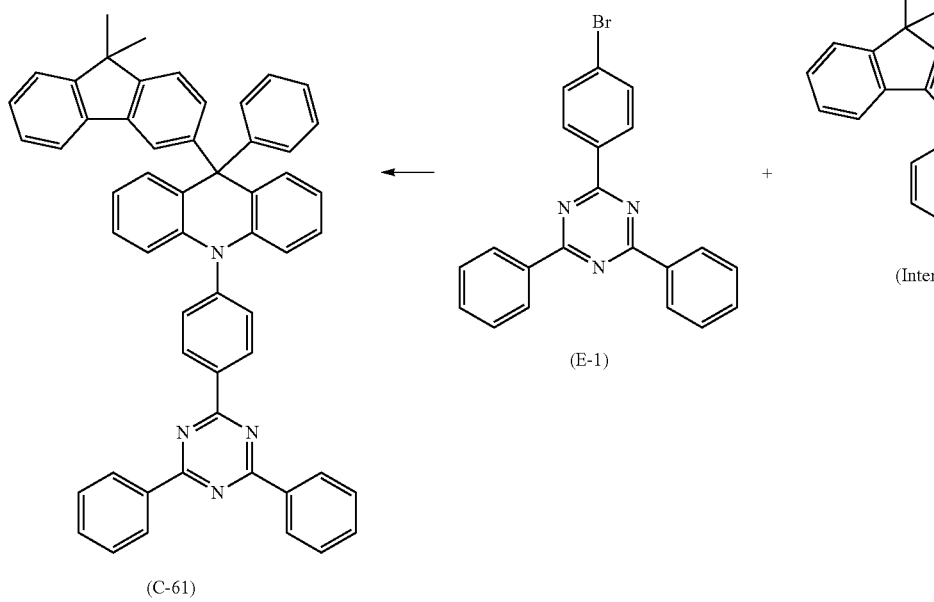

(C-61)

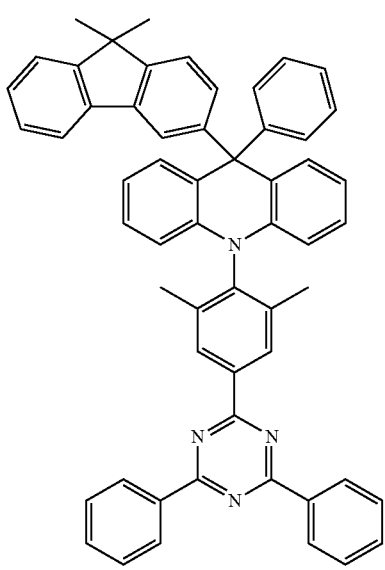

(C-62)

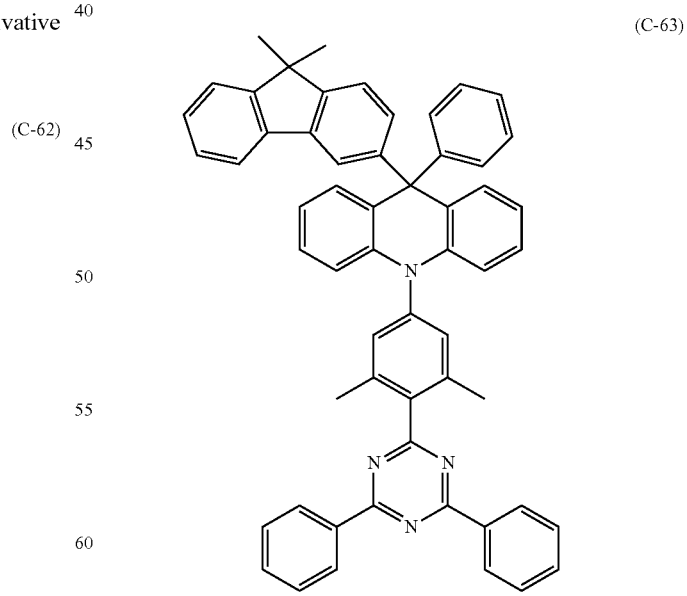

(Intermediate 4-3)

(E-1)

(C-63)

The preparation steps of the 9,10-dihydro-acridine derivative of Formula C-61 were the same as those for the 9,10-dihydro-acridine derivative of Formula C-55 provided in Example 46, except that:

the compound F-1 in Step (1) of Example 46 was replaced by the compound of Formula F-3. The yield was 84%.

Element analysis: (C55H40N4) calculated: C, 87.27; H, 5.33; N, 7.40; found: C, 87.2; H, 5.37; N, 7.42, HRMS (ESI) m/z (M+): calculated: 756.3253; found: 756.3239.

Example 51

This example provides a 9,10-dihydro-acridine derivative having a structure of Formula C-62:

The preparation steps of the 9,10-dihydro-acridine derivative of Formula C-62 were the same as those for the 9,10-dihydro-acridine derivative of Formula C-61 provided in Example 50, except that:

the compound E-1 in Step (4) of Example 50 was replaced by the compound of Formula E-3. The yield was 78%.

Example 52

This example provides a 9,10-dihydro-acridine derivative having a structure of Formula C-63:

The preparation steps of the 9,10-dihydro-acridine derivative of Formula C-63 were the same as those for the 9,10-dihydro-acridine derivative of Formula C-61 provided in Example 50, except that:

the compound E-1 in Step (4) of Example 50 was replaced by the compound of Formula E-5. The yield was 83%.
Example 53
This example provides a 9,10-dihydro-acridine derivative having a structure of Formula C-64:
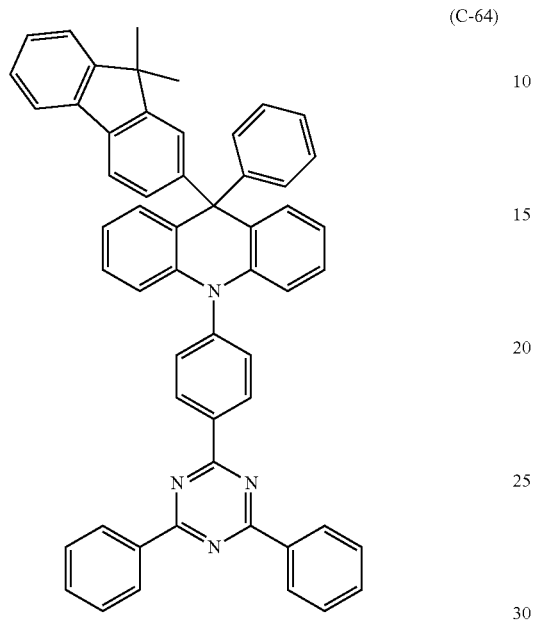
(C-64)
The synthesis route for the 9,10-dihydro-acridine derivative of Formula C-64 is shown below:
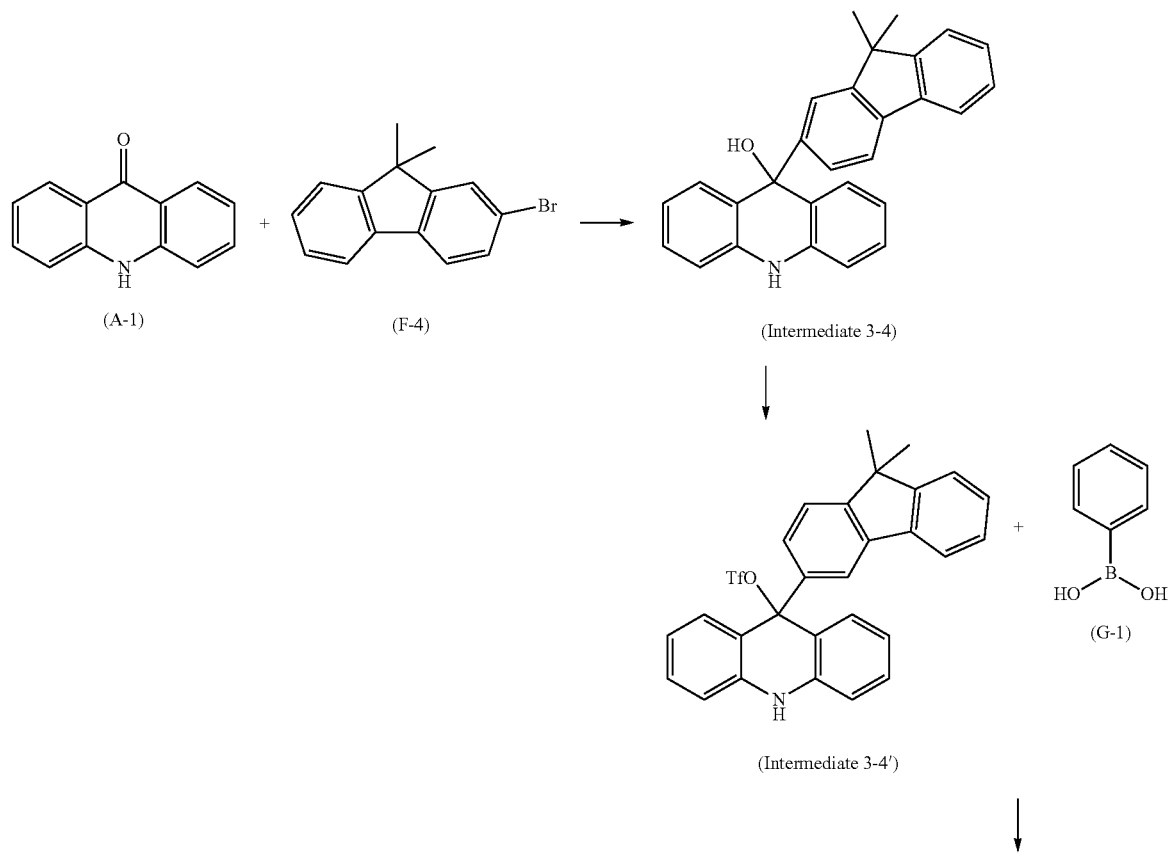

-continued

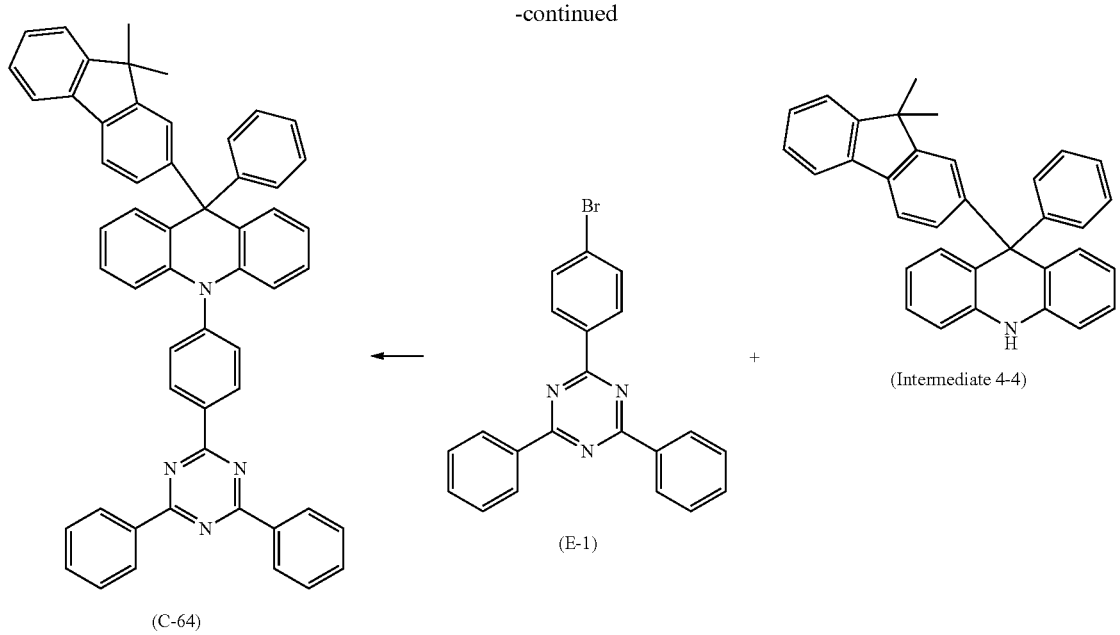

(C-64)

(E-1)

(Intermediate 4-4)

The preparation steps of the 9,10-dihydro-acridine derivative of Formula C-64 were the same as those for the 9,10-dihydro-acridine derivative of Formula C-55 provided in Example 46, except that:

the compound F-1 in Step (1) of Example 46 was replaced by the compound of Formula F-4. The yield was 78%.

Example 54

This example provides a 9,10-dihydro-acridine derivative having a structure of Formula C-65:

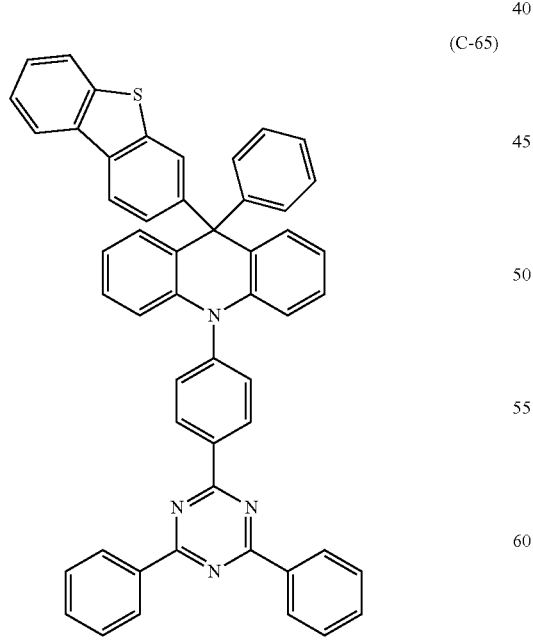

(C-65)

The synthesis route for the 9,10-dihydro-acridine derivative of Formula C-65 is shown below:

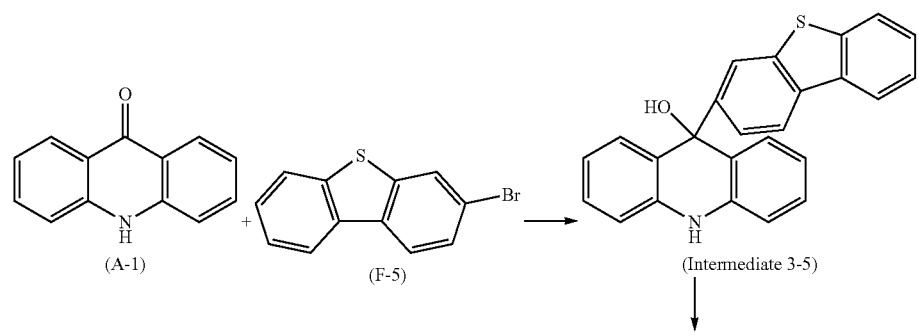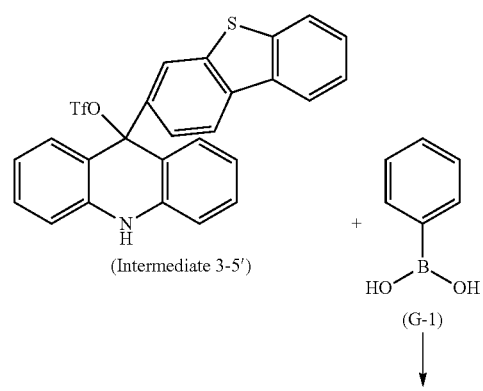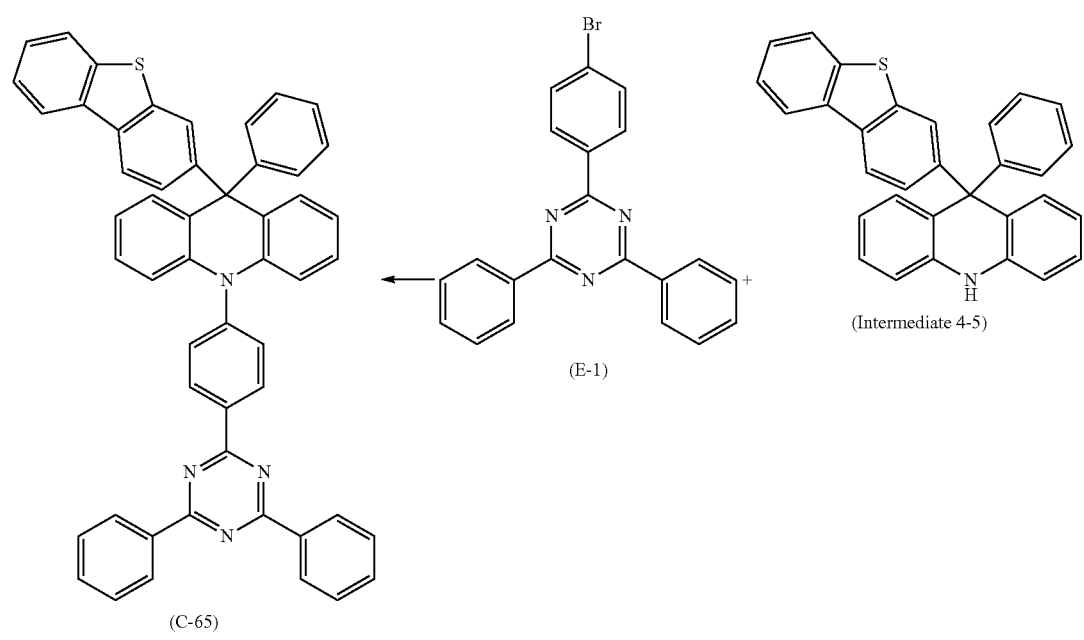

The preparation steps of the 9,10-dihydro-acridine derivative of Formula C-65 were the same as those for the 9,10-dihydro-acridine derivative of Formula C-55 provided in Example 46, except that:

the compound F-1 in Step (1) of Example 46 was replaced by the compound of Formula F-5. The yield was 78%.

Example 55

This example provides a 9,10-dihydro-acridine derivative having a structure of Formula C-66:

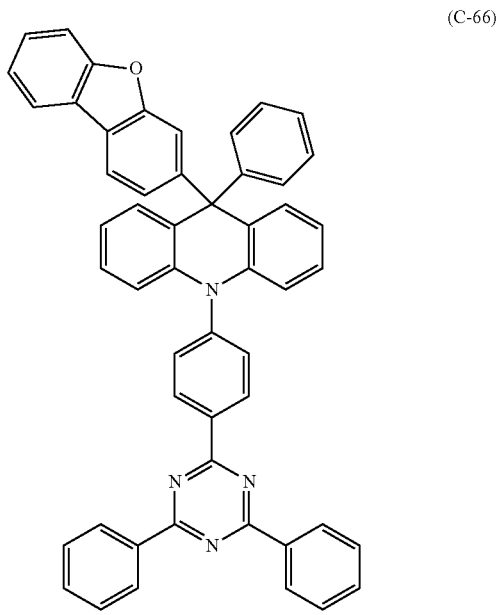 [SMILES: c1ccc(-c2nc(-c3ccccc3)nc(-c3ccc(N4c5ccccc5C(c5ccccc5)(c5ccc6c(c5)oc5ccccc56)c5ccccc54)cc3)n2)cc1]
(C-66)

The synthesis route for the 9,10-dihydro-acridine derivative of Formula C-66 is shown below:

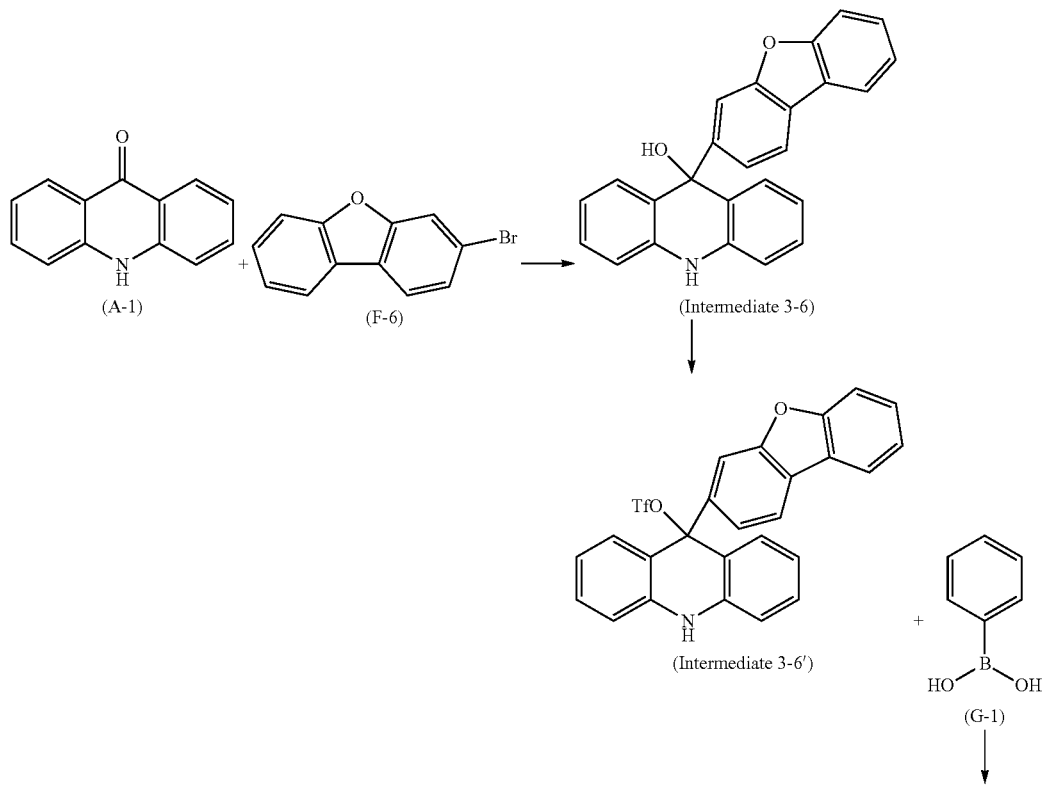

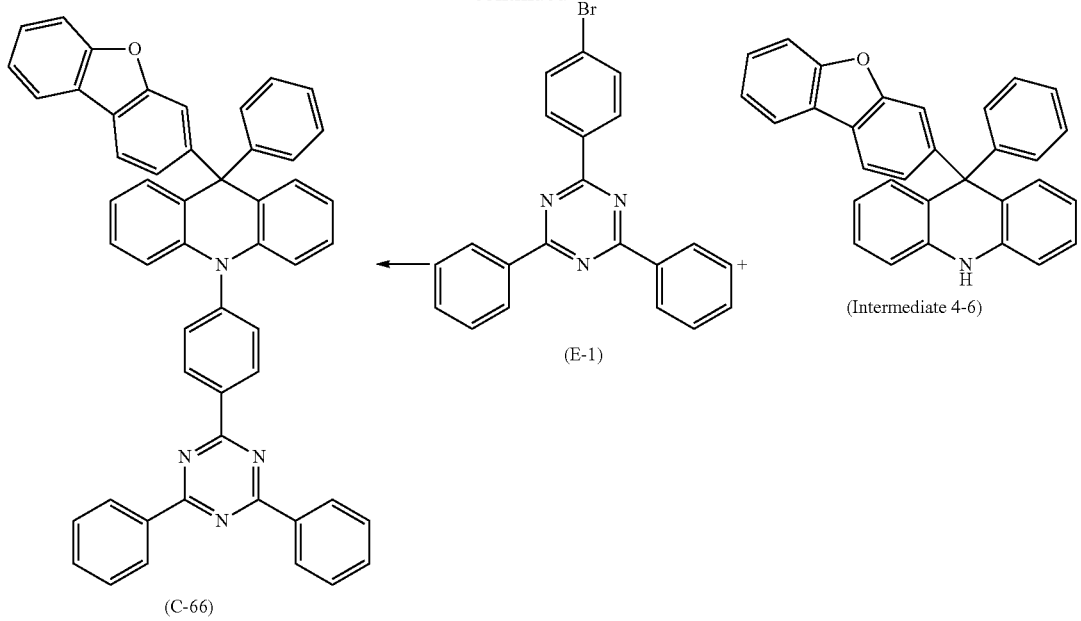

(C-66)

(E-1)

(Intermediate 4-6)

The preparation steps of the 9,10-dihydro-acridine derivative of Formula C-66 were the same as those for the 9,10-dihydro-acridine derivative of Formula C-55 provided in Example 46, except that:

the compound F-1 in Step (1) of Example 46 was replaced by the compound of Formula F-6. The yield was 84%.

Example 56

This example provides a 9,10-dihydro-acridine derivative having a structure of Formula C-67:

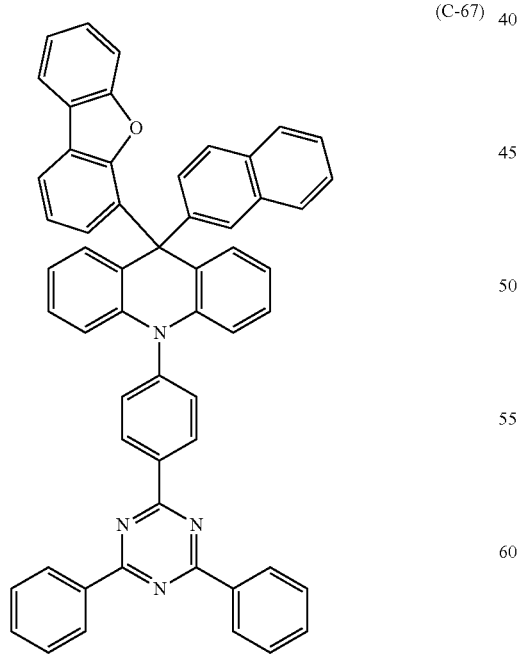

(C-67)

The synthesis route for the 9,10-dihydro-acridine derivative of Formula C-67 is shown below:

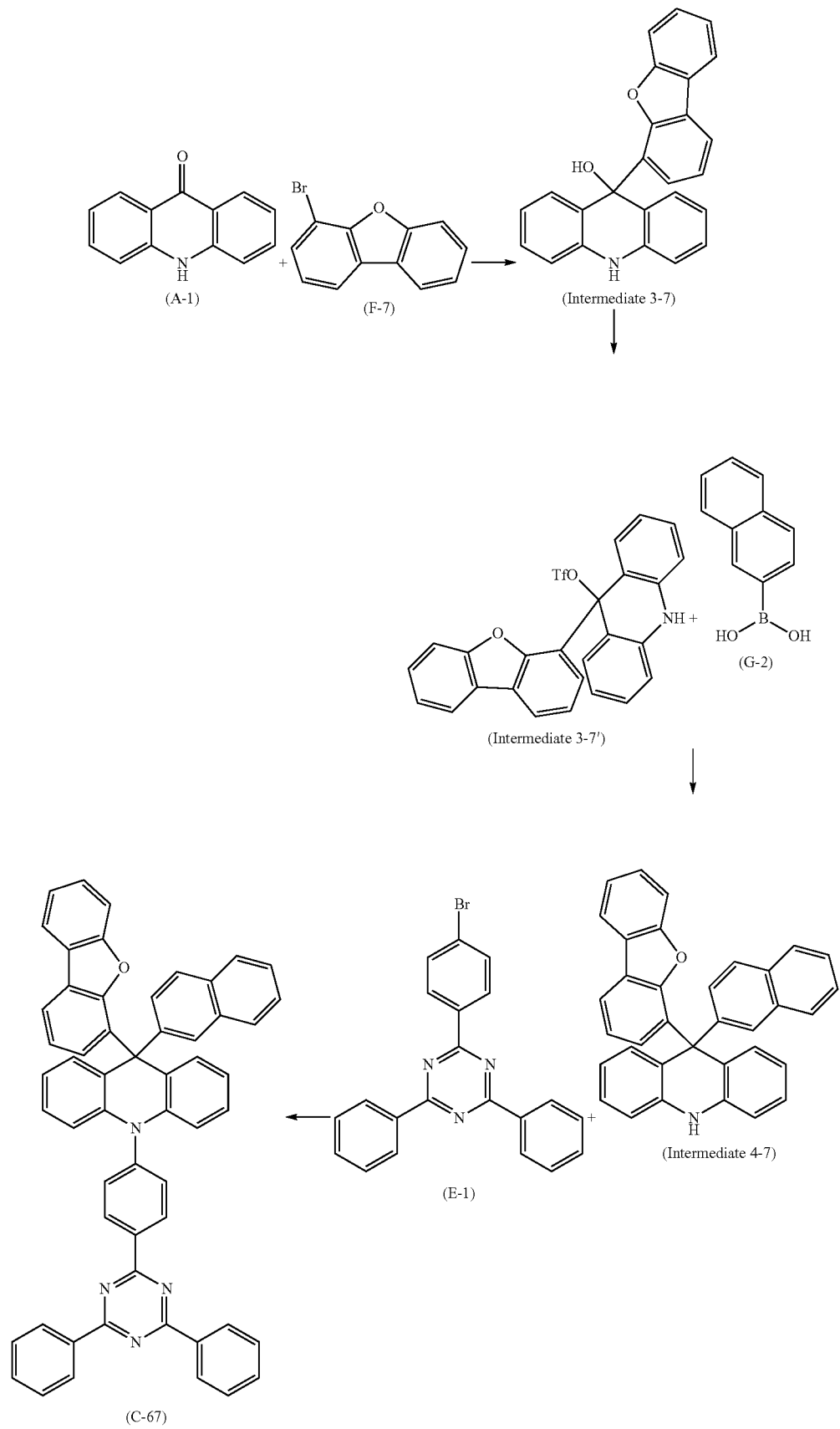

The method for preparing the 9,10-dihydro-acridine derivative of Formula C-55 comprises specifically the following steps.

(1) Synthesis of Intermediate 3-7

Under nitrogen atmosphere, the compound F-7 (16.8 g, 100 mmol), and tetrahydrofuran (500 mL) were added. At −78° C., n-butyl lithium (63 mL, 1.6 M) was added dropwise, reacted for 30 min at a low temperate and then for 3 hrs at an elevated temperature of 30° C., and then cooled to −78° C. A solution of 9(10H)-acridone (the compound A-1) (500 mL, 0.2 M, 9.5 g (100 mmol)) was added, slowly heated to 30° C., reacted for 15 hrs, and then quenched by adding an aqueous ammonium chloride solution. The reaction solution was extracted with chloroform, and then the solvent was removed by rotary evaporation. The residue was purified by column chromatography on silica gel, to obtain the intermediate 3-7 as a solid (17.3 g, yield 47%).

(2) Synthesis of Intermediate 3-7'

Under nitrogen atmosphere, the compound 3-7 (14.5 g, 40 mmol), triethylamine (5.0 g, 48 mmol), and dichloromethane (400 mL) were added. Trifluoromethanesulfonic anhydride (13.5 g, 48 mmol) was added at −20° C., and reacted at room temperature for 3 hrs. The reaction solution was extracted with toluene (3×), and then the solvent was removed by rotary evaporation. The residue was washed with methanol (3×), to obtain the compound 3-7' (17 g, yield: 87%).

(3) Synthesis of Intermediate 4-7

Under nitrogen atmosphere, the compound 3-7' (14.8 g, 30 mmol), the compound G-2 (5.2 g, 30 mmol), potassium phosphate (70 g, 33 mmol), tetrakis(triphenylphosphine) palladium (1.7 g, 1.5 mmol), water (50 mL), and 1,4-dioxane (300 mL) were added, reacted at 120° C. for 8 hrs, and then cooled to room temperature. The reaction solution was extracted with chloroform, and then the solvent was removed by rotary evaporation. The residue was purified by column chromatography on silica gel, to obtain the solid compound 4-7 (11.1 g, yield 77%).

(4) Synthesis of 9,10-dihydro-acridine Derivative C-67

Under nitrogen atmosphere, the compound 4-7 (9.5 g, 20 mmol), palladium diacetate (0.13 g, 0.6 mmol), tri-tert-butylphosphine (0.45 g, 2.2 mmol), the compound E-1 (8.5 g, 22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-67 (12.6 g, yield 81%).

Element analysis: (C56H36N4O) calculated: C, 86.13; H, 4.65; N, 7.17; O, 2.05. found: C, 86.10; H, 4.67; N, 7.13; O, 2.09, HRMS (ESI) m/z (M+): calculated: 780.2889. found: 780.2893.

Example 57

This example provides a 9,10-dihydro-acridine derivative having a structure of Formula C-70:

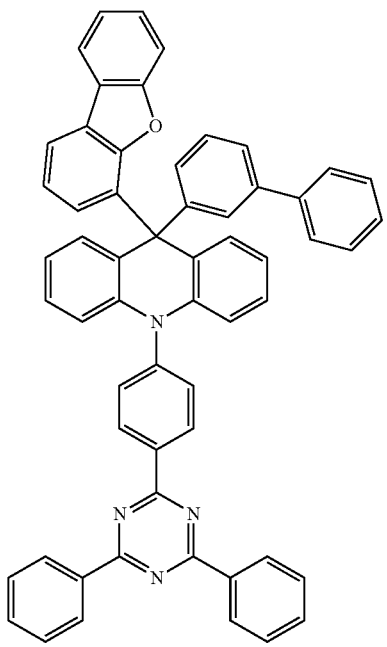

(C-70)

The synthesis route for the 9,10-dihydro-acridine derivative of Formula C-70 is shown below:

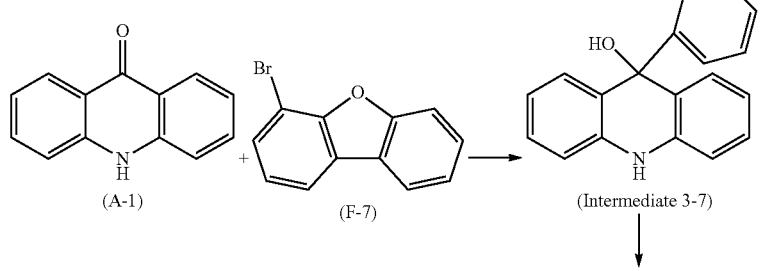

-continued
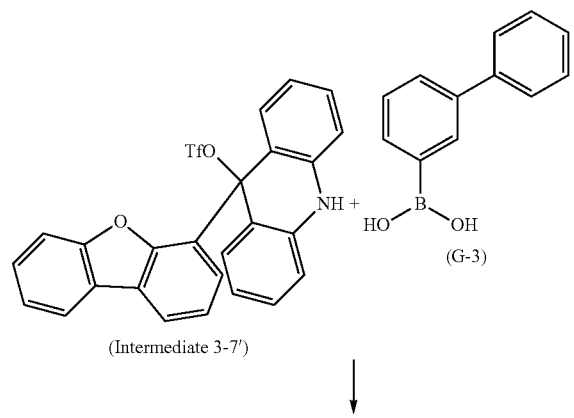
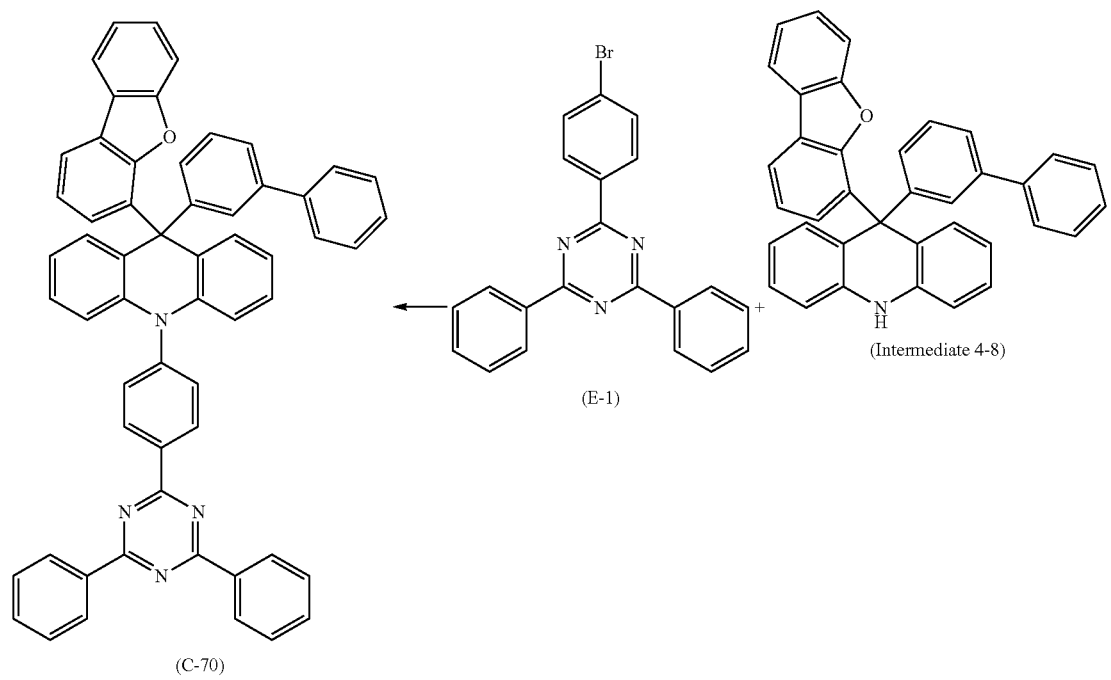

The preparation steps of the 9,10-dihydro-acridine derivative of Formula C-70 were the same as those for the 9,10-dihydro-acridine derivative of Formula C-67 provided in Example 56, except that:

the compound G-2 in Step (3) of Example 56 was replaced by the compound of Formula G-3. The yield was 76%.

Example 58

This example provides a 9,10-dihydro-acridine derivative having a structure of Formula C-71:

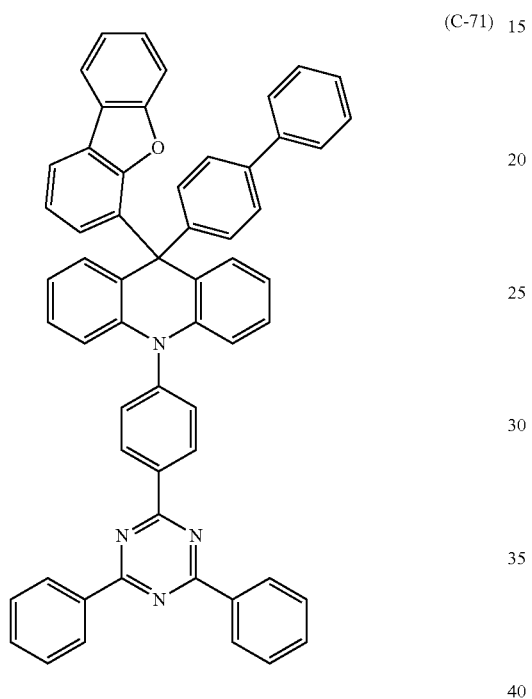

(C-71)

The synthesis route for the 9,10-dihydro-acridine derivative of Formula C-71 is shown below:

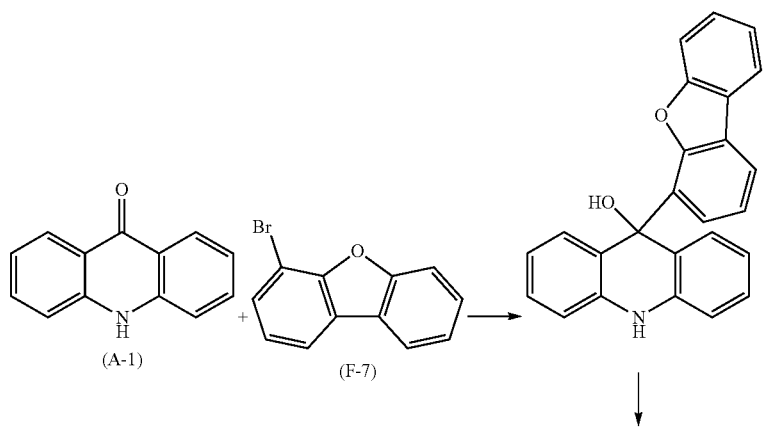

-continued
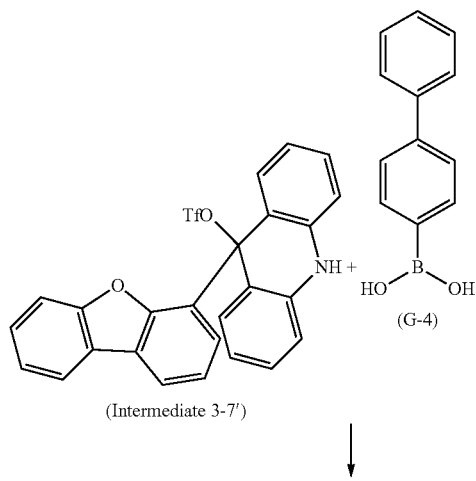
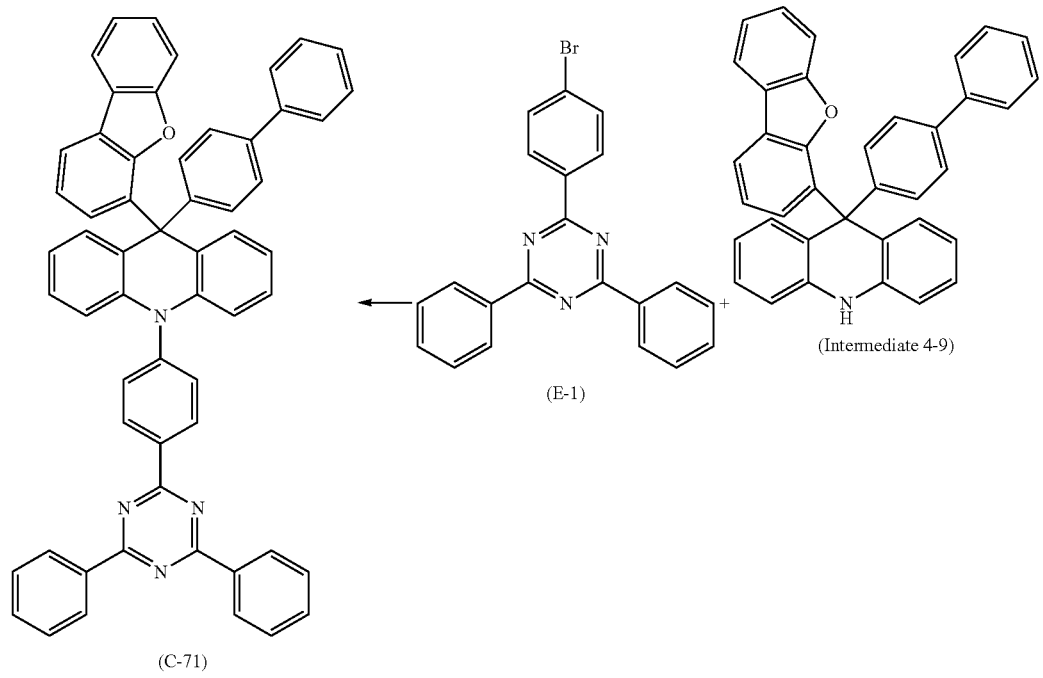

The preparation steps of the 9,10-dihydro-acridine derivative of Formula C-71 were the same as those for the 9,10-dihydro-acridine derivative of Formula C-67 provided in Example 56, except that:

the compound G-2 in Step (3) of Example 56 was replaced by the compound of Formula G-4. The yield was 78%.

Example 59

This example provides a 9,10-dihydro-acridine derivative having a structure of Formula C-72:

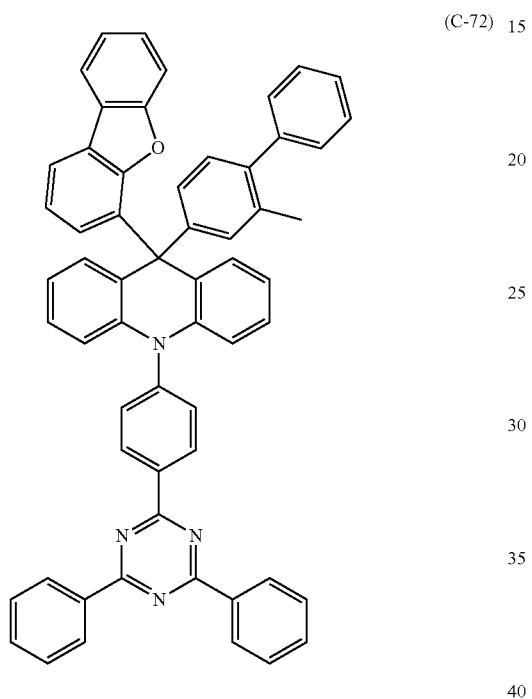

(C-72)

The synthesis route for the 9,10-dihydro-acridine derivative of Formula C-72 is shown below:

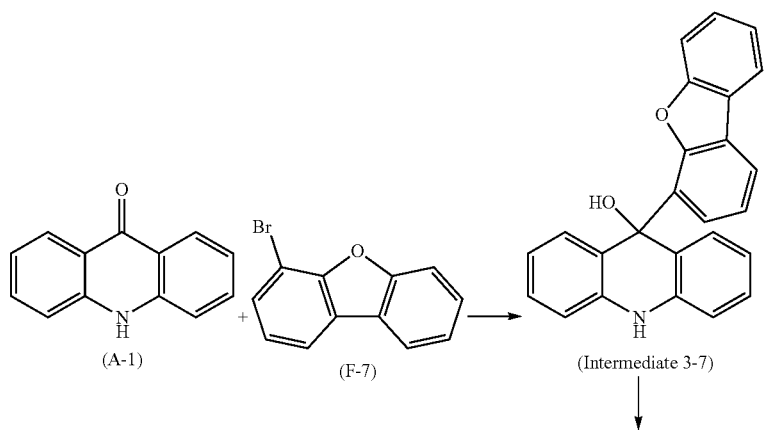

-continued
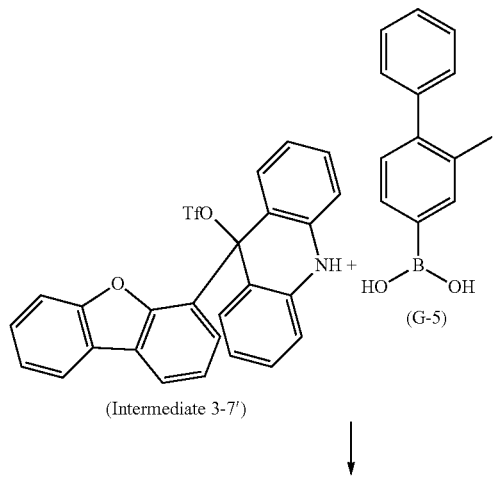
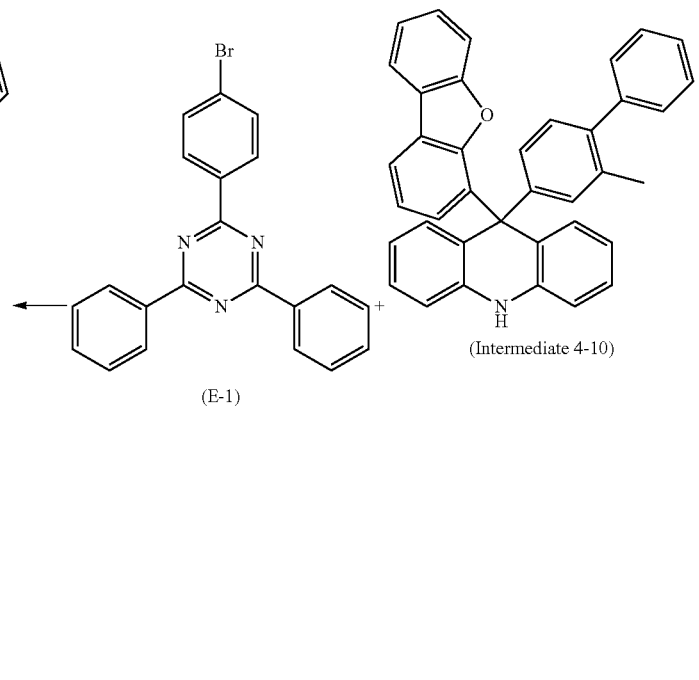

The preparation steps of the 9,10-dihydro-acridine derivative of Formula C-72 were the same as those for the 9,10-dihydro-acridine derivative of Formula C-67 provided in Example 56, except that:

the compound G-2 in Step (3) of Example 56 was replaced by the compound of Formula G-5. The yield was 86%.

Example 60

This example provides a 9,10-dihydro-acridine derivative having a structure of Formula C-73:

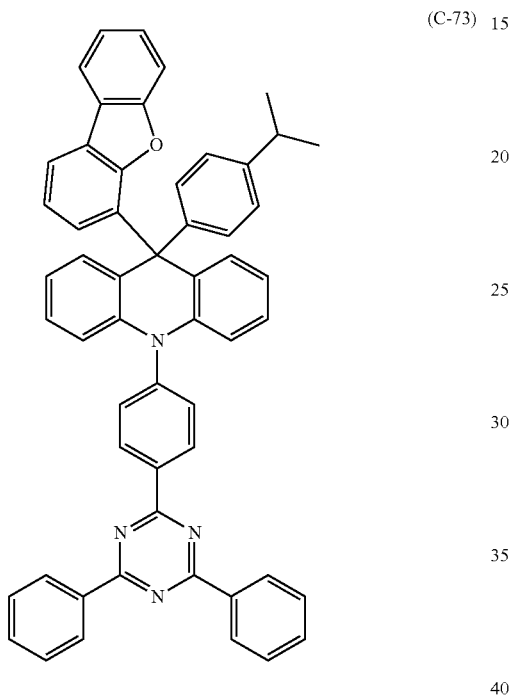

(C-73)

The synthesis route for the 9,10-dihydro-acridine derivative of Formula C-73 is shown below:

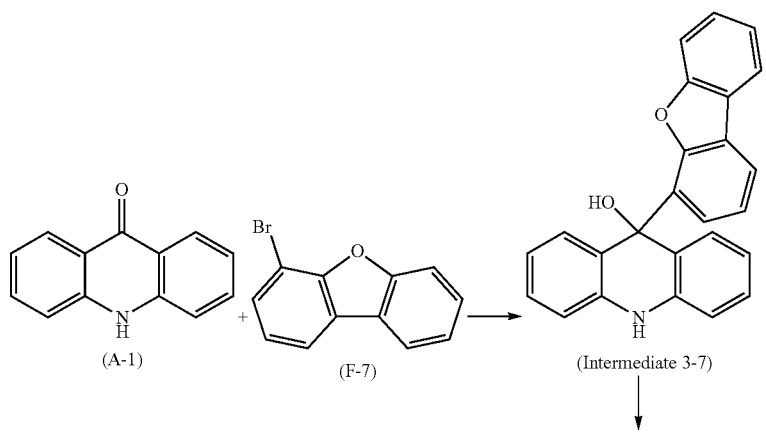

-continued
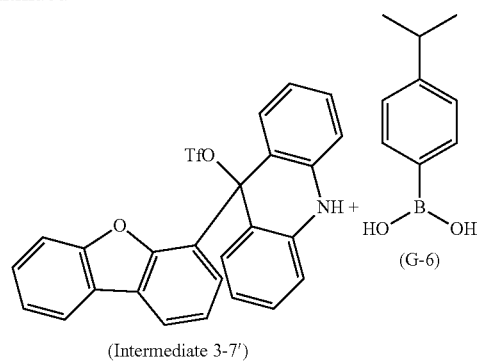
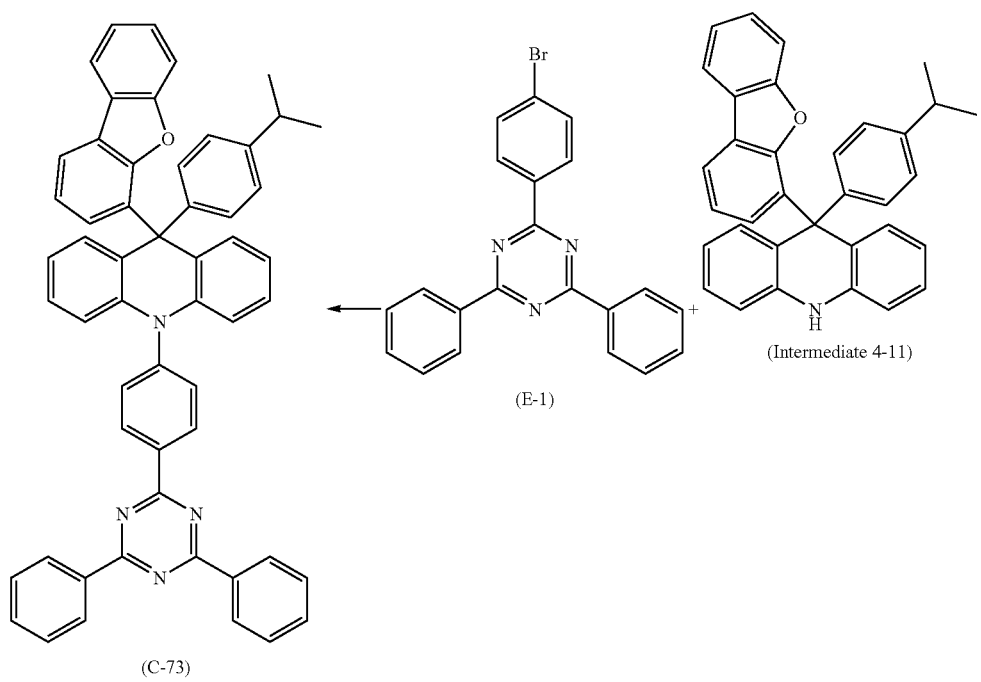

The preparation steps of the 9,10-dihydro-acridine derivative of Formula C-73 were the same as those for the 9,10-dihydro-acridine derivative of Formula C-67 provided in Example 56, except that:

the compound G-2 in Step (3) of Example 56 was replaced by the compound of Formula G-6. The yield was 81%.

Example 61

This example provides a 9,10-dihydro-acridine derivative having a structure of Formula C-75:

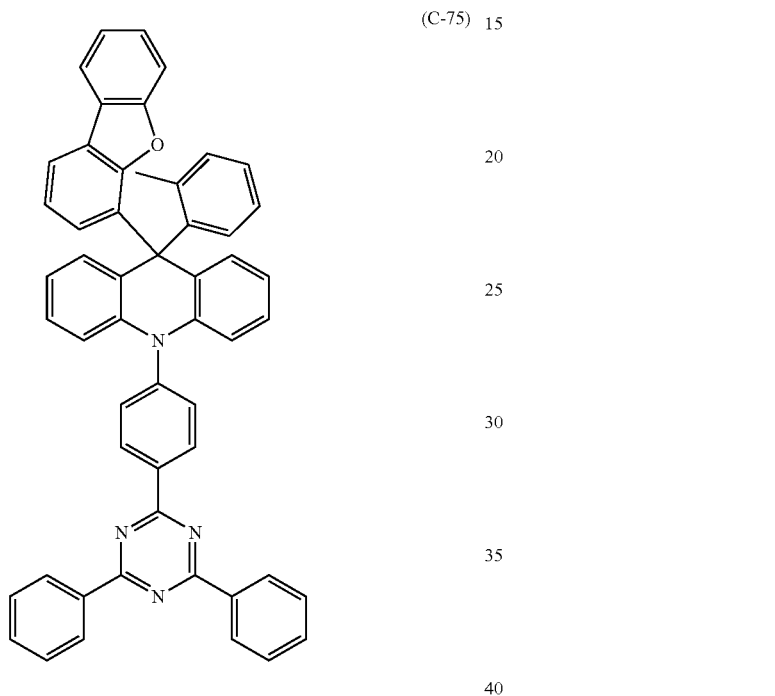

(C-75)

The synthesis route for the 9,10-dihydro-acridine derivative of Formula C-75 is shown below:

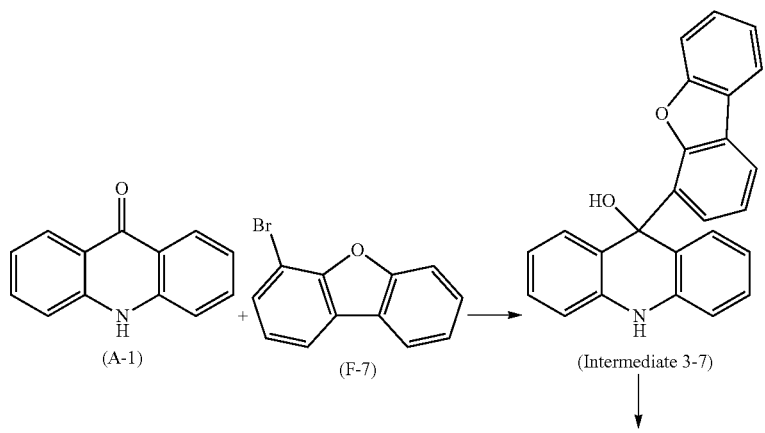

-continued
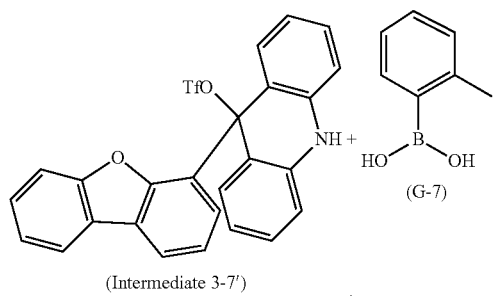
(Intermediate 3-7')  (G-7)
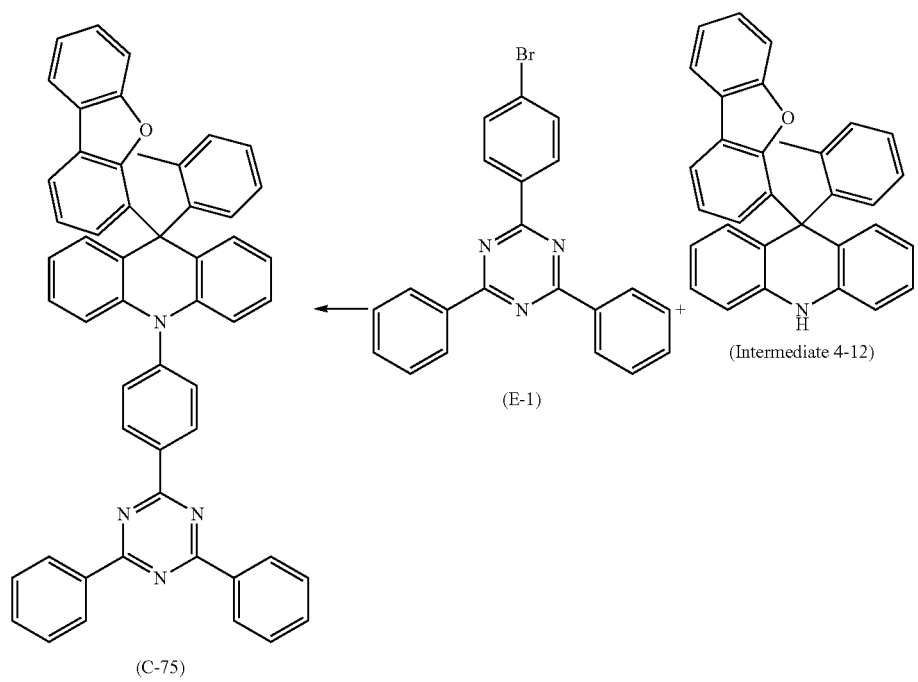
(C-75)  (E-1)  (Intermediate 4-12)

The preparation steps of the 9,10-dihydro-acridine derivative of Formula C-75 were the same as those for the 9,10-dihydro-acridine derivative of Formula C-67 provided in Example 56, except that:

the compound G-2 in Step (3) of Example 56 was replaced by the compound of Formula G-7. The yield was 80%.

Example 62

This example provides a 9,10-dihydro-acridine derivative having a structure of Formula C-78:

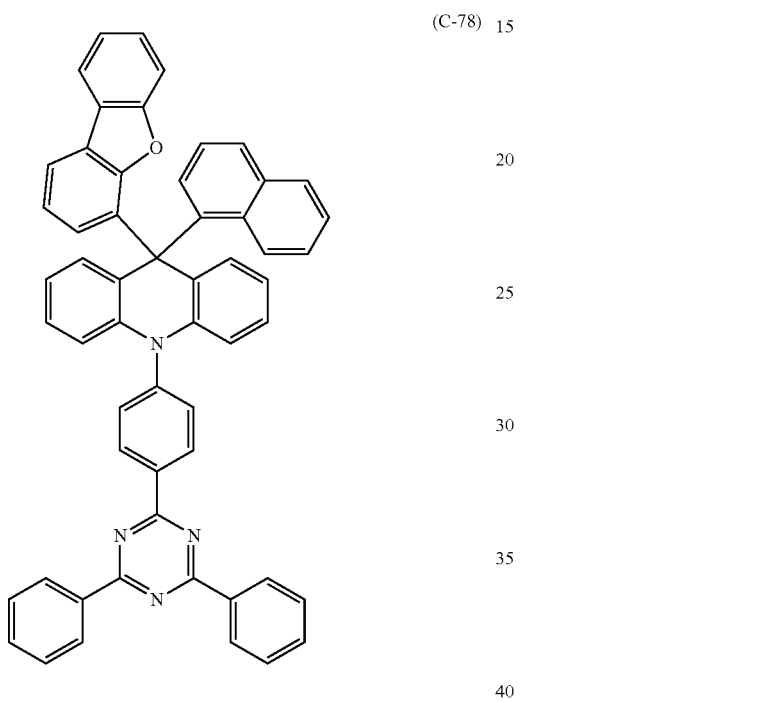

(C-78)

The synthesis route for the 9,10-dihydro-acridine derivative of Formula C-78 is shown below:

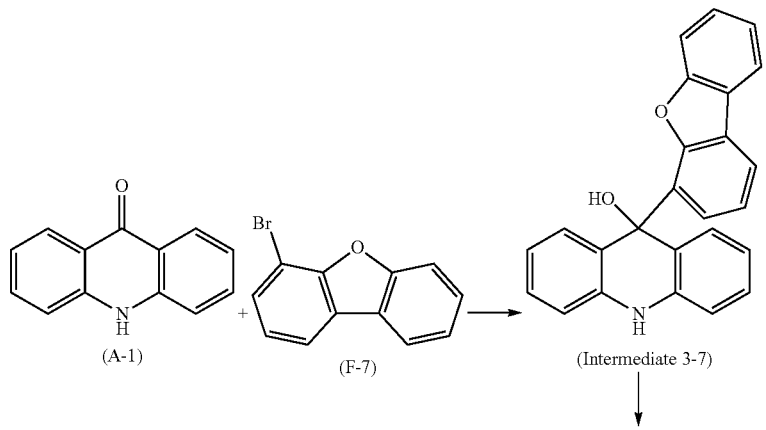

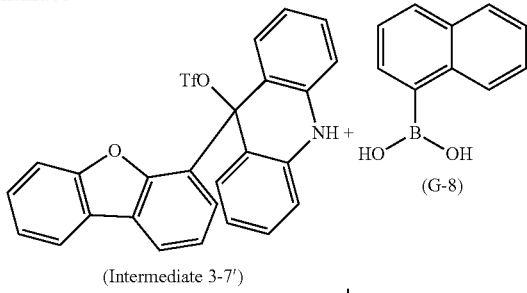

(Intermediate 3-7')

(G-8)

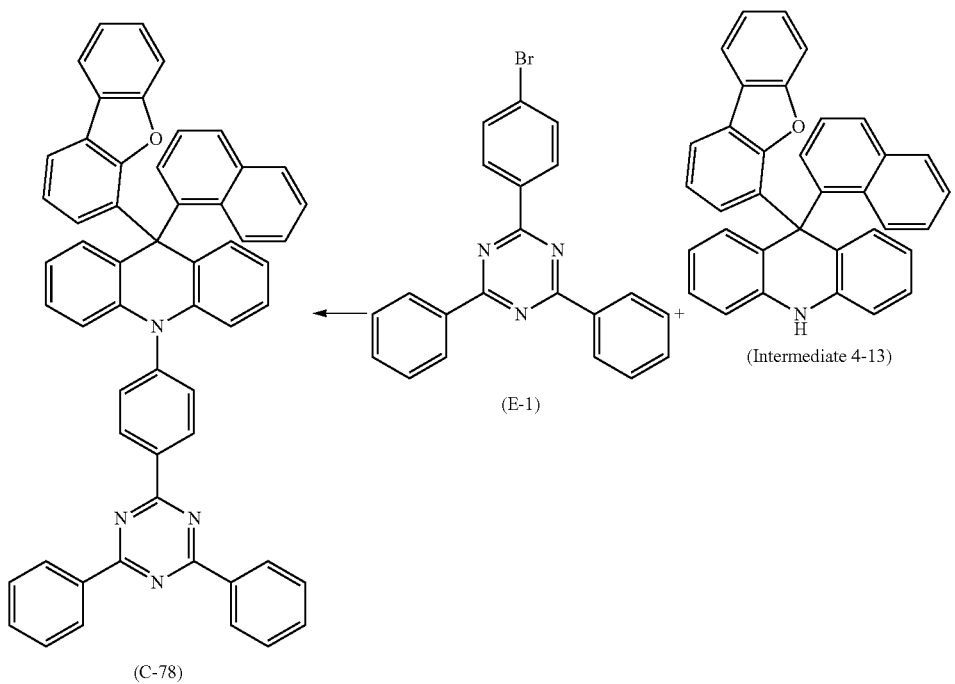

(C-78)

(E-1)

(Intermediate 4-13)

The preparation steps of the 9,10-dihydro-acridine derivative of Formula C-78 were the same as those for the 9,10-dihydro-acridine derivative of Formula C-67 provided in Example 56, except that:

the compound G-2 in Step (3) of Example 56 was replaced by the compound of Formula G-8. The yield was 82%.

Example 63

This example provides a 9,10-dihydro-acridine derivative having a structure of Formula C-80:

(C-80)
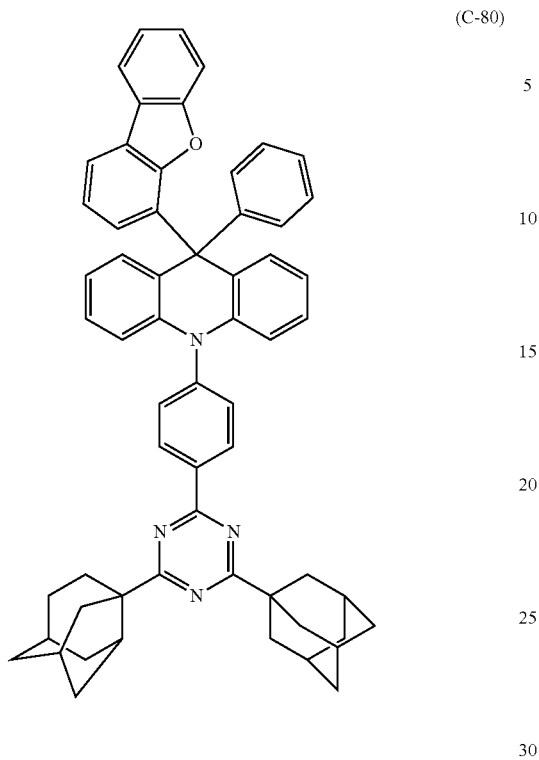
The synthesis route for the 9,10-dihydro-acridine derivative of Formula C-80 is shown below:
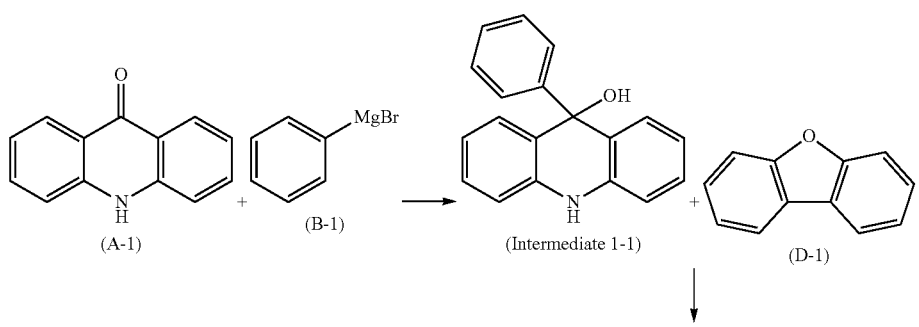

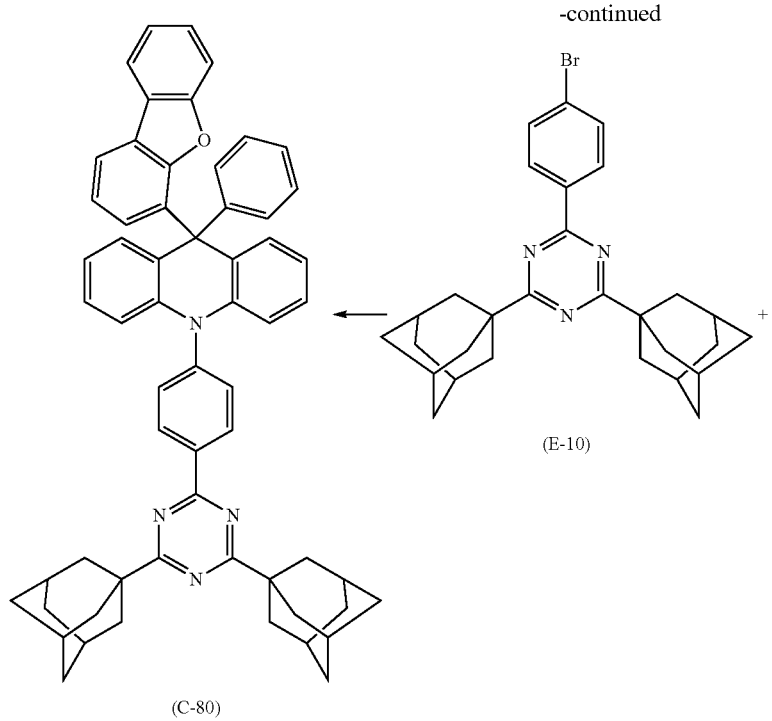

(C-80)

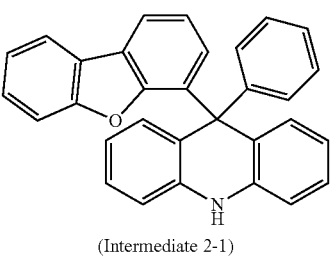

(E-10)

(Intermediate 2-1)

The method for preparing the 9,10-dihydro-acridine derivative of Formula C-80 comprises specifically the following steps.

(1) Synthesis of Intermediate 1-1

Under nitrogen atmosphere, 9(10H)-acridone (the compound A-1) (19.5 g, 100 mmol) and tetrahydrofuran (700 mL) were added to a 1 L three-neck flask. A phenyl magnesium bromide (the compound B-1) solution (110 mL, 1 M) was added at −20° C., reacted at room temperature for 8 hrs, and then quenched by adding an aqueous ammonium chloride solution. The reaction solution was extracted with dichloromethane (3×), and then the solvent was removed by rotary evaporation. The residue was purified by column chromatography on silica gel, to obtain the Intermediate 1-1 as a solid (24 g, yield: 88%);

(2) Synthesis of Intermediate 2-1

Under nitrogen atmosphere, the compound 1-1 (22.0 g, 80 mmol), dibenzofuran (the compound D-1) (27 g, 160 mmol), and dichloromethane (600 mL) were added to a 1 L three-neck flask. Eaton's Reagent (1.8 mL, 0.9 M) was added dropwise, reacted at room temperature for 30 min, and then quenched by adding a sodium bicarbonate solution. The reaction solution was extracted with toluene (3×), and then the solvent was removed by rotary evaporation. The residue was purified by column chromatography on silica gel, to obtain the intermediate 2-1 as a solid (13.5 g, yield: 40%).

(3) Synthesis of 9,10-dihydro-acridine Derivative C-80

Under nitrogen atmosphere, the compound 2-1 (8.5 g, 20 mmol), palladium diacetate (0.13 g, 0.6 mmol), tri-tert-butylphosphine (0.45 g, 2.2 mmol), the compound E-10 (22 mmol), sodium-t-butoxide (5.7 g), and toluene (300 mL) were added, reacted at 110° C. for 12 hrs, and then cooled to room temperature. The reaction solution was extracted with chloroform, and then the solvent was removed by rotary evaporation. The residue was purified by column chromatography on silica gel, to obtain the solid compound C-80 (14.2 g, yield 84%).

Element analysis: (C60H54N4O) calculated: C, 85.07; H, 6.43; N, 6.61; O, 1.89. found: C, 85.02; H, 6.46; N, 6.57; O, 1.92, HRMS (ESI) m/z (M+): calculated: 846.4297. found: 846.4271.

The compound E-10 was synthesized through the following steps:

Under nitrogen atmosphere, the compound E-10-1 (21.8 g, 100 mmol), dichloromethane (150 mL), and the compound E-10-2 (32 g, 200 mmol) were added, and reacted at 0° C. for 30 min. A solution of antimony pentachloride in dichloromethane (108 mL, 1 M) was added dropwise, reacted at room temperature for 2 hrs and then at 45° C. for 40 hrs, and cooled to room temperature. The resulting solid was filtered out, added slowly to aqueous ammonium (500 mL, 30%) at 0° C., and stirred at room temperature for 20 hrs. The solid was filtered out, washed with water, and dried. The solid insoluble in toluene was further removed, and the product was washed with acetone, and dried to obtain the solid compound E-10 (16.3 g, yield 34%).

The synthesis route for the compound E-10 is shown below:

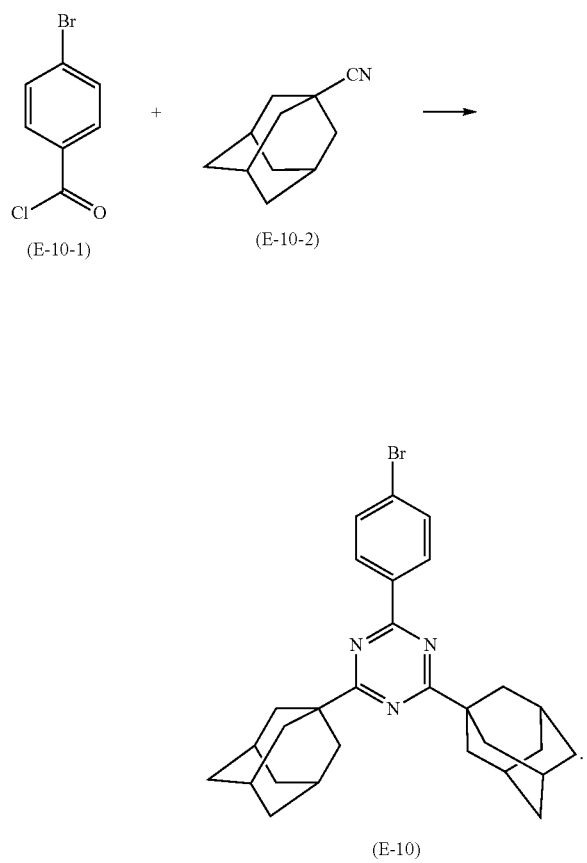 [SMILES: O=C(Cl)c1ccc(Br)cc1 ; N#CC12CC3CC(CC(C3)C1)C2 ; Brc1ccc(-c2nc(C34CC5CC(CC(C5)C3)C4)nc(C34CC5CC(CC(C5)C3)C4)n2)cc1]
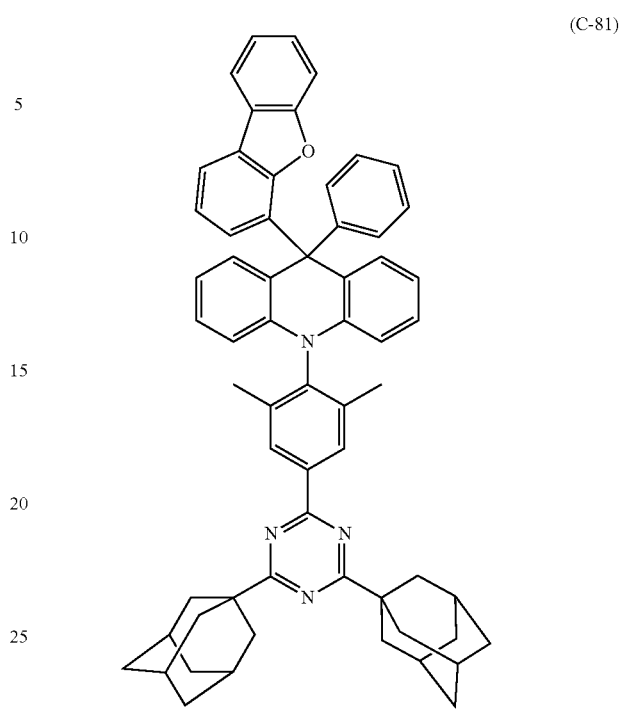
Example 64
This example provides a 9,10-dihydro-acridine derivative having a structure of Formula C-81:
The synthesis route for the 9,10-dihydro-acridine derivative of Formula C-81 is shown below:
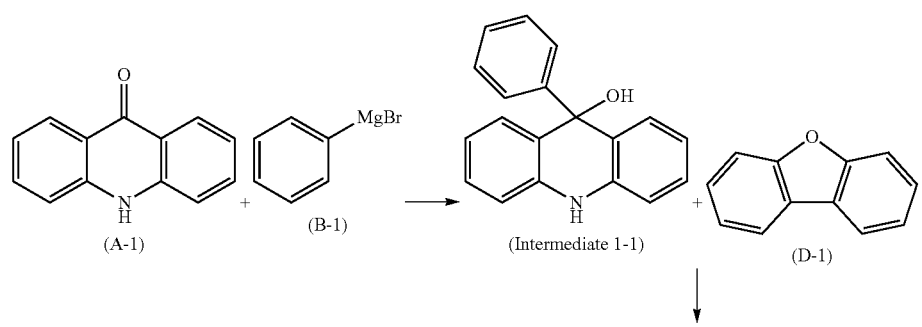

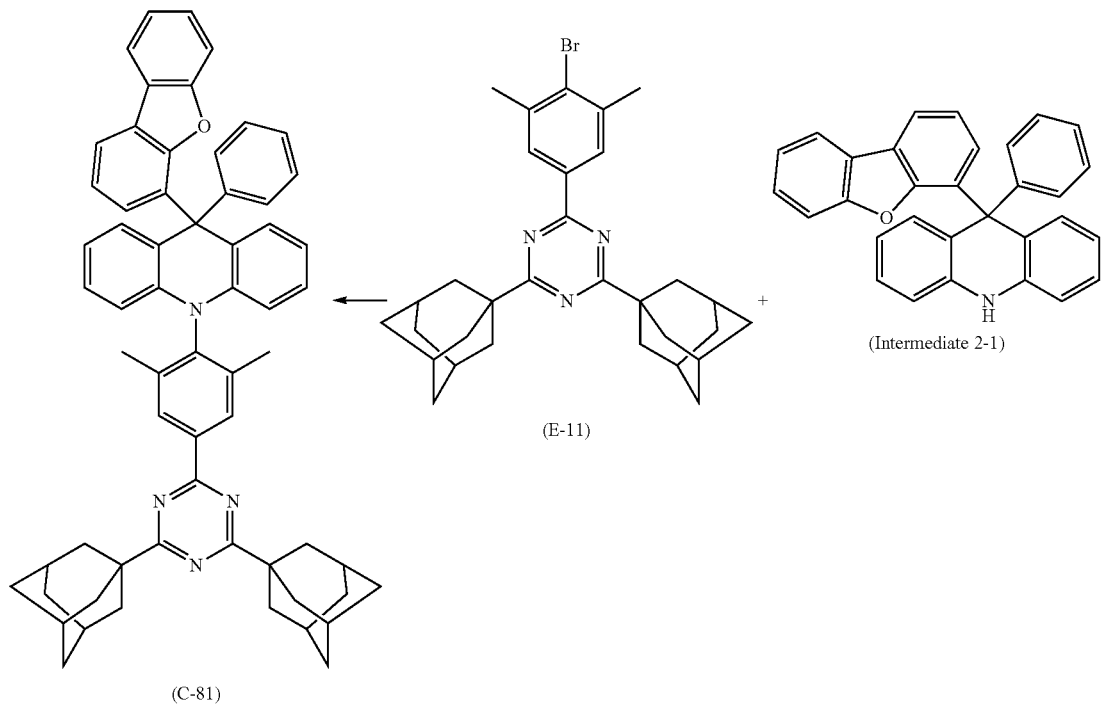

(C-81)  (E-11)  (Intermediate 2-1)

The preparation steps of the 9,10-dihydro-acridine derivative of Formula C-81 were the same as those for the 9,10-dihydro-acridine derivative of Formula C-80 provided in Example 63, except that:

the compound E-10 in Step (3) of Example 63 was replaced by the compound of Formula E-11. The yield was 81%.

Element analysis: (C62H58N4O) calculated: C, 85.09; H, 6.68; N, 6.40; O, 1.83. found: C, 85.06; H, 6.70; N, 6.38; O, 1.87, HRMS (ESI) m/z (M+): calculated: 874.4610. found: 874.4571.

Example 65

This example provides a 9,10-dihydro-acridine derivative having a structure of Formula C-82:

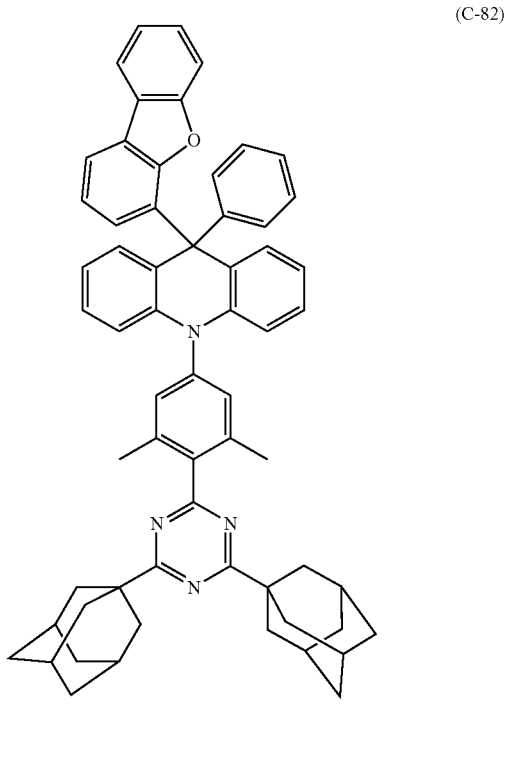 [SMILES: Cc1cc(N2c3ccccc3C(c3ccccc3)(c3cccc4c3oc3ccccc34)c3ccccc32)cc(C)c1-c1nc(C23CC4CC(CC(C4)C2)C3)nc(C23CC4CC(CC(C4)C2)C3)n1]
(C-82)
The synthesis route for the 9,10-dihydro-acridine derivative of Formula C-82 is shown below:
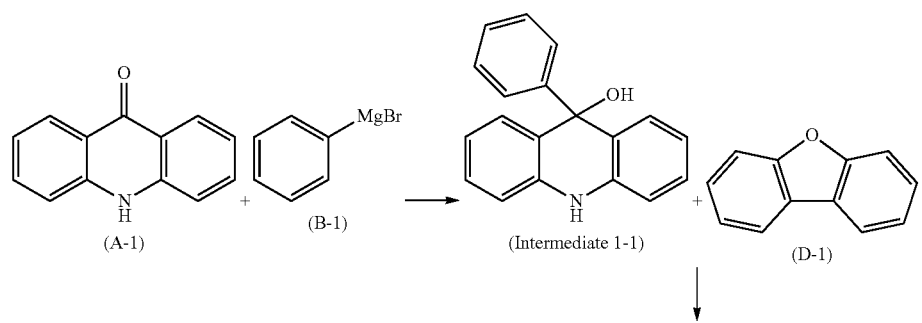

-continued

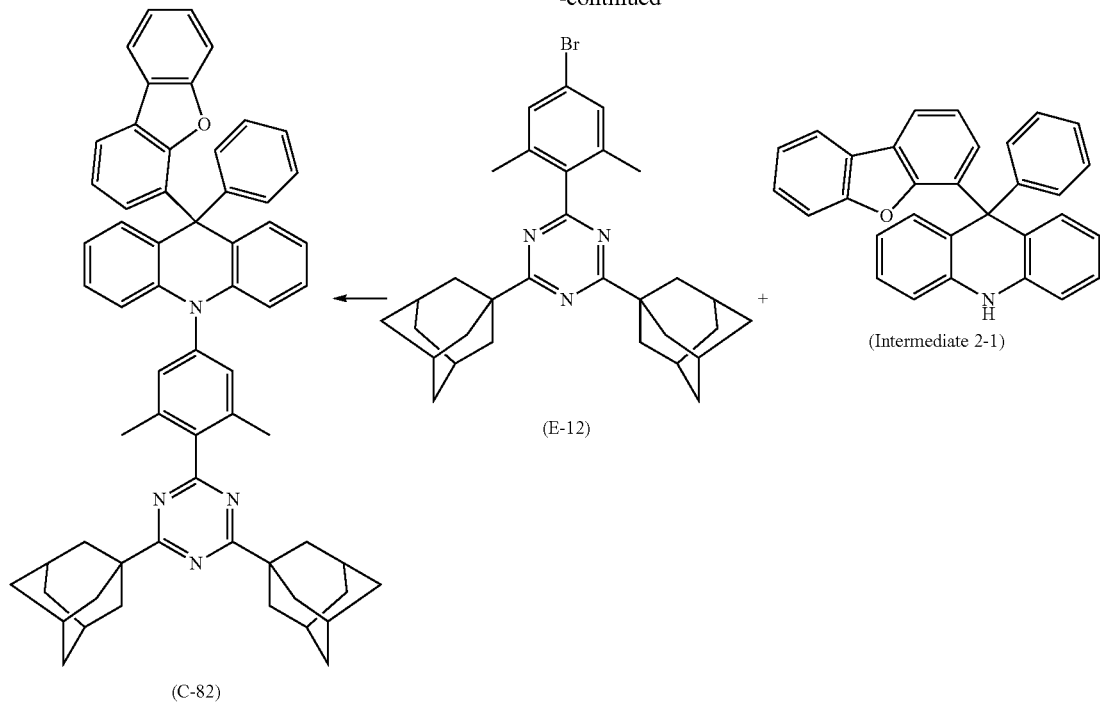

(C-82)

(E-12)

(Intermediate 2-1)

The preparation steps of the 9,10-dihydro-acridine derivative of Formula C-82 were the same as those for the 9,10-dihydro-acridine derivative of Formula C-80 provided in Example 63, except that:

the compound E-10 in Step (3) of Example 63 was replaced by the compound of Formula E-12. The yield was 85%.

Element analysis: (C62H58N4O) calculated: C, 85.09; H, 6.68; N, 6.40; O, 1.83. found: C, 85.07; H, 6.73; N, 6.32; O, 1.89, HRMS (ESI) m/z (M+): calculated: 874.4610. found: 874.4607.

Example 66

This example provides a 9,10-dihydro-acridine derivative having a structure of Formula C-90:

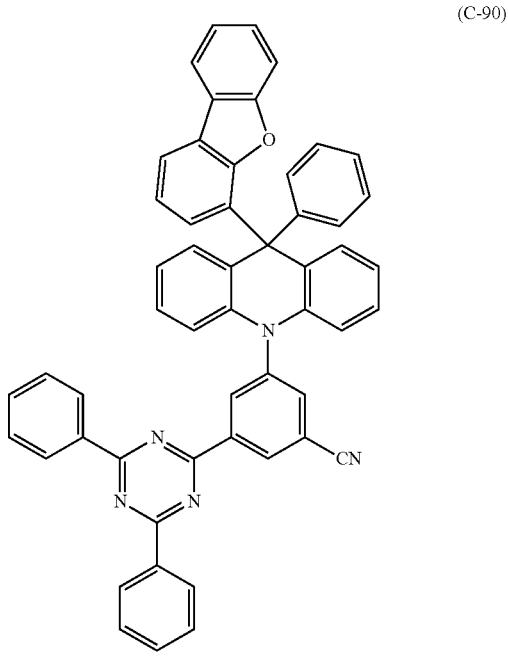 [SMILES: N#Cc1cc(-c2nc(-c3ccccc3)nc(-c3ccccc3)n2)cc(N2c3ccccc3C(c3ccccc3)(c3cccc4c3oc3ccccc34)c3ccccc32)c1]
(C-90)
The synthesis route for the 9,10-dihydro-acridine derivative of Formula C-90 is shown below:
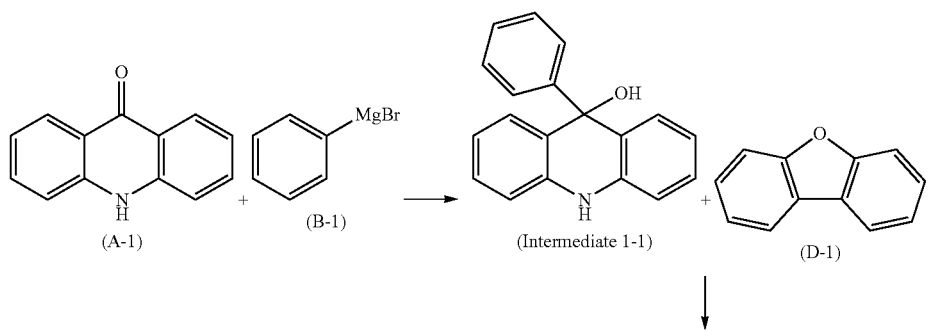

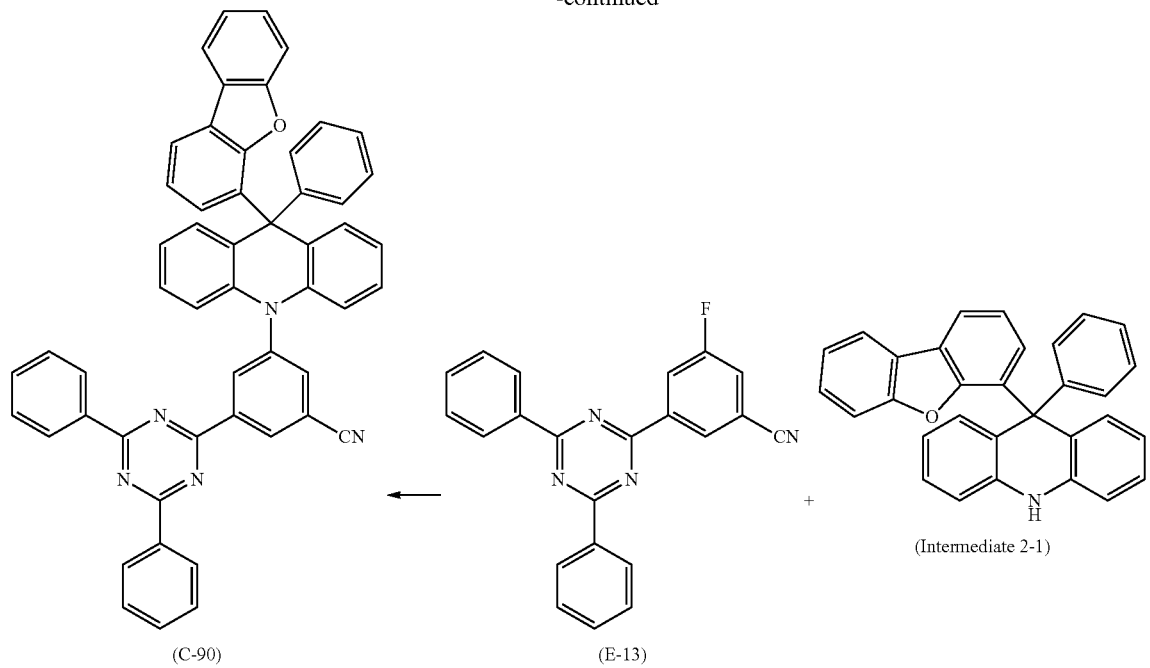

(C-90) ← (E-13) + (Intermediate 2-1)

The preparation steps of the 9,10-dihydro-acridine derivative of Formula C-90 were the same as those for the 9,10-dihydro-acridine derivative of Formula C-80 provided in Example 63, except that:

the compound E-10 in Step (3) of Example 63 was replaced by the compound of Formula E-13. The yield was 64%.

Element analysis: (C53H33N5O) calculated: C, 84.22; H, 4.40; N, 9.27; O, 2.12. found: C, 84.18; H, 4.43; N, 9.28; O, 2.13, HRMS (ESI) m/z (M+): calculated: 755.2685. found: 755.2697.

Example 67

Figure 2:
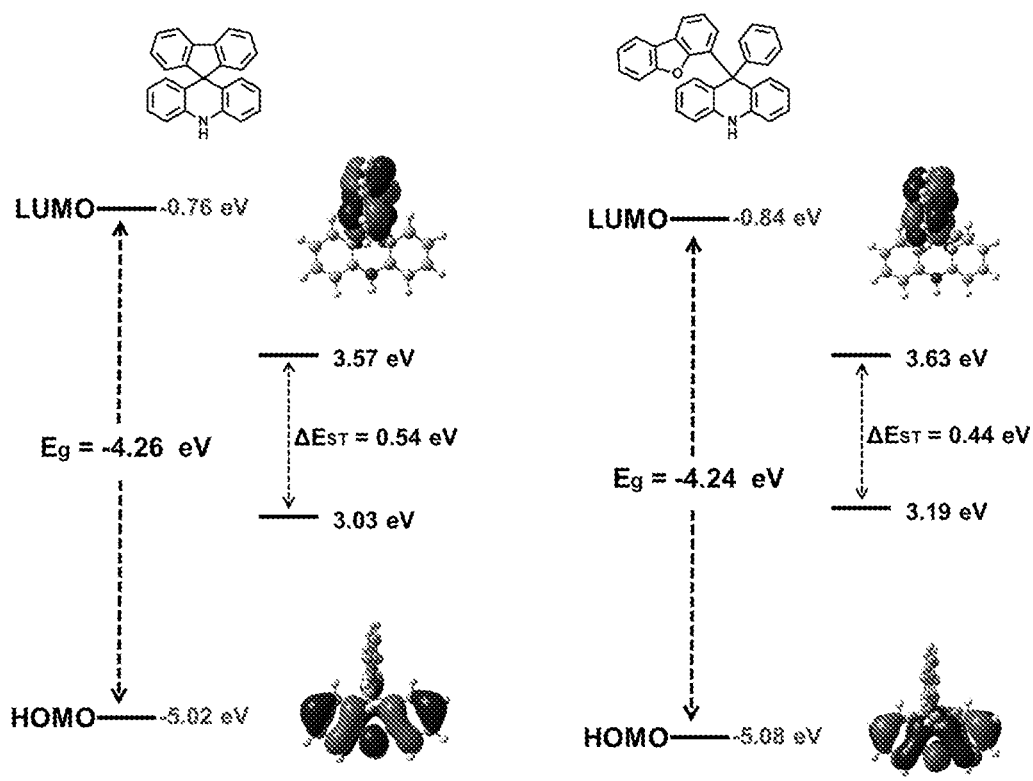
FIG. 2 compares the theoretical calculation results of the singlet energy levels, the triplet energy levels, and the ΔEst of the electron donating groups in the compound of Formula C-1 provided in Example 1 of the present invention and the compound of Formula II-1 provided in Comparative Example 2.

This example provides an organic light-emitting device, which includes, from bottom to top, an anode 1, a hole injection layer 1, a hole transport layer 3, a light emitting layer 4, an electron transport layer 5, an electron injection layer 6 and a cathode 7 stacked in sequence, as shown in FIG. 2.

In the organic light-emitting device, the material of the anode is ITO; and the material of the cathode 7 is the metal Al.

The material of the hole injection layer 2 is HAT(CN)6, having a chemical structure as shown below:

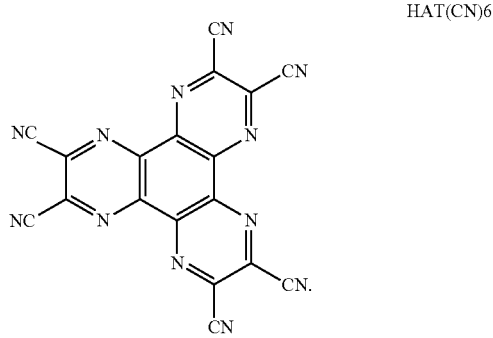

The material of the hole transport layer 3 is a compound having a structure below:

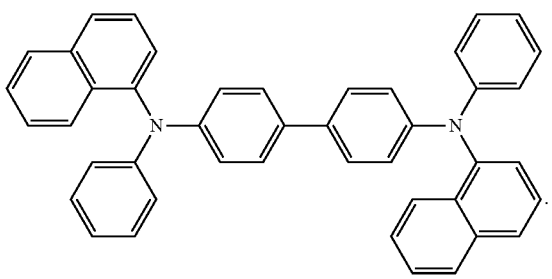 [SMILES: c1ccc(N(c2ccc(-c3ccc(N(c4ccccc4)c4cccc5ccccc45)cc3)cc2)c2cccc3ccccc23)cc1]

The material of the electron transport layer 5 is a compound having a structure below:

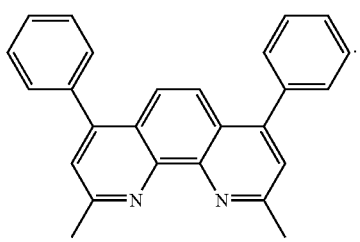 [SMILES: Cc1cc(-c2ccccc2)c2ccc3c(-c4ccccc4)cc(C)nc3c2n1]

The material of the electron injection layer 6 is formed by a compound having a structure below, blended with the electron injection material LiF:

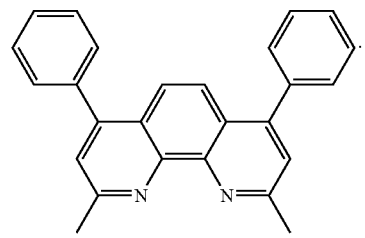 [SMILES: Cc1cc(-c2ccccc2)c2ccc3c(-c4ccccc4)cc(C)nc3c2n1]

In the organic light-emitting device, the light emitting layer 32 is formed by blending a host material and a guest luminescent dye, where the host material is the compound BH, and the guest luminescent material is the 9,10-dihydro-acridine derivative (C-1), and the host material and the guest material are blended at a weight ratio of 100:10. The organic light-emitting device is configured to have a particular structure of ITO/hole injection layer (HIL)/hole transport layer (HTL)/organic light emitting layer (BH blended with the compound C-1)/electron transport layer (ETL)/electron injection layer (EIL/LiF)/cathode (Al). The 9,10-dihydro-acridine derivative (C-1) and the compound BH have the following chemical structures:

(BH)

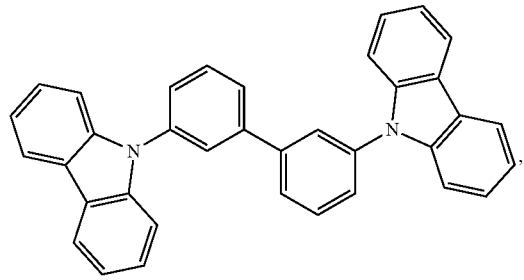

(C-1)

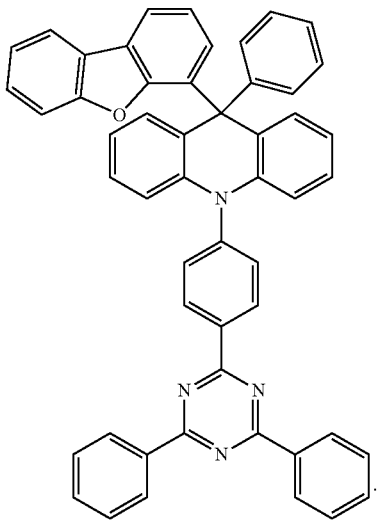

The guest material in the light emitting layer is the compound C-1 has thermally activated delayed fluorescence. The HOMO level and the LUMO level of the TADF material molecule are respectively positioned on different electron donating group

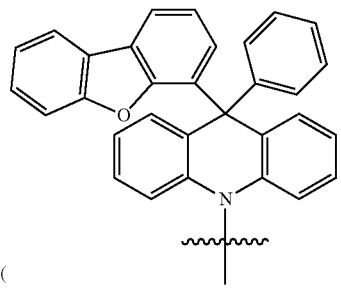

and electron withdrawing group

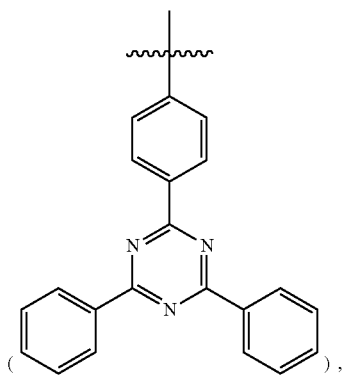 [SMILES: *c1ccc(-c2nc(-c3ccccc3)nc(-c3ccccc3)n2)cc1]

such that the HOMO level and the LUMO level are relatively separated, and the material molecule has a rigid twisted structure, and a small $\Delta E_{ST}$. The triplet excitons of the TADF molecule are converted into singlet excitons by the reverse intersystem crossing, and the singlet excitons fluoresce, achieving a high luminescence efficiency. Furthermore, the dihydro-acridinyl group in the electron donating group is linked to dibenzofuran via a σ bond, to further adjust the S₁ and T₁ of the TADF molecule. FIG. 2 compares the electron donating group formed by connection via a σ bond (the electron donating group in the compound of Formula C-1) and an electron donating group formed by connection in the form of a spirocyclic ring (the electron donating group in the compound of Formula II-1). As can be known from FIG. 2, the

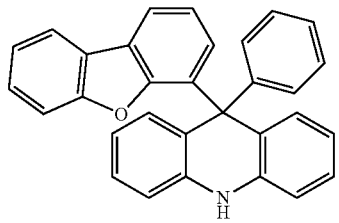 [SMILES: c1ccc(C2(c3cccc4c3oc3ccccc34)c3ccccc3Nc3ccccc32)cc1]

formed by connection via a σ bond provided in the present invention has increased $S_1$ and $T_1$ energy levels, and reduced $\Delta E_{ST}$ compared with the

Figure 3:
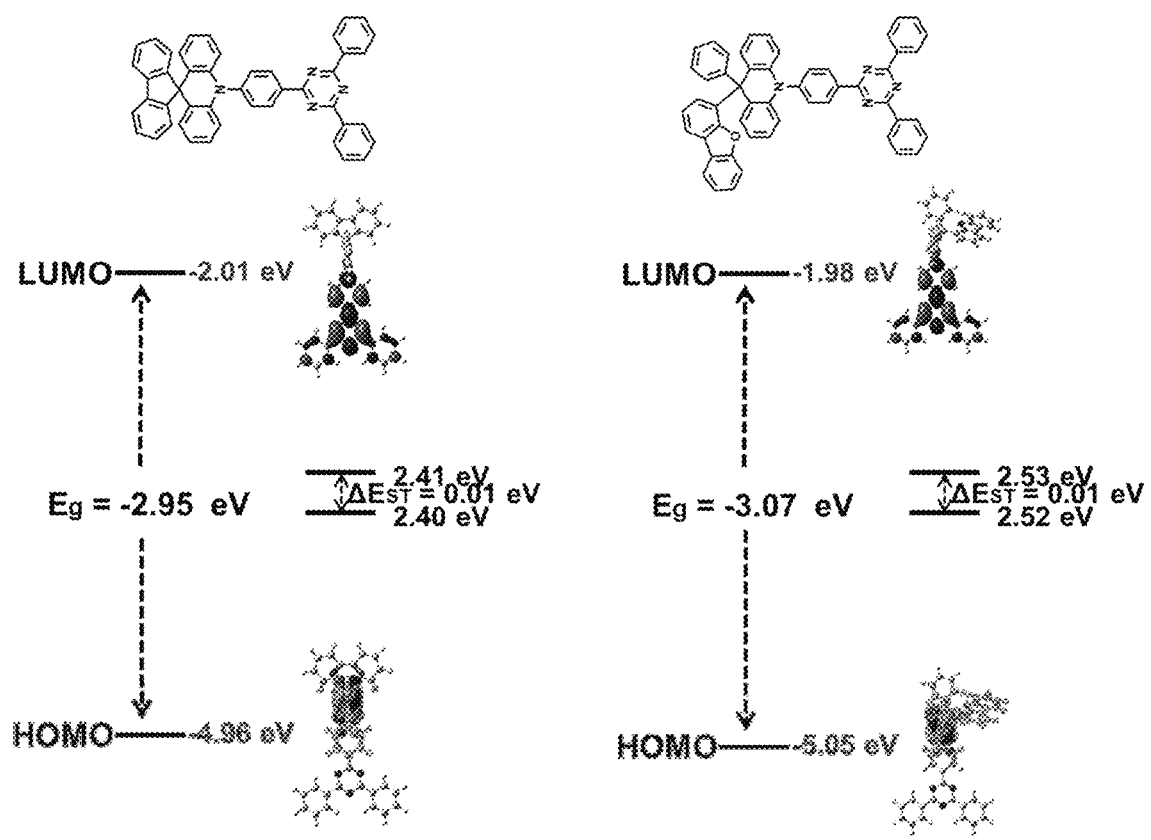
FIG. 3 compares the theoretical calculation results of the singlet energy levels, the triplet energy levels, and the ΔEst of the compound of Formula C-1 provided in Example 1 of the present invention and the compound of Formula II-1 provided in Comparative Example 2.

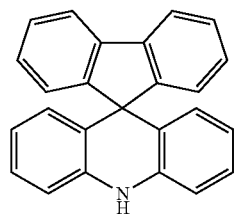 [SMILES: c1ccc2c(c1)Nc1ccccc1C21c2ccccc2-c2ccccc21]

formed by connection in the form of a spirocyclic ring. The TADF molecule having an electron-donating group formed by connection via a σ bond also has high $S_1$ and small $\Delta E_{ST}$ (FIG. 3), enabling efficient emission in the blue and deep blue regions. Moreover, the dihydro-acridinyl group and dibenzofuran are connected via a σ bond, which optimizes the hole and electron transport performances of the material molecules, and further improves the blue light-emitting efficiency of the device.

Moreover, the dihydro-acridine derivative of Formula C-1 has a high glass transition temperature, high thermal stability and morphological stability, and excellent film forming performance, and is not prone to crystallization when used as a material in the light emitting layer, thus facilitating the improvement of the performance and luminescence efficiency of the OLED device.

In an alternative embodiment, the guest luminescent material in the light emitting layer may also be any 9,10-dihydro-acridine derivative of Formulas (C-2)-(C-100).

In an alternative embodiment, the guest luminescent material in the light emitting layer may also be any other compounds having a chemical structure of general Formula (I).

Example 68

This example provides an organic light-emitting device, which is different from the organic light-emitting device provided in Example 67 in that the guest luminescent material in the light emitting layer is a 9,10-dihydro-acridine derivative having a structure below:

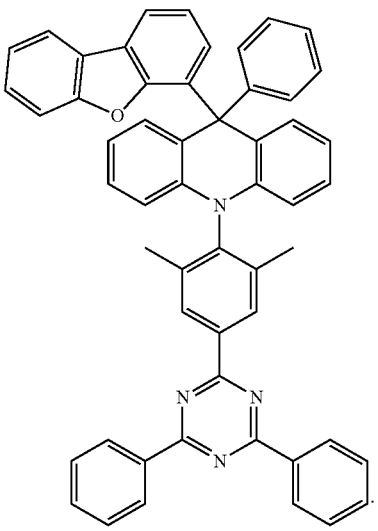

(C-3)

Example 69

This example provides an organic light-emitting device, which is different from the organic light-emitting device provided in Example 67 in that the guest luminescent material in the light emitting layer is a 9,10-dihydro-acridine derivative having a structure below:

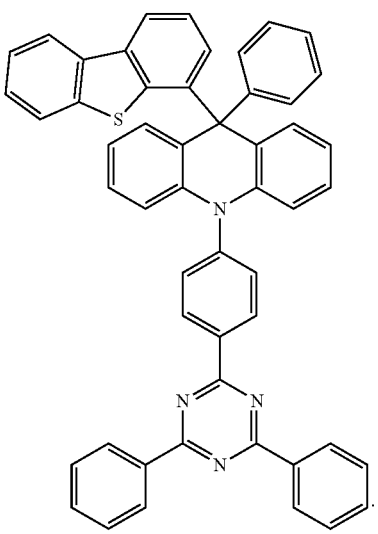

(C-10)

Example 70

This example provides an organic light-emitting device, which is different from the organic light-emitting device provided in Example 67 in that the guest luminescent material in the light emitting layer is a 9,10-dihydro-acridine derivative having a structure below:

(C-12)

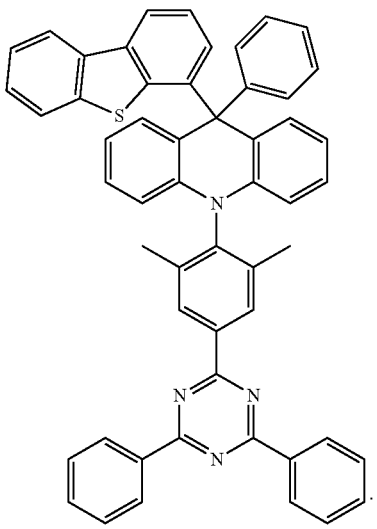

Example 71

This example provides an organic light-emitting device, which is different from the organic light-emitting device provided in Example 67 in that the guest luminescent material in the light emitting layer is a 9,10-dihydro-acridine derivative having a structure below:

(C-21)

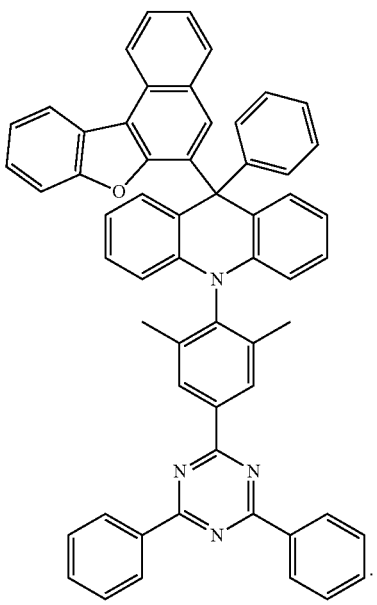

Example 72

This example provides an organic light-emitting device, which is different from the organic light-emitting device provided in Example 67 in that the guest luminescent material in the light emitting layer is a 9,10-dihydro-acridine derivative having a structure below:

(C-37)

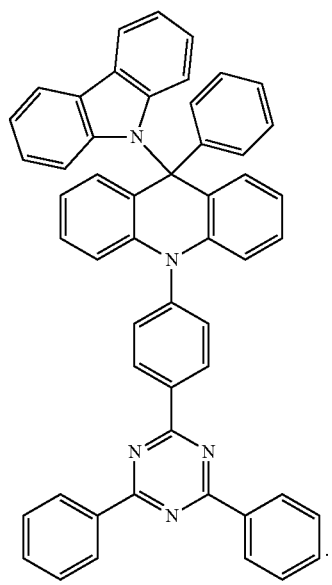

Example 73

This example provides an organic light-emitting device, which is different from the organic light-emitting device provided in Example 67 in that the guest luminescent material in the light emitting layer is a 9,10-dihydro-acridine derivative having a structure below:

(C-61)

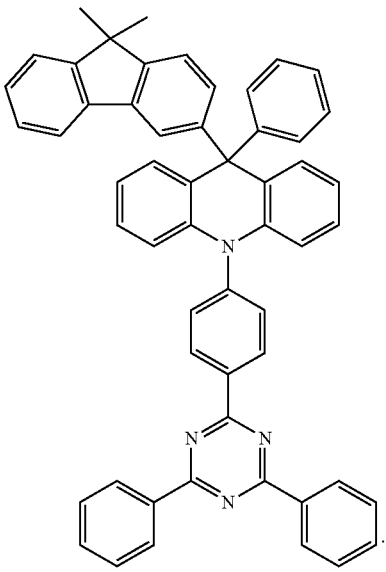

Example 74

This example provides an organic light-emitting device, which is different from the organic light-emitting device provided in Example 67 in that the guest luminescent material in the light emitting layer is a 9,10-dihydro-acridine derivative having a structure below:

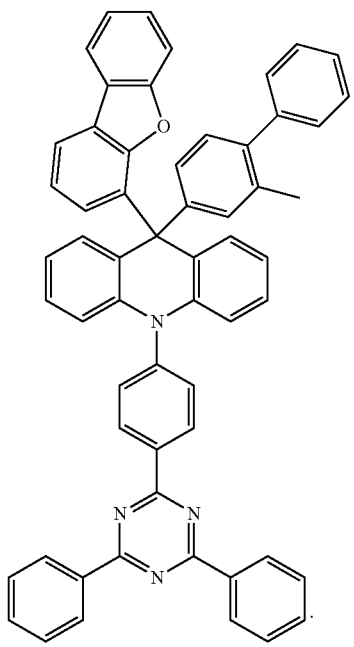

(C-72)

Example 75

This example provides an organic light-emitting device, which is different from the organic light-emitting device provided in Example 67 in that the guest luminescent material in the light emitting layer is a 9,10-dihydro-acridine derivative having a structure below:

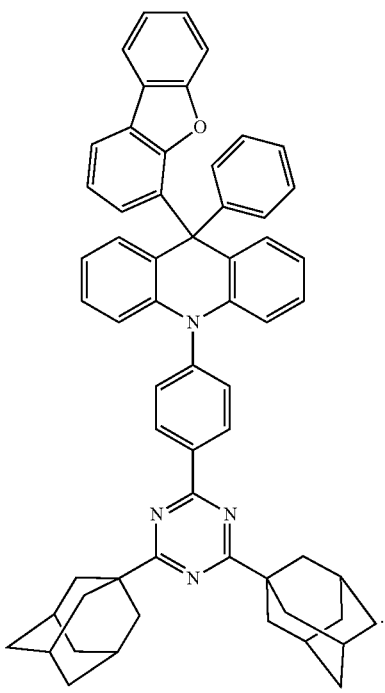

(C-80)

Example 76

This example provides an organic light-emitting device, which is different from the organic light-emitting device provided in Example 67 in that the guest luminescent material in the light emitting layer is a 9,10-dihydro-acridine derivative having a structure below:

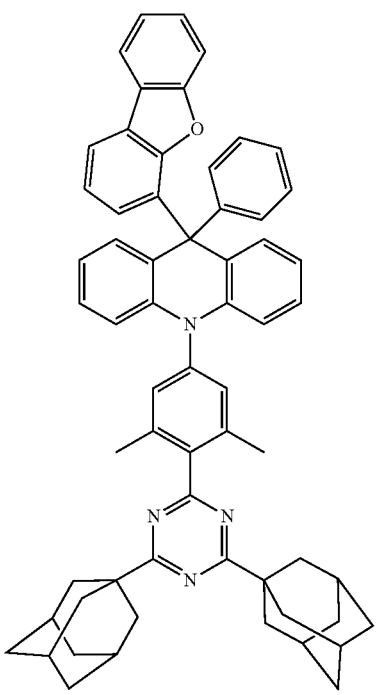

(C-82)

Example 77

This example provides an organic light-emitting device, which is different from the organic light-emitting device provided in Example 67 in that the guest luminescent material in the light emitting layer is a 9,10-dihydro-acridine derivative having a structure below:

(C-90)

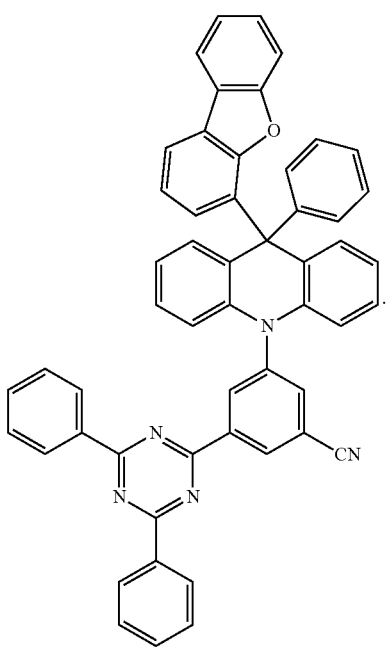

Comparative Example 1

This example provides an organic light-emitting device, which differs from the organic light-emitting device provided in Embodiment 7 only in that the guest luminescent material in the light emitting layer is the compound BD:

BD

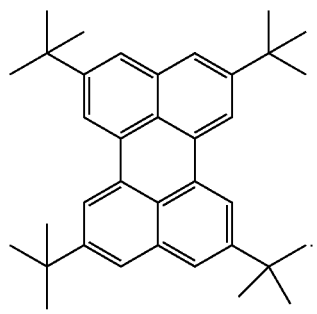

Comparative Example 2

This example provides an organic light-emitting device, which differs from the organic light-emitting device provided in Embodiment 7 only in that the guest luminescent material in the light emitting layer is a compound below:

(II-1)

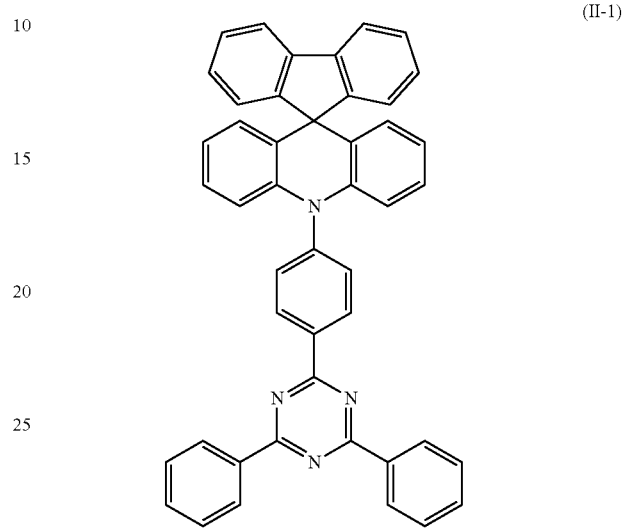

Test Example 1

1. Determination of Glass Transition Temperature

The glass transition temperature of the material according to the present invention was tested by differential scanning calorimetery (DSC) in a range from room temperature to 400° C. at a ramping rate of 10° C./min under nitrogen atmosphere.

2. The fluorescence and phosphorescence spectra of a solution of the 9,10-dihydro-acridine derivative in toluene (having a concentration of $10^{-5}$ mol/L) were measured at 298 K and 77 K, respectively, the corresponding singlet ($S_1$) and triplet ($T_1$) energy levels were calculated according to the formula $E=1240/\lambda$, and then a difference between the singlet and triplet energy levels of the 9,10-dihydro-acridine derivative was obtained. The difference between the energy levels of the 9,10-dihydro-acridine derivative is shown below.

TABLE 1

| 9,10-dihydro-acridine derivative | C-1 | C-3 | C-10 | C-12 | C-21 | C-37 | C-61 | C-72 | C-80 | C-82 | C-90 |
|---|---|---|---|---|---|---|---|---|---|---|---|
| Glass Transition Temperature (° C.) | 193 | 195 | 194 | 197 | 207 | 195 | 192 | 198 | 201 | 208 | 203 |
| $\Delta E_{ST}$ (eV) | 0.04 | 0.02 | 0.05 | 0.03 | 0.04 | 0.03 | 0.05 | 0.02 | 0.02 | 0.01 | 0.01 |
| $S_1$ (eV) | 2.65 | 2.69 | 2.65 | 2.71 | 2.70 | 2.72 | 2.75 | 2.70 | 2.70 | 2.74 | 2.73 |
| $T_1$ (eV) | 2.61 | 2.67 | 2.60 | 2.68 | 2.66 | 2.69 | 2.70 | 2.68 | 2.68 | 2.73 | 2.72 |

Test Example 2

The current, voltage, brightness, and luminescence spectrum of the device were tested synchronously using PR 650 scanning spectroradiometer and Keithley K 2400 digital source meter The organic light-emitting devices provided in Examples 67-77 and the comparative example were tested. The results are shown in Table 2.

TABLE 2

| | Guest luminescent material in light emitting layer | Maximum external quantum efficiency ($EQE_{MAX}$) (%) | Wavelength of emitted light ($EL_{MAX}$) (nm) | Chromaticity (CIE-X, Y) |
|---|---|---|---|---|
| Comparative Example 1 | BD | 7 | 465 | (0.20, 0.22) |
| Comparative Example 2 | II-1 | 16 | 485 | (0.17, 0.43) |
| Example 67 | C-1 | 15 | 471 | (0.15, 0.18) |
| Example 68 | C-3 | 17 | 463 | (0.15, 0.11) |
| Example 69 | C-10 | 16 | 472 | (0.16, 0.19) |
| Example 70 | C-12 | 19 | 460 | (0.15, 0.10) |
| Example 71 | C-21 | 20 | 463 | (0.15, 0.10) |
| Example 72 | C-37 | 14 | 461 | (0.16, 0.11) |
| Example 73 | C-61 | 13 | 458 | (0.15, 0.09) |
| Example 74 | C-72 | 16 | 465 | (0.15, 0.08) |
| Example 75 | C-80 | 18 | 460 | (0.15, 0.10) |
| Example 76 | C-82 | 17 | 454 | (0.15, 0.08) |
| Example 77 | C-90 | 19 | 459 | (0.15, 0.09) |

The organic light-emitting devices provided in Examples 67-77 and Comparative Examples 1 and 2 were tested. The results are shown in Table 2. Compared with the device provided in Comparative Example 1, the OLED devices provided in Examples 67-77 has high external quantum efficiency, high color purity, and high blue light emitting efficiency; and compared with the device provided in Comparative Example 2, the OLED devices provided in Examples 67-77 are more advantageous in light emission in a deep blue region, indicating that the 9,10-dihydro-acridine derivative provided in the present invention, when used as a guest luminescent material in the light emitting layer of an OLED device, can enable a deep blue light emitting device with high luminescence efficiency.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. A 9,10-dihydro-acridine derivative, having a structure of Formula (I):

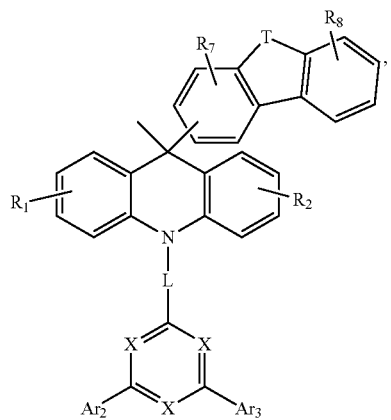

wherein each X is independently selected from N; and T is selected from O, S, or C($R_4$)($R_5$);

wherein L is independently selected from unsubstituted or substituted phenyl, and $Ar_1$-$Ar_3$ are each independently selected from phenyl, biphenylyl, adamantyl, or naphthyl that is unsubstituted or substituted with 1-5 $R_{1a}$, in which $R_{1a}$ is selected from a $C_1$-$C_6$, alkyl group;

wherein $R_1$, $R_2$, $R_4$, and $R_5$ are each independently selected from hydrogen, or methyl;

$R_7$-$R_8$ are each independently selected from hydrogen or a ring A that shares a side with the adjacent phenyl group to form a fused ring, where the ring A is selected from

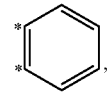

and the * represents substituted position.

2. The 9,10-dihydro-acridine derivative according to claim 1, having any of the following molecular structures:

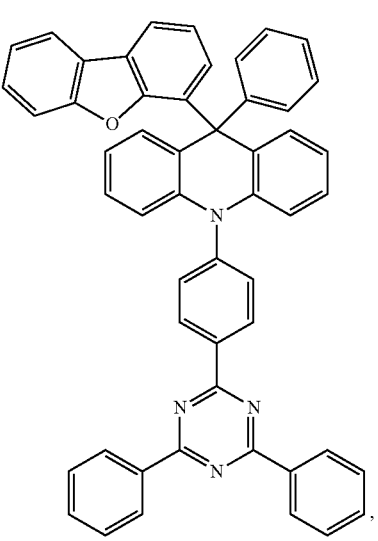

(C-1)

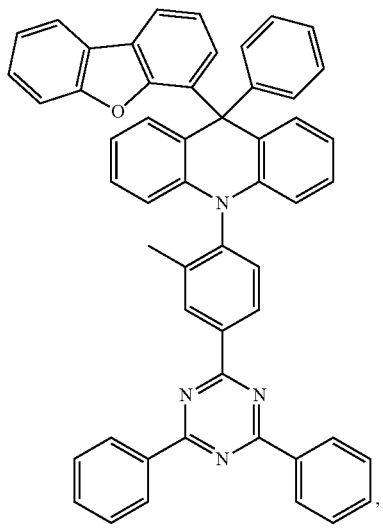
(C-2)
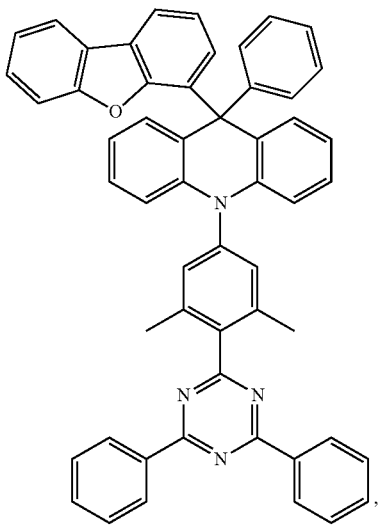
(C-5)
(C-3)
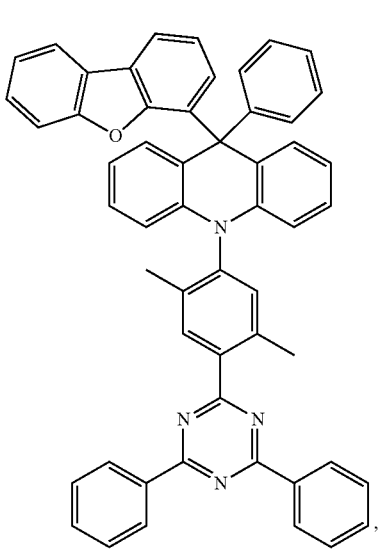
(C-6)
(C-4)
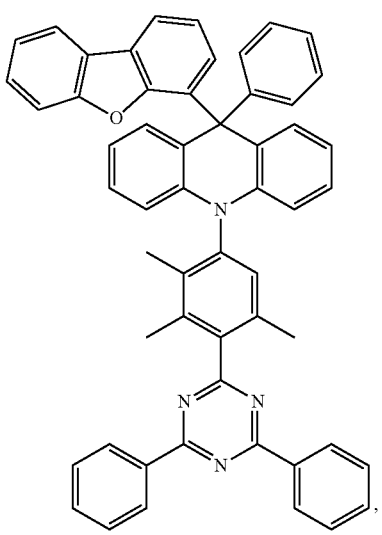
(C-7)

-continued
(C-8)
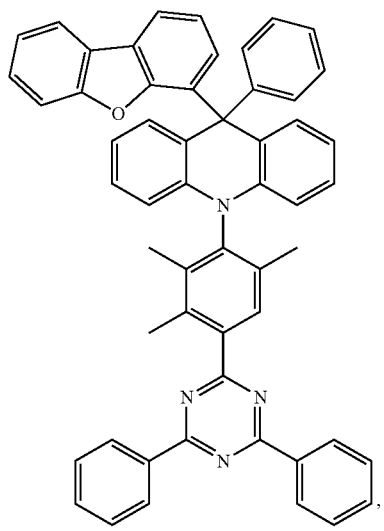
(C-9)
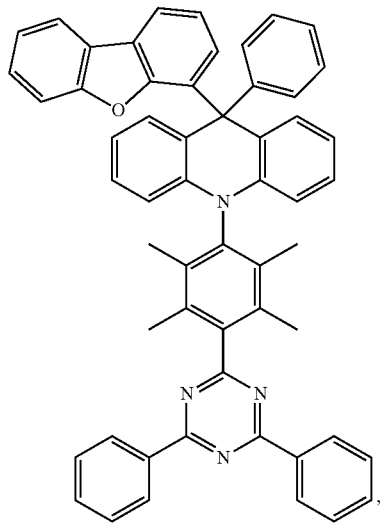
(C-10)
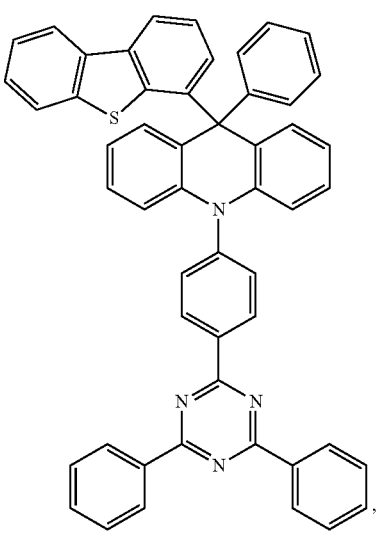
-continued
(C-11)
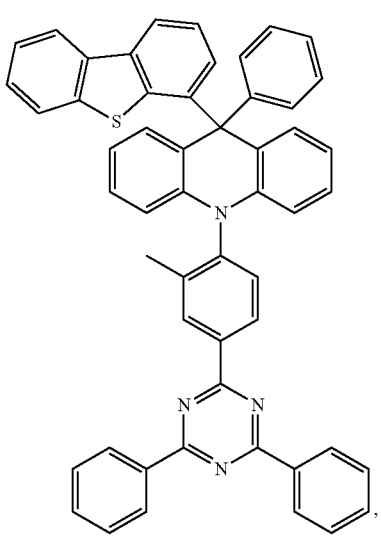
(C-12)
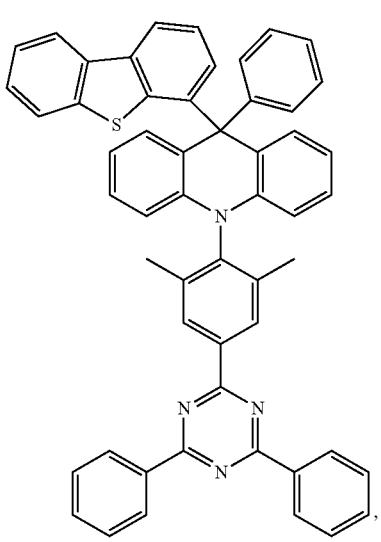
(C-13)
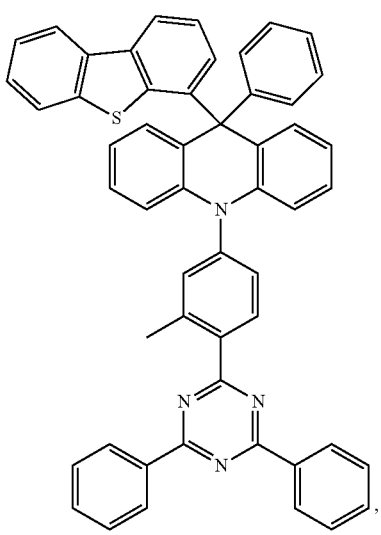

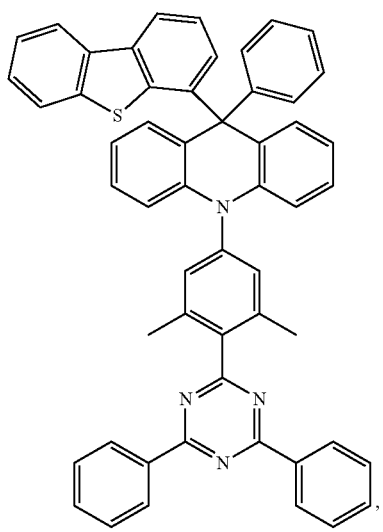
(C-14)
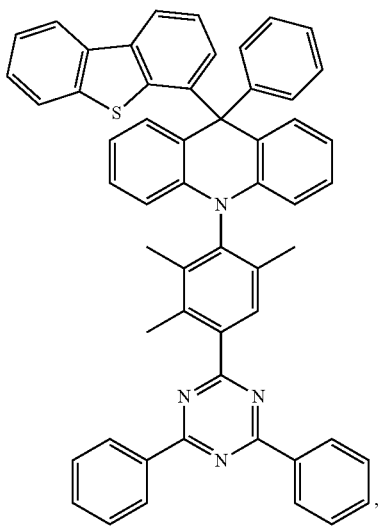
(C-17)
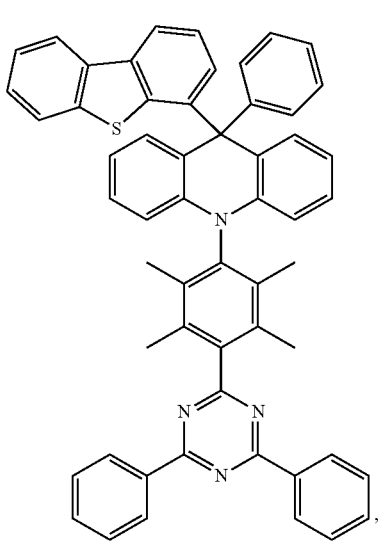
(C-18)
(C-15)
(C-16)
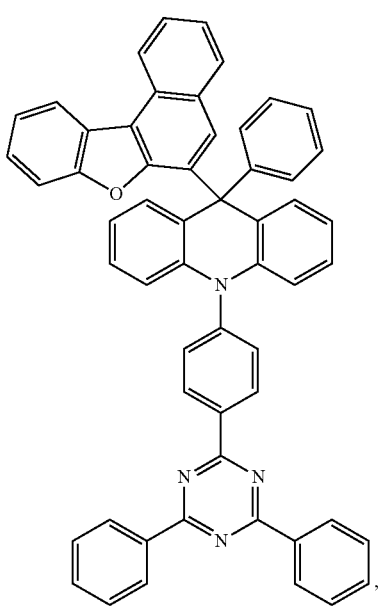
(C-19)

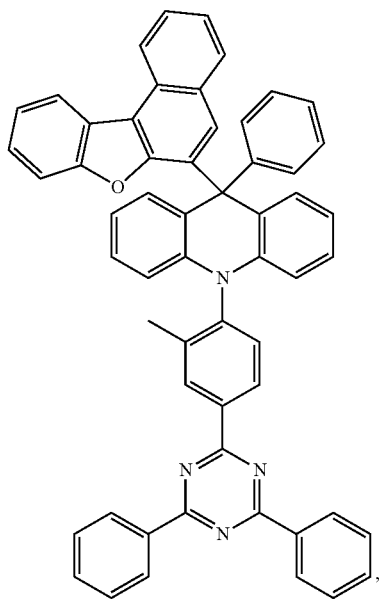
(C-20)
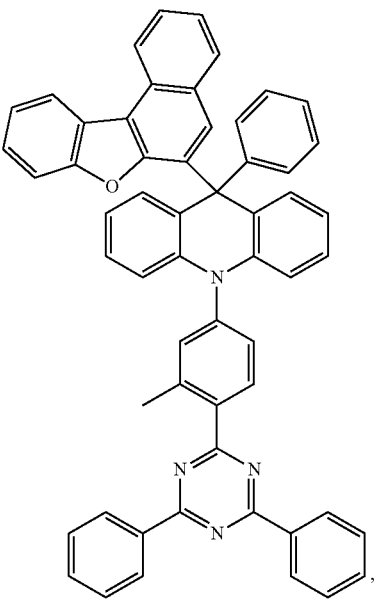
(C-22)
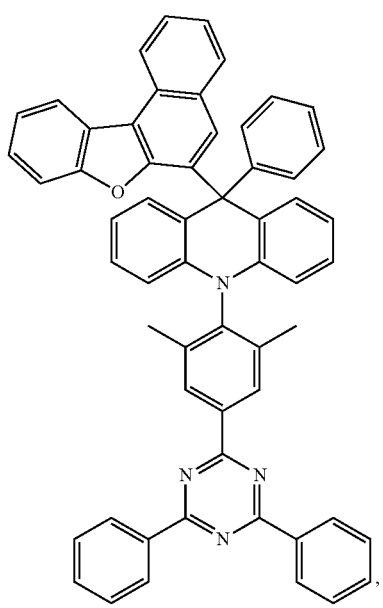
(C-21)
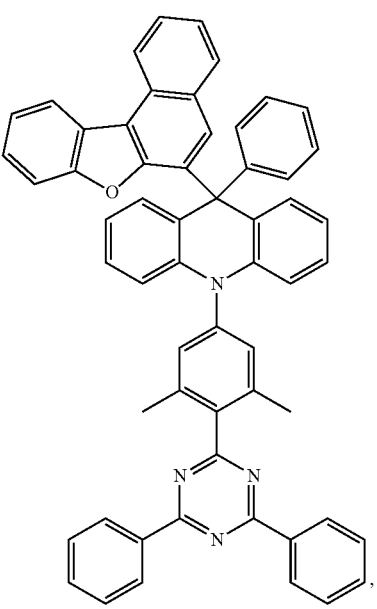
(C-23)

(C-24)
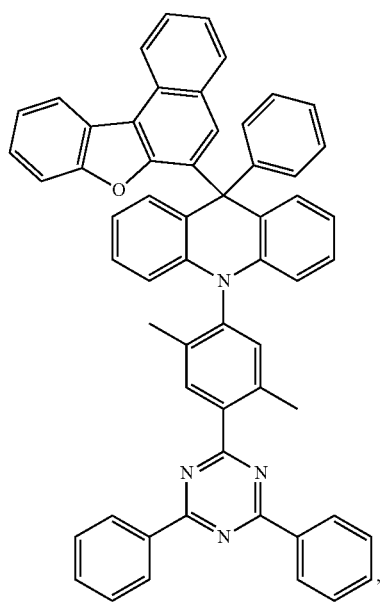
(C-26)
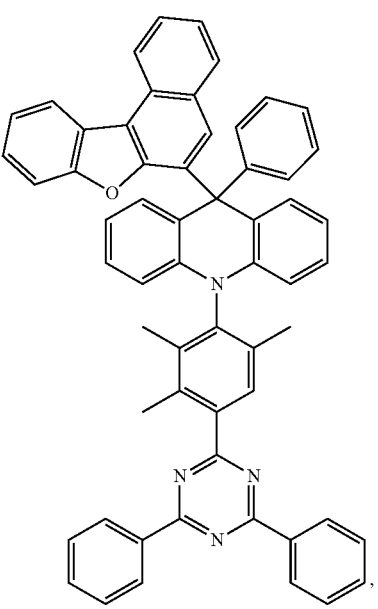
(C-25)
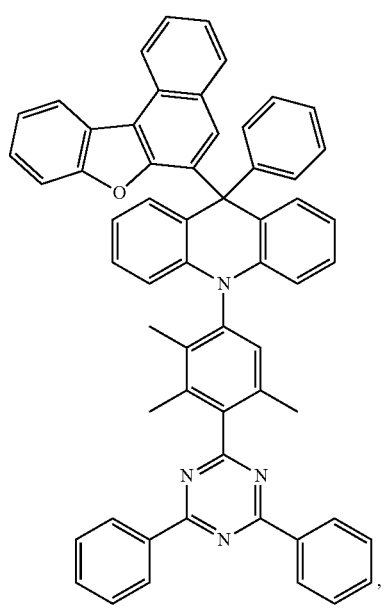
(C-27)
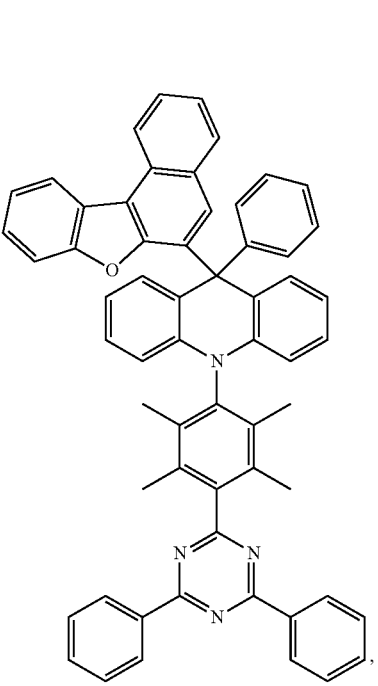

-continued
(C-55)
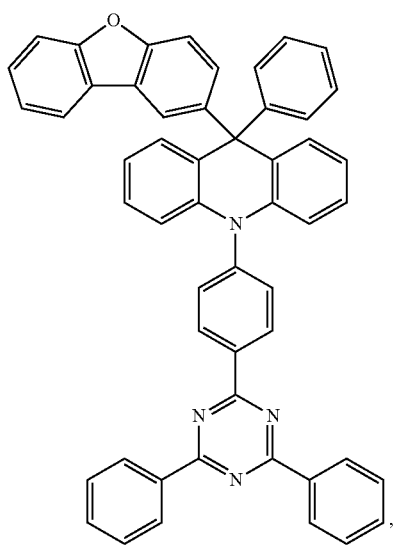
(C-56)
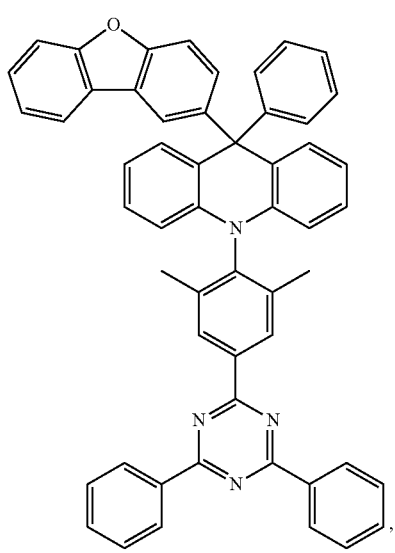
(C-57)
-continued
(C-58)
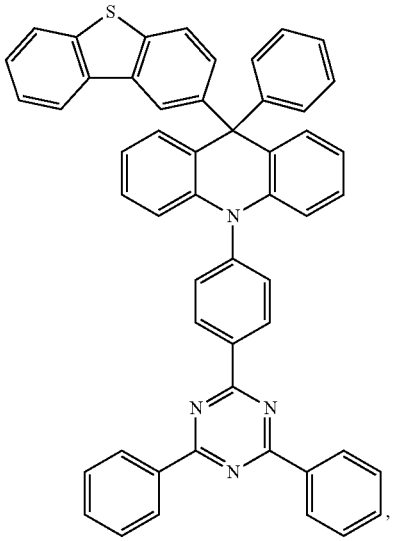
(C-61)
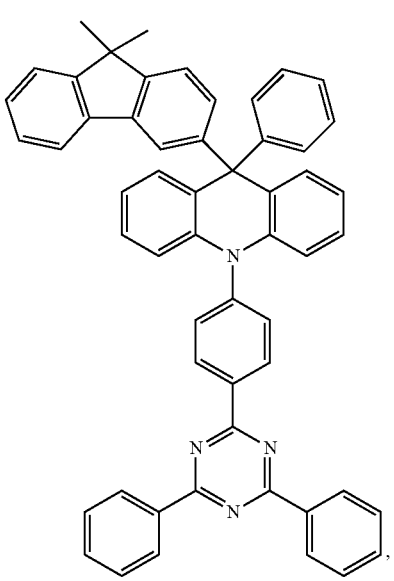
(C-62)
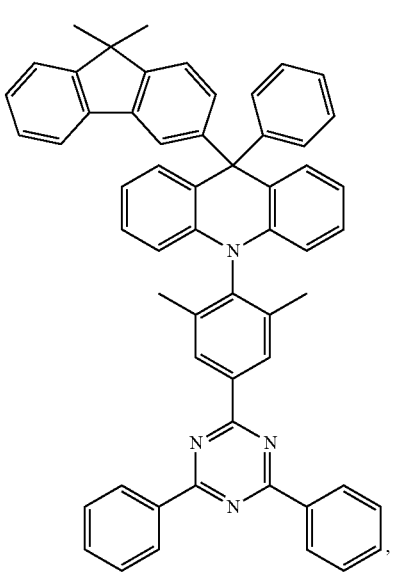

(C-63)
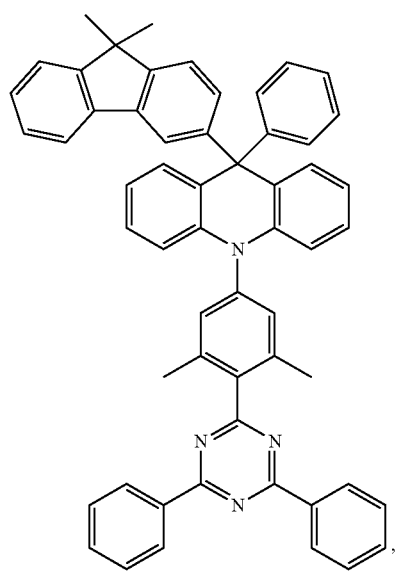
(C-64)
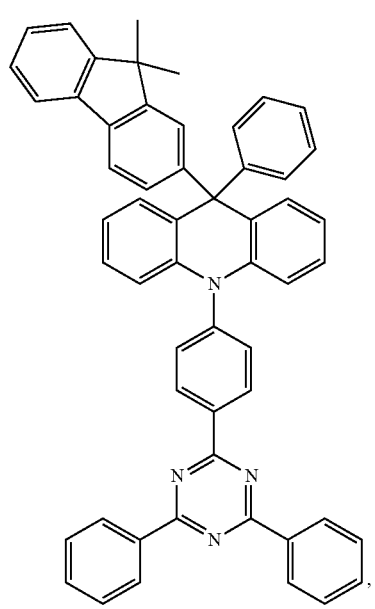
(C-65)
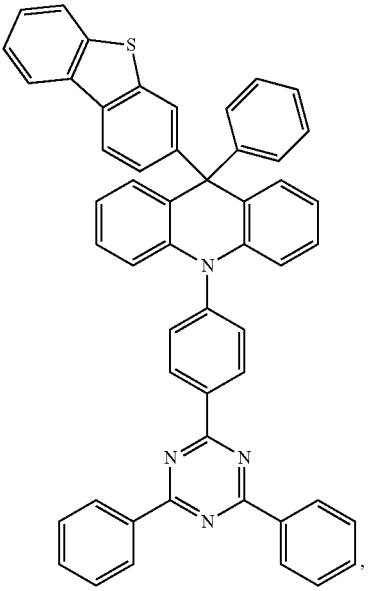
(C-66)
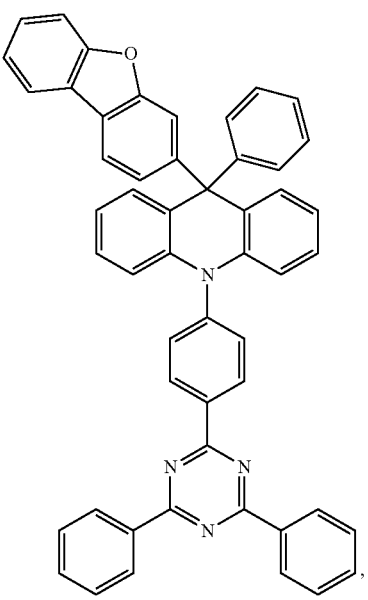

(C-67)
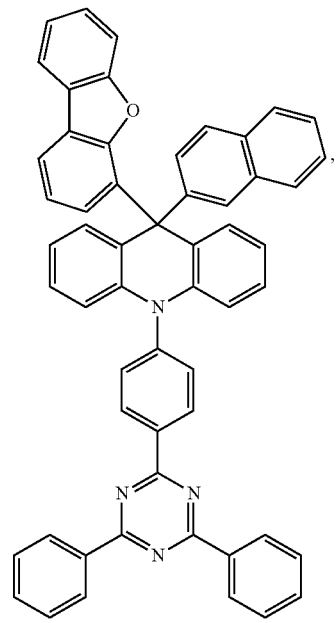
(C-70)
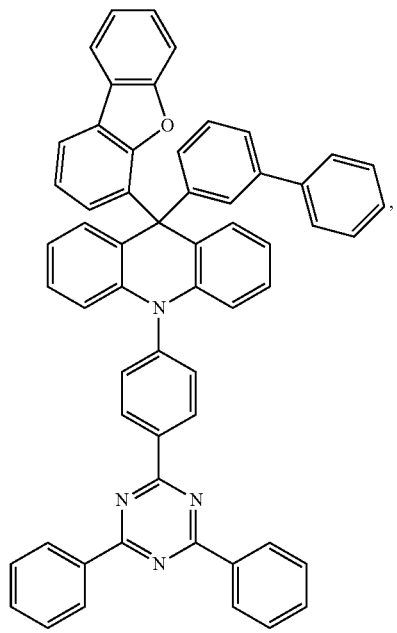
(C-71)
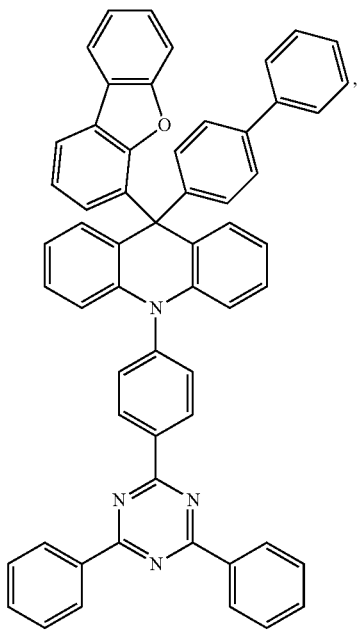
(C-72)
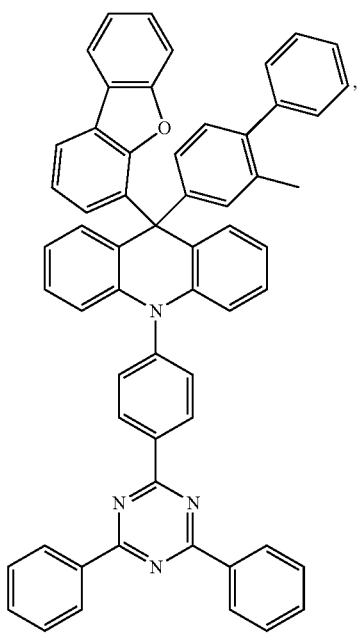

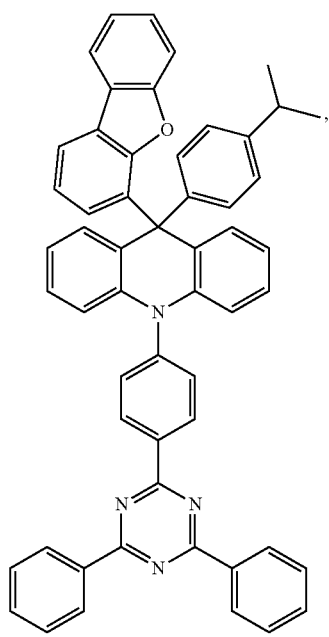
(C-73)
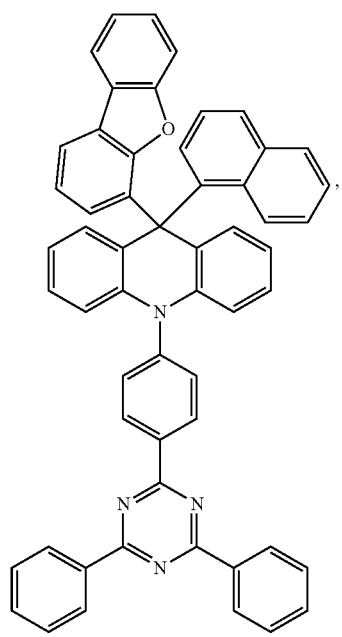
(C-78)
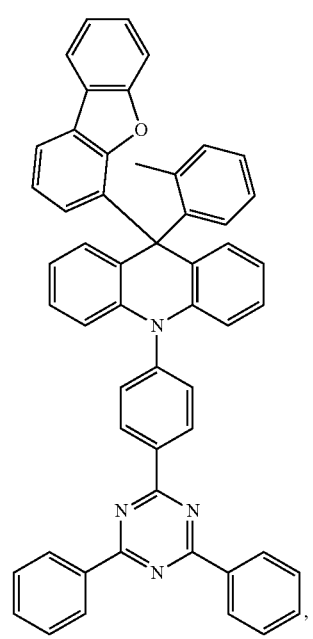
(C-75)
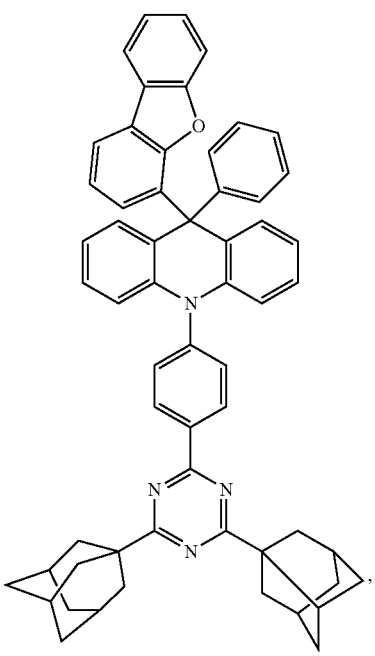
(C-80)

(C-81)

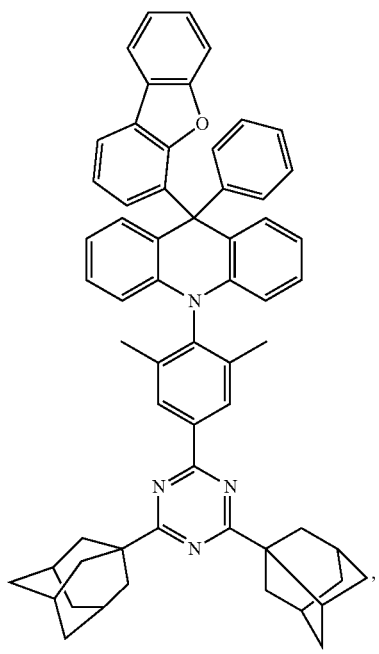

(C-82)

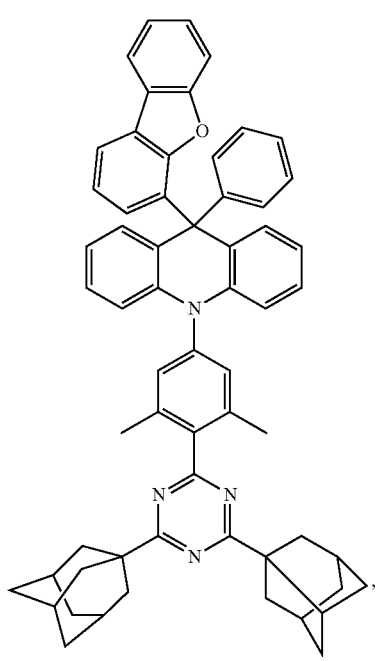

(C-90)

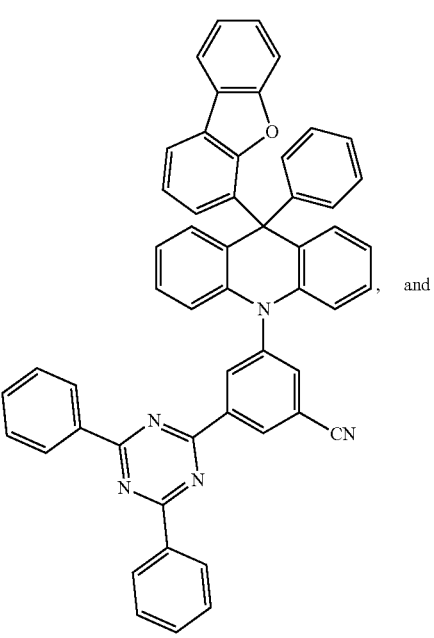

, and (C-100)

3. The 9,10-dihydro-acridine derivative according to claim 1, wherein the 9,10-dihydro-acridine derivative is a thermally activated delayed fluorescent material.

4. A method for preparing the 9,10-dihydro-acridine derivative according to claim 1, wherein the compound of Formula (I) is synthesized through the following steps:
subjecting a compound of Formula (A) and a compound of Formula (B) as starting materials to a nucleophilic addition reaction, to obtain an intermediate 1: subjecting the intermediate 1 and a compound of Formula (D) to a dehydration-condensation reaction in the presence of Eaton's Reagent, to obtain an intermediate 2; and subjecting the intermediate 2 and a compound of Formula (E) to a coupling reaction in the presence of a catalyst, to obtain the compound of Formula (I);
where the synthesis route for the compound of Formula (I) is shown below:

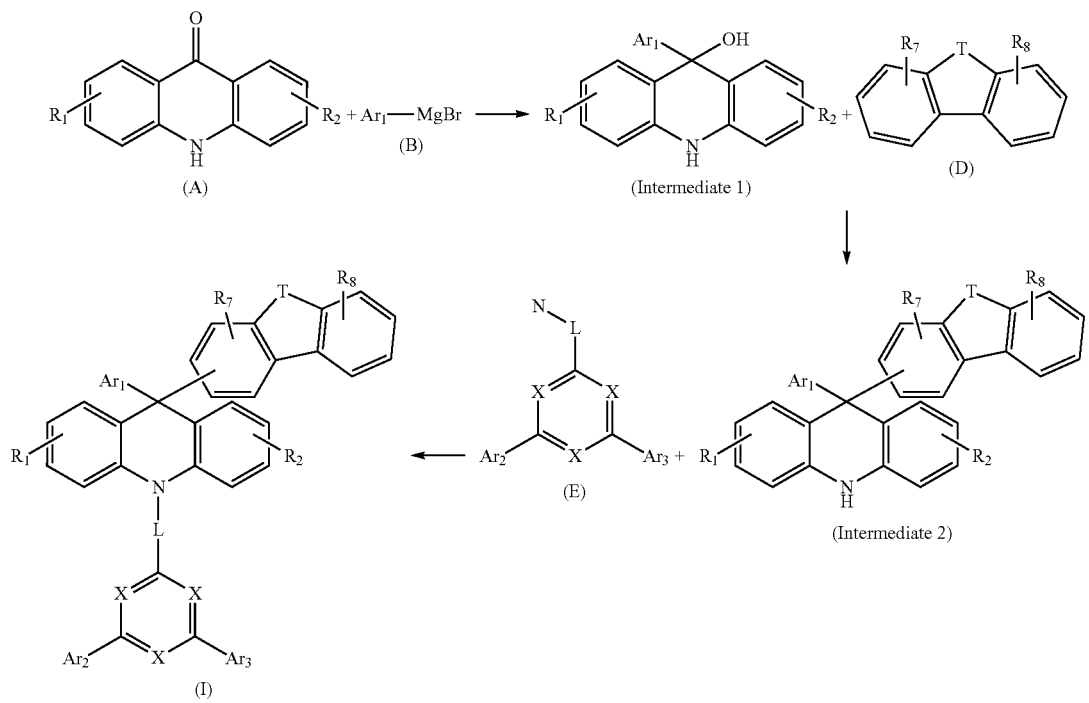

or subjecting the compound of Formula (A) and the compound of Formula (F) as starting materials to a nucleophilic addition reaction, to obtain an intermediate 3; subjecting the intermediate 3 to a nucleophilic substitution reaction, to obtain an intermediate 3'; subjecting the intermediate 3' and a compound of Formula (G) to a Suzuki reaction, to obtain an intermediate 4; and subjecting the intermediate 4 and the compound of Formula (E) to a coupling reaction in the presence of a catalyst, to obtain the compound of Formula (I);

where the synthesis route for the compound of Formula (I) is shown below:

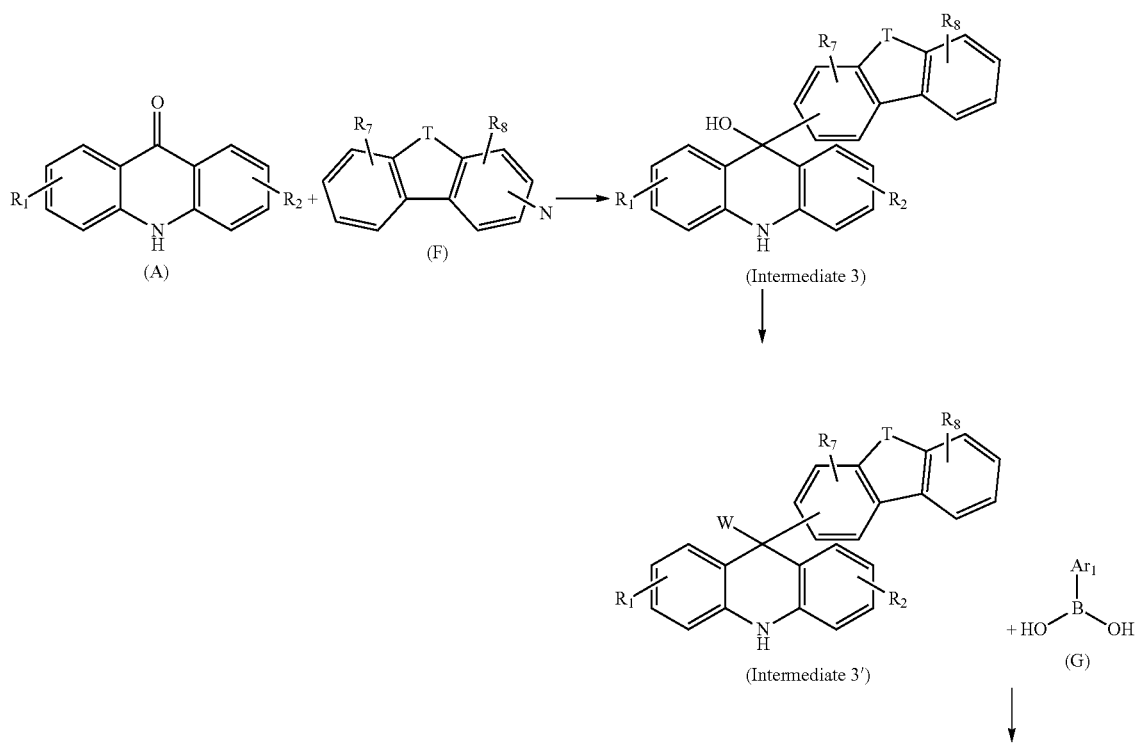

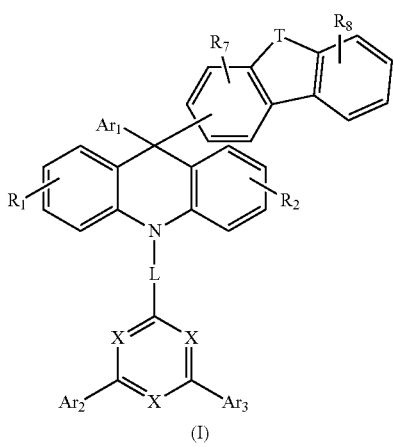

(I)

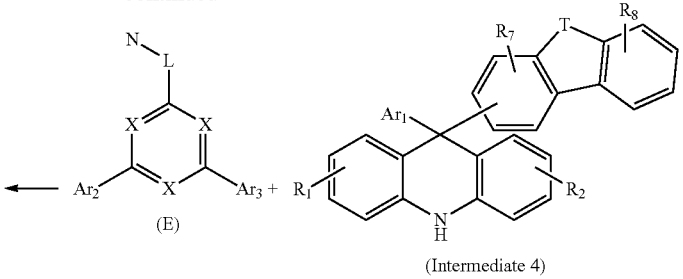

(Intermediate 4)

in which N is selected from fluoro, chloro, bromo or iodo, and W is selected from fluoro, chloro, bromo, iodo or triflyl.

5. An organic light-emitting device, having at least one functional layer containing a 9,10-dihydro-acridine derivative according to claim 1.

6. The organic light-emitting device according to claim 5, wherein the functional layer is a light emitting layer.

7. The organic light-emitting device according to claim 6, wherein the material of the light emitting layer comprises a host material and a guest luminescent dye, where the guest luminescent dye is the 9,10-dihydro-acridine derivative.

8. The organic light-emitting device according to claim 6, wherein the material of the light emitting layer comprises a host material and a guest luminescent dye, where the host material is the 9,10-dihydro-acridine derivative, and the guest luminescent dye used has thermally activated delayed fluorescence.

\* \* \* \* \*